(12) United States Patent
Doshi et al.

(10) Patent No.: US 7,987,852 B2
(45) Date of Patent: *Aug. 2, 2011

(54) NASAL DEVICES

(75) Inventors: Rajiv Doshi, Los Altos, CA (US); Bryan Loomas, Los Gatos, CA (US); Ryan Kendall Pierce, San Francisco, CA (US); Elliot Sather, San Francisco, CA (US); Arthur G. Sandoval, San Francisco, CA (US); Jeffrey W. Servaites, San Francisco, CA (US); Sandrine Lebas, San Francisco, CA (US); Matthew Durack, San Francisco, CA (US)

(73) Assignee: Ventus Medical, Inc., Belmont, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 12/369,681

(22) Filed: Feb. 11, 2009

(65) Prior Publication Data
US 2009/0188493 A1 Jul. 30, 2009

Related U.S. Application Data

(63) Continuation of application No. 11/811,339, filed on Jun. 7, 2007, now Pat. No. 7,506,649.

(60) Provisional application No. 60/905,850, filed on Mar. 7, 2007, provisional application No. 60/859,715, filed on Nov. 16, 2006, provisional application No. 60/811,814, filed on Jun. 7, 2006.

(51) Int. Cl.
*A61G 10/00* (2006.01)

(52) U.S. Cl. ......... 128/207.18; 128/206.15; 128/206.18; 128/206.11; 128/204.11

(58) Field of Classification Search ............. 128/206.11, 128/204.12, 204.11, 207.18, 206.18, 206.15
See application file for complete search history.

(56) References Cited

U.S. PATENT DOCUMENTS

| 628,111 | A | 7/1899 | McHatton |
| 669,098 | A | 3/1901 | Overshiner |
| 675,275 | A | 5/1901 | Gunning |
| 746,869 | A | 12/1903 | Moulton |
| 774,446 | A | 11/1904 | Moulton |
| 810,617 | A | 1/1906 | Carence |
| 1,819,884 | A | 8/1931 | Fores |
| 2,198,959 | A | 4/1940 | Clarke |

(Continued)

FOREIGN PATENT DOCUMENTS
EP 1157663 A1 11/2001
(Continued)

OTHER PUBLICATIONS

Doshi et al.; U.S. Appl. No. 12/711,782 entitled "Respiratory devices," filed Feb. 24, 2010.

(Continued)

*Primary Examiner* — Steven O Douglas
(74) *Attorney, Agent, or Firm* — Shay Glenn LLP

(57) ABSTRACT

Described herein are adhesive nasal devices. In particular, the adhesive nasal respiratory devices described herein are configured to be worn in communication with a subject's nasal cavity and may include a rim body having a passageway therethrough, an airflow resistor in communication with the passageway of the rim body, and a flexible, adhesive holdfast layer extending outward from the periphery of the rim body. The rim body region may be formed from multiple parts (e.g., a first and a second rim body region), and the airflow resistor may be secured between the parts forming the rim body. Methods of manufacturing and assembling these adhesive nasal devices are also described.

31 Claims, 43 Drawing Sheets

U.S. PATENT DOCUMENTS

| | | |
|---|---|---|
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,143,872 A | 3/1979 | Havstad et al. |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,640,277 A | 2/1987 | Meyer et al. |
| 4,651,873 A | 3/1987 | Stolcenberg et al. |
| 4,739,987 A | 4/1988 | Nicholson |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,823,187 A | 10/1998 | Estes et al. |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,213,955 B1 | 4/2001 | Karakasoglu et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 | 3/2003 | Soltesz et al. |
| 6,561,188 B1 | 5/2003 | Ellis |
| 6,562,057 B2 | 5/2003 | Santin |
| 6,568,387 B2 | 5/2003 | Davenport et al. |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,626,172 B1 | 9/2003 | Karow et al. |
| 6,626,179 B1 | 9/2003 | Pedley |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,811,538 B2 | 11/2004 | Westbrook et al. |
| 6,848,446 B2 | 2/2005 | Noble |
| 6,863,066 B2 | 3/2005 | Ogle |
| 6,872,439 B2 | 3/2005 | Fearing et al. |
| 6,921,574 B2 | 7/2005 | Cinelli et al. |
| 6,997,177 B2 | 2/2006 | Wood |
| 7,011,723 B2 | 3/2006 | Full et al. |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |
| 7,263,996 B2 | 9/2007 | Yung Ho |
| 7,506,649 B2 | 3/2009 | Doshi et al. |
| 7,559,326 B2 | 7/2009 | Smith et al. |
| 2001/0051799 A1 | 12/2001 | Ingenito |
| 2001/0056274 A1 | 12/2001 | Perkins et al. |
| 2002/0062120 A1 | 5/2002 | Perkins et al. |
| 2002/0077593 A1 | 6/2002 | Perkins et al. |
| 2002/0112729 A1 | 8/2002 | DeVore et al. |
| 2003/0024527 A1 | 2/2003 | Ginn |
| 2003/0050648 A1 | 3/2003 | Alferness et al. |
| 2003/0070682 A1 | 4/2003 | Wilson et al. |
| 2003/0106555 A1 | 6/2003 | Tovey |
| 2003/0106556 A1 | 6/2003 | Alperovich et al. |
| 2003/0140925 A1 | 7/2003 | Sapienza et al. |
| 2003/0154988 A1 | 8/2003 | DeVore et al. |

| | | | |
|---|---|---|---|
| 2003/0158515 A1 | 8/2003 | Gonzalez et al. |
| 2003/0195552 A1 | 10/2003 | Santin |
| 2003/0209247 A1 | 11/2003 | O'Rourke |
| 2004/0016432 A1 | 1/2004 | Genger et al. |
| 2004/0020492 A1 | 2/2004 | Dubrul et al. |
| 2004/0020493 A1 | 2/2004 | Wood |
| 2004/0055606 A1 | 3/2004 | Hendricksen et al. |
| 2004/0112379 A1 | 6/2004 | Djupesland |
| 2004/0194779 A1 | 10/2004 | Doshi |
| 2004/0254491 A1 | 12/2004 | Ricciardelli |
| 2004/0261791 A1 | 12/2004 | Horian |
| 2004/0261798 A1 | 12/2004 | Rimkus |
| 2005/0010125 A1 | 1/2005 | Joy et al. |
| 2005/0011524 A1 | 1/2005 | Thomlinson et al. |
| 2005/0033344 A1 | 2/2005 | Dillard et al. |
| 2005/0051170 A1 | 3/2005 | Koo |
| 2005/0284479 A1 | 12/2005 | Schrader et al. |
| 2006/0016450 A1 | 1/2006 | Pearson et al. |
| 2006/0085027 A1 | 4/2006 | Santin et al. |
| 2006/0144398 A1 | 7/2006 | Doshi et al. |
| 2006/0150978 A1 | 7/2006 | Doshi et al. |
| 2006/0150979 A1 | 7/2006 | Doshi et al. |
| 2006/0169285 A1 | 8/2006 | Bovo |
| 2006/0283461 A1 | 12/2006 | Lubke et al. |
| 2007/0051364 A1 | 3/2007 | Jacobson et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0277832 A1 | 12/2007 | Doshi et al. |
| 2007/0283962 A1 | 12/2007 | Doshi et al. |
| 2007/0287976 A1 | 12/2007 | Sherrill |
| 2007/0295338 A1 | 12/2007 | Loomis et al. |
| 2008/0023007 A1 | 1/2008 | Dolezal et al. |
| 2008/0142018 A1 | 6/2008 | Doshi et al. |
| 2008/0173309 A1 | 7/2008 | Doshi |
| 2008/0178874 A1 | 7/2008 | Doshi et al. |
| 2008/0221470 A1 | 9/2008 | Sather et al. |
| 2009/0050144 A1 | 2/2009 | Pierce et al. |
| 2009/0194100 A1 | 8/2009 | Minagi |
| 2010/0326447 A1 | 12/2010 | Loomas et al. |
| 2011/0005520 A1 | 1/2011 | Doshi et al. |
| 2011/0005528 A1 | 1/2011 | Doshi et al. |
| 2011/0005529 A1 | 1/2011 | Doshi et al. |
| 2011/0005530 A1 | 1/2011 | Doshi et al. |

FOREIGN PATENT DOCUMENTS

| | | |
|---|---|---|
| EP | 1205203 A2 | 5/2002 |
| GB | 2324729 A | 4/1998 |
| RU | 2048820 C1 | 11/1995 |
| SU | 1586709 A1 | 8/1990 |
| WO | WO 90/12614 A1 | 11/1990 |
| WO | WO 95/17220 A1 | 6/1995 |
| WO | WO 95/33520 A1 | 12/1995 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO 2006/063339 A2 | 6/2006 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

http://chinookmed.com/index.cfm/fa/product.display&Product_ID=275; accessed Nov. 28, 2007.

Dillard, D. et al., Evaluation of a novel intra-bronchial valve to produce lung volume reduction, World Congress of Bronchology, Jun. 2002 (figs. 1-4 available upon request).

Doshi et al.; U.S. Appl. No. 12/329,271 entitled "Packaging and dispensing nasal devices," filed Dec. 5, 2008.

Doshi et al.; U.S. Appl. No. 12/329,895 entitled "Delayed resistance nasal devices and methods of use," filed Dec. 8, 2008.

Doshi et al.; U.S. Appl. No. 12/364,264 entitled "CPAP interface and backup devices," filed Feb. 2, 2009.

Sather et al.; U.S. Appl. No. 12/405,837 entitled "Nasal devices with noise-reduction and methods of use," filed Mar. 17, 2009.

Ferdinand et al.; U.S. Appl. No. 12/485,750 entitled "Adjustable resistance nasal devices," filed Jun. 16, 2009.

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Doshi et al.; U.S. Appl. No. 12/884,140 entitled "Sealing nasal devices for use while sleeping," filed Sep. 16, 2010.

Doshi et al.; U.S. Appl. No. 12/884,146 entitled "Nasal devices for use while sleeping," filed Sep. 16, 2010.

Doshi et al.; U.S. Appl. No. 12/955,633 entitled "Nasal respiratory devices," filed Nov. 29, 2010.

Sather et al.; U.S. Appl. No. 12/941,734 entitled "Nasal devices having a safe failure mode and remotely activatable," filed Nov. 8, 2010.

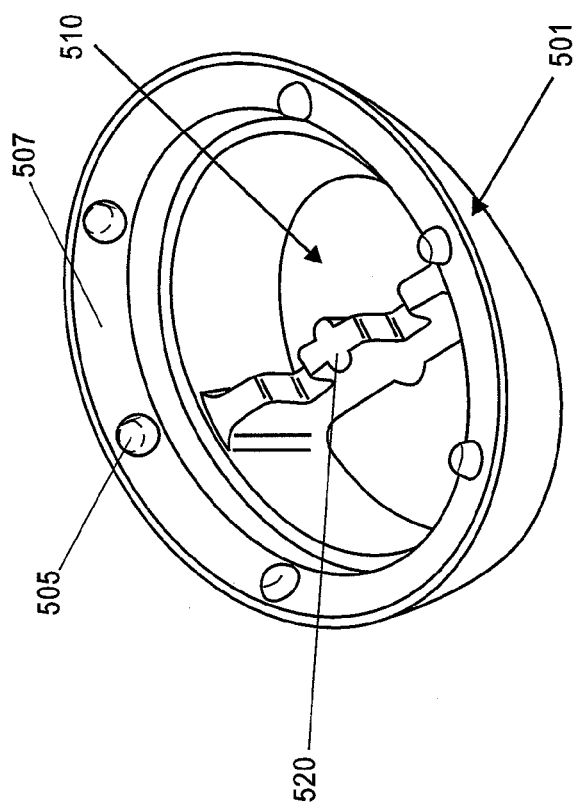
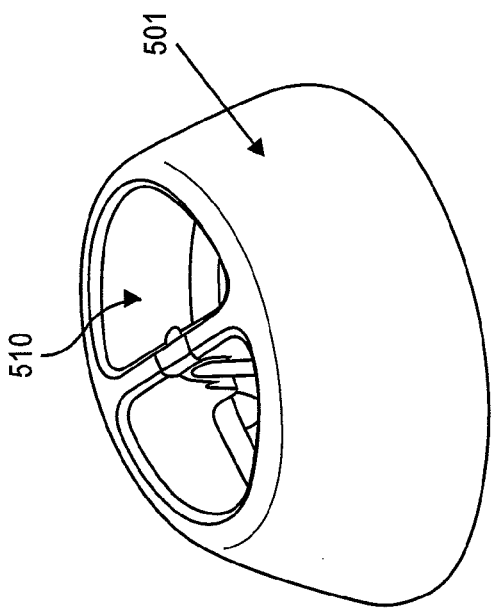
FIG. 5B
FIG. 5A

1401

BOTTOM VIEW

SIDE VIEW
(WORN)

FRONT VIEW
(WORN)

ADHESIVE OR
OTHER METHOD (SNAPS?)
KEEP ADAPTER IN
PLACE 3205
3202

3202

NASAL DEVICES

CROSS-REFERENCE TO RELATED APPLICATIONS

This application is a continuation of U.S. patent application Ser. No. 11/811,339 filed Jun. 7, 2007, titled "NASAL DEVICES", which claims priority to U.S. Provisional Patent Applications: Ser. No. 60/905,850 filed Mar. 7, 2007, titled "NASAL DEVICES"); Ser. No. 60/859,715, filed Nov. 16, 2006, titled "NASAL DEVICES"); and Ser. No. 60/811,814, filed Jun. 7, 2006, titled "RESPIRATORY DEVICES". Each of these provisional patent applications is incorporated herein by reference in its entirety.

BACKGROUND OF THE INVENTION

The devices, methods, and kits described herein relate generally to nasal devices. These nasal devices may be therapeutically used to treat medical disorders, particularly in the fields of cardiovascular medicine, sleep medicine, pulmonology, gastroenterology, and internal medicine.

Nasal respiratory devices have been well-described in the following U.S. patent applications, each of which is incorporated herein in its entirety: U.S. patent application Ser. No. 11/298,640 (titled "NASAL RESPIRATORY DEVICES") filed Dec. 8, 2005; U.S. patent application Ser. No. 11/298,339 (titled "RESPIRATORY DEVICES") filed Dec. 8, 2005; and U.S. patent application Ser. No. 11/298,362 (titled "METHODS OF TREATING RESPIRATORY DISORDERS") filed Dec. 8, 2005. These patent applications generally describe nasal respiratory devices and methods for treating a variety of medical diseases through the use of such devices. Although these patent applications generally describe variations of nasal respiratory devices, certain specific variations of nasal respiratory devices have not previously been described and may provide additional properties in both use and manufacture. Described below are new nasal devices, accessories for nasal devices, methods of using and method of manufacturing nasal devices, and kits including nasal devices.

SUMMARY OF THE INVENTION

Described herein are specific variations of adhesive nasal devices, accessories for adhesive nasal devices, methods of manufacturing adhesive nasal devices, methods of using adhesive nasal devices, and kits including adhesive nasal devices. Adhesive nasal devices may be worn by a subject to modify the airflow thorough one or (more typically) both nostrils. As described in more detail below, an adhesive nasal device may be secured at least partly over or at least partly within the subject's nostril (or nostrils) so that airflow through the nostrils passes primarily (or exclusively) through the nasal device. Generally, the adhesive nasal device is removably secured over the subject's nostrils by an adhesive.

As used herein the term "adhesive nasal device" may refer to a device for covering one or both of a subject's nostrils. Thus, the description herein may generally apply to nasal respiratory devices adapted to fit over both of a subject's nostrils.

The adhesive nasal devices described herein may include a rim body region having one or more passageways formed therethrough. An airflow resistor (e.g., valve) may be secured in communication with a passageway through the rim body of the adhesive nasal device. The airflow resistor may regulate flow of air into and out of the nostril, and through the device. In particular, the airflow resistor may inhibit expiration more than inspiration. In some variations, the adhesive nasal device includes two airflow resistors, configured so that one airflow resistor is in fluid communication with each nostril. In some variations, an adhesive nasal device is worn in communication with each nostril (thus, a subject may wear two such devices). In addition, an adhesive nasal device includes an adhesive holdfast (or holdfast region) configured to secure the adhesive nasal device in communication with the subject's nasal passageway(s).

Described herein are adhesive nasal devices adapted to be secured (e.g., removably secured) in communication with a subject's nasal cavity. The device may include a rim body having a passageway therethrough, an airflow resistor in communication with the passageway of the rim body, a thin, flexible, adhesive holdfast layer extending outward from the periphery of the rim body, the adhesive holdfast layer comprising an adhesive substrate and a biocompatible adhesive, and a protective cover configured to be removed from the adhesive holdfast to expose at least a portion of the biocompatible adhesive. The airflow resistor may be configured to inhibit airflow during expiration more than airflow during inspiration.

The rim body may be a stiff or rigid rim body or in some cases may be flexible or less rigid. In some variations, the adhesive holdfast layer is a thin layer that has a substantially flat surface on two sides, and a relatively thin edge between the two sides. One of these two sides may be configured as a skin-contacting (adhesive) side. In some variations, the stiff rim body includes an outer rim body secured to an inner rim body. As described herein, the term "outer rim body" may refer to the portion of the rim body that extends furthest from the subject when the device is worn by the subject, and the term "inner rim body" may refer to the portion of the rim body that is closest to the subject when the device is worn by the subject. In some variations, the rim body is formed by a first and a second rim body region that correspond to an outer and an inner rim body region. In other variations, the first and second rim body regions correspond to a lateral and medial body region (e.g., lateral and medial side-by-side body regions).

The airflow resistor may be secured in communication with the passageway at any region, including within the stiff rim body. For example, the airflow resistor may be secured between the first and the second rim body regions.

In some variations, the adhesive nasal devices include a second rim body having a second airflow passage therethrough and a second airflow resistor secured in communication with the second airflow passage. Thus, the adhesive nasal device may have two passageways, and each passageway may be configured to communicate with one of the subject's nasal passageways or nostrils. The adhesive holdfast may include a bridge connecting the first and second rim bodies. The adhesive nasal device may also include a tab or handle configured to be grasped by a subject applying or removing the device. For example, the holdfast region may include a tab or handle.

The airflow resistor may be any appropriate airflow resistor. For example, the airflow resistor may include a flap valve. The different regions and components of the device may be made of any appropriate material, but especially biocompatible materials, since the device is to be worn by the subject. For example, the rim body may be made of medical grade plastic, including a medical grade plastic selected from the group consisting of: Acrylonitrile Butadiene Styrene (ABS), polypropylene, polyethylene, polyurethane, polycarbonate, and polyetheretherketone.

Also described herein are adhesive nasal device adapted to be secured in communication with a subject's nasal cavity. These devices may include a first rim body, a second rim body (wherein the first rim body is attached to the second rim body and the combined first and second rim bodies include an airflow passage therethrough), an airflow resistor in communication with the airflow passage, and an adhesive holdfast secured to the combined first and second rim bodies, wherein the adhesive holdfast comprises a biocompatible adhesive configured to secure the nasal device in alignment with the subject's nasal orifice.

As described, the airflow resistor may be configured to inhibit airflow during expiration more than airflow during inspiration. For example, the airflow resistor may be secured between the first and second rim bodies, and may be configured as a flap valve. The first rim body may be attached to the second rim body by any securement means. For example, the first and second rim body regions may be attached to each other by a snap or press fit, by a weld (e.g., an ultrasonic weld), by a glue or epoxy, or the like. These devices may include a third rim body that is attached to a fourth rim body, wherein the combined third and fourth rim bodies include a second airflow passage therethrough and a second airflow resistor secured in communication with the second airflow passage, and the adhesive holdfast may include a bridge between the combined first and second rim bodies and the combined third and fourth rim bodies.

The first rim body (and the third rim body, if present) may include a flanged rim. The adhesive holdfast may comprise a flexible adhesive substrate. The adhesive holdfast may include a protective cover configured to be removed by removing the cover off of an adhesive region of the adhesive substrate. Thus, the protective cover protects the adhesive until this region of the holdfast is adhesively secured to the subject. The adhesive holdfast may include an opening within the annular region through which the combined first and second rim body regions extend. Thus, in some variations, the adhesive holdfast extends along the outer periphery of the assembled rim body.

As mentioned, the adhesive holdfast region may include a tab configured to be grasped by a subject applying or removing the device. Further, the rim body (e.g., the first and second rim bodies) may be made of medical grade plastic such as Acrylonitrile Butadiene Styrene (ABS), polypropylene, polyethylene, polycarbonate, polyurethane and polyetheretherketone. The airflow resistor may be a flap valve and the flap may be made of silicone or thermoplastic urethane. The adhesive holdfast may include an adhesive substrate made of silicone, polyurethane or polyethylene. The biocompatible adhesive may be a hydrocolloid or an acrylic material.

Also described herein are adhesive nasal device adapted to be secured (e.g., removably secured) in communication with one or both of a subject's nasal cavities that include an inner rim body having at least one airflow passage therethrough, an outer rim body having at least on airflow passage therethrough (wherein the outer rim body is attached to the inner rim body so that the airflow passage of the inner rim body is continuous with the airflow passage of the outer rim body), an airflow resistor secured between the inner and outer rim regions within the airflow passage, and an adhesive holdfast secured between the outer and inner rim body.

Also described herein are methods of treating a subject that include the steps of removing a protective cover from an adhesive holdfast region of an adhesive nasal device (wherein the adhesive nasal device comprises a rim body having a passageway therethrough, an airflow resistor in communication with the passageway of the rim body, and a flexible, adhesive holdfast layer extending outward from the periphery of the rim body), and applying the adhesive nasal device to a subject's nasal cavity (or both nasal cavities). In any of the variations described herein, the adhesive holdfast may comprise a layer of adhesive substrate including a biocompatible adhesive. This adhesive holdfast may extend so that the skin-contacting surface of the adhesive holdfast is substantially perpendicular from the axis of the passageway through the rim body. In some variations, the skin-contacting surface (e.g., the surface configured to adhesively secure the device to the user) is off axis of an airflow passageway through the rim body.

Also described are methods of making an adhesive nasal device comprising, the method including the steps of placing an airflow resistor between a first rim body and a second rim body, placing an adhesive holdfast between the first rim body and the second rim body, and securing the first rim body to the second rim body to secure the airflow resistor and the adhesive holdfast therebetween.

Also described are methods of making an adhesive nasal device, the method including the steps of forming a rim body having a passageway therethrough by securing a first and second rim body region to each other, and securing an airflow resistor within the airflow passageway, and securing an adhesive holdfast to the rim body.

INCORPORATION BY REFERENCE

All publications, patents, and patent applications mentioned in this specification are herein incorporated by reference in their entirety to the same extent as if each individual publication or patent application was specifically and individually indicated to be incorporated by reference in its entirety.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings.

FIGS. 5A and 5B are top and bottom perspective views of an inner rim body region similar to the variation shown in FIG. 4.

DETAILED DESCRIPTION OF THE INVENTION

Figure 1A:
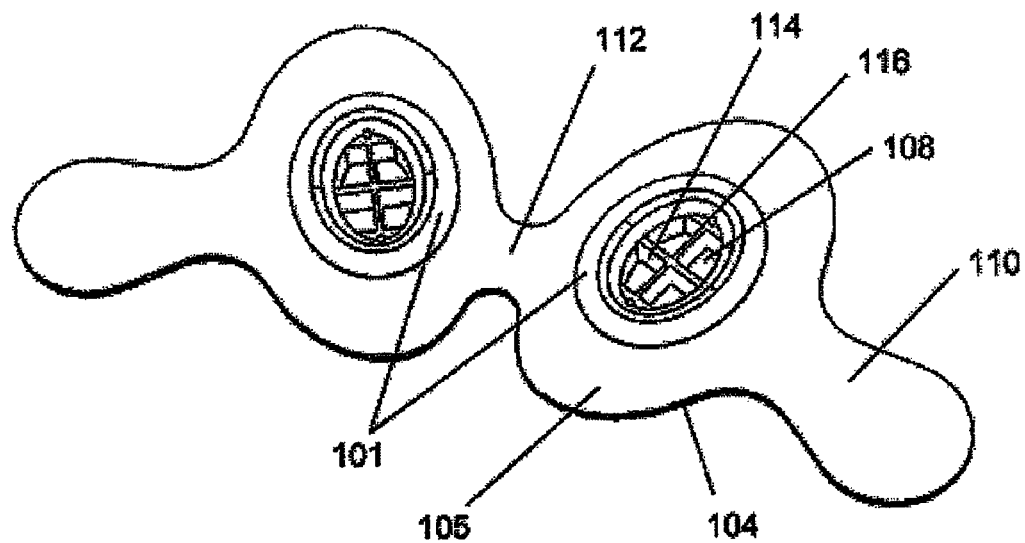
FIGS. 1A and 1B are a bottom and top perspective views, respectively, of one variation of an adhesive nasal device as described herein.

An adhesive nasal respiratory device is one variation of a general nasal respiratory device in which an adhesive holdfast region is used to secure the device in fluid communication with one or both of a subject's nostrils. A nasal respiratory device, including an adhesive respiratory device, may be used for creating positive end expiratory pressure ("PEEP") or expiratory positive airway pressure ("EPAP") during respiration in a subject wearing the device. The adhesive respiratory devices and methods described herein may be useful to treat a variety of medical disease states, and may also be useful for non-therapeutic purposes. The devices and methods described herein are not limited to the particular embodiments described. Variations of the particular embodiments described may be made and still fall within the scope of the disclosure. It is also to be understood that the examples and particular embodiments described are not intended to be limiting.

As used herein, an adhesive nasal device may be configured to fit in, at least partly in, over, at least partly over and/or around a single nostril (e.g., a "single-nostril nasal device"), or in, at least partly in, over, at least partly over and/or around both nostrils ("whole-nose nasal device"). Both single-nostril nasal devices and whole-nose nasal devices may be referred to herein as "adhesive nasal devices," and unless the context indicates otherwise, any of the features described for single-nostril nasal devices may be used with whole-nose nasal devices, and vice-versa. In some variations, an adhesive nasal device is formed from two single-nostril nasal devices that are connected to form a unitary adhesive nasal device that can be applied to the subject's nasal cavity. Single-nostril nasal devices may be connected by a bridge (or bridge region, which may also be referred to as a connector). The bridge may be movable (e.g., flexible), so that the adhesive nasal device may be adjusted to fit a variety of physiognomies. The bridge may be integral to the nasal devices. Examples of the bridge region are described in more detail below. In some variations, single-nostril nasal devices are used that are not connected by a bridge, but each include an adhesive region, so that (when worn by a user) the adhesive holdfast regions may overlap on the subject's nose, thus forming a bridge which may facilitate removal.

As used in this specification, the singular forms "a," "an," and "the" include plural reference unless the context clearly dictates otherwise. The following descriptions including various design parameters or goals, and methods and devices which fit the design parameters or goals. It should be understood that the devices and methods described herein (and recited by any claims) are not limited to any particular theory of operation.

In general, an adhesive nasal device includes a rim body having one or more passageways through which air may pass to enter or exit a nostril; an adhesive holdfast for securing the device to, over, and/or within a subject's nostril; and an airflow resistor (e.g., a valve or valves) for regulating the passage of air through the passageway(s). As will be apparent from the figures, many of these devices may be removable and insertable by user without special tools.

In operation, an adhesive nasal device is placed in communication with one or both of a subject's nostrils to modify the flow of air through the subject's nasal cavity or cavities. Thus, the respiratory devices described herein include one or more airflow resistors for modifying the flow of air through the nose in at least one direction. In most variations of the devices described herein, the airflow resistor is configured to occlude airflow through a passageway in one direction more than it occludes airflow in the opposite direction. For example, an airflow resistor may occlude airflow during exhalation more than inhalation. Examples of airflow resistors are described below, but may include valves airflow resistors (e.g., flap valves, hinge-less valves, balloon valves, stepper valves, ball valves, etc.) or the like.

To use many of the adhesive nasal devices described herein, a subject first applies an adhesive respiratory device over his nasal cavity (or nasal cavities) by removing a protective cover material from an external adhesive region of the device (the holdfast) and applying gentle pressure to cause the device to adhere around the nostrils. In this way, the device may be seated around the nasal orifice (and may intrude at least partly into the nostrils) and form at least a partial seal between the nostrils and the device so that the majority of flow into and out of the nostrils passes through the passageways of the nasal device. Once the device is applied to the subject's nose, respiration through the nostrils may be regulated. In some variations, the adhesive nasal device is configured so that there is only nominal resistance through the nasal device during inhalation, but increased resistance to airflow during exhalation. During inhalation in a subject wearing such a device, the subject may breathe through the nose (and thus through the nasal device). During exhalation, the adhesive nasal device provides greater resistance to airflow through the device. Thus, the subject may still breathe predominantly though the nose (and the nasal device) during exhalation, but may also breathe at least partly through the mouth.

It may also be beneficial for a subject to wear a nasal respiratory device over an extended period of time (e.g., during a period of sleep). Described below are variations of adhesive nasal devices that are comfortable to wear, and secure in or over the subject's nose or nasal passages. In some variations, a grip (e.g., a tab, handle, strap, or other additional interface region) may be included to help secure the device to the subject's nostril, nose or face, and may additionally or alternatively be helpful in positioning or manipulating (e.g., gripping) the device, particularly when it is being applied. This additional interface region may be formed of the same material as the adhesive holdfast region, or it may be a separate region, as described in more detail below.

In some versions of the device, the adhesive holdfast in combination with a rim body (with or without an additional adaptor to connect with standard PAP tubing) may be used with a positive airway pressure machine (CPAP, VPAP, bi-level PAP for example) and related tubing that is well known to those skilled in the art. Headgear and/or straps may still be required to help affix the tubing to a subject's head or face.

Figure 1B:
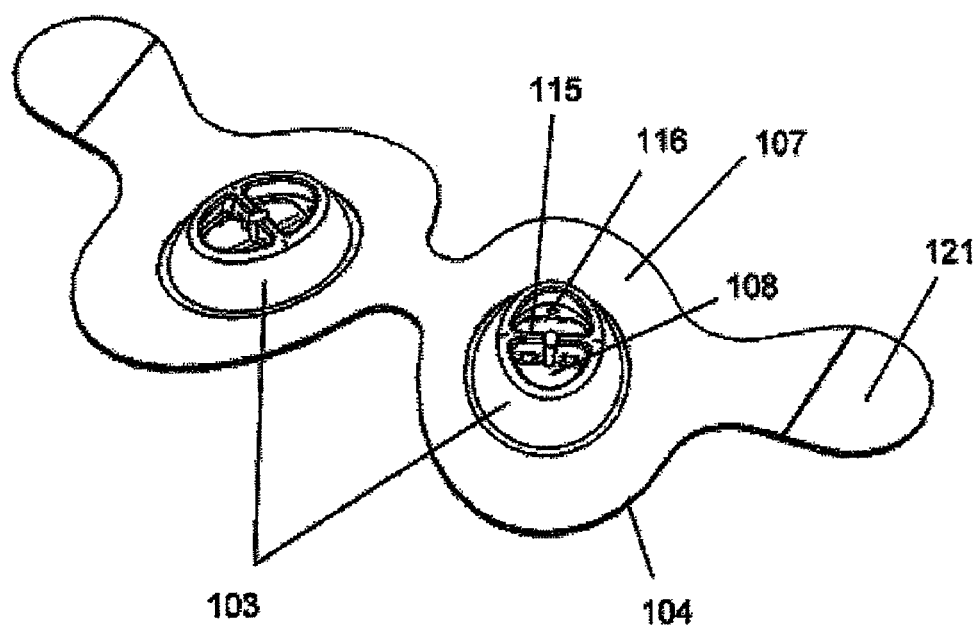
Figure 2:
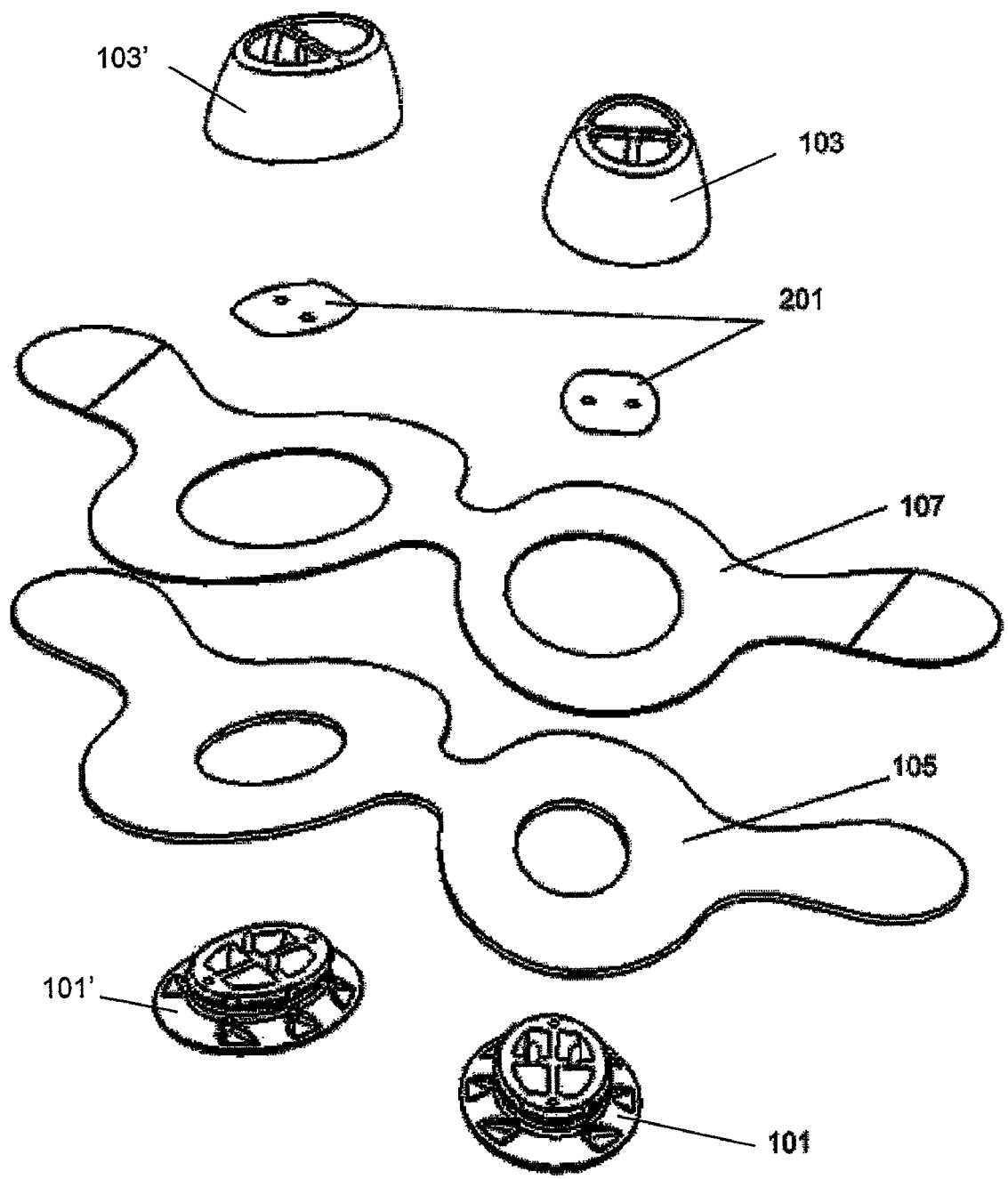
FIG. 2 is an exploded view of the adhesive nasal device of FIG. 1.
Figure 3:
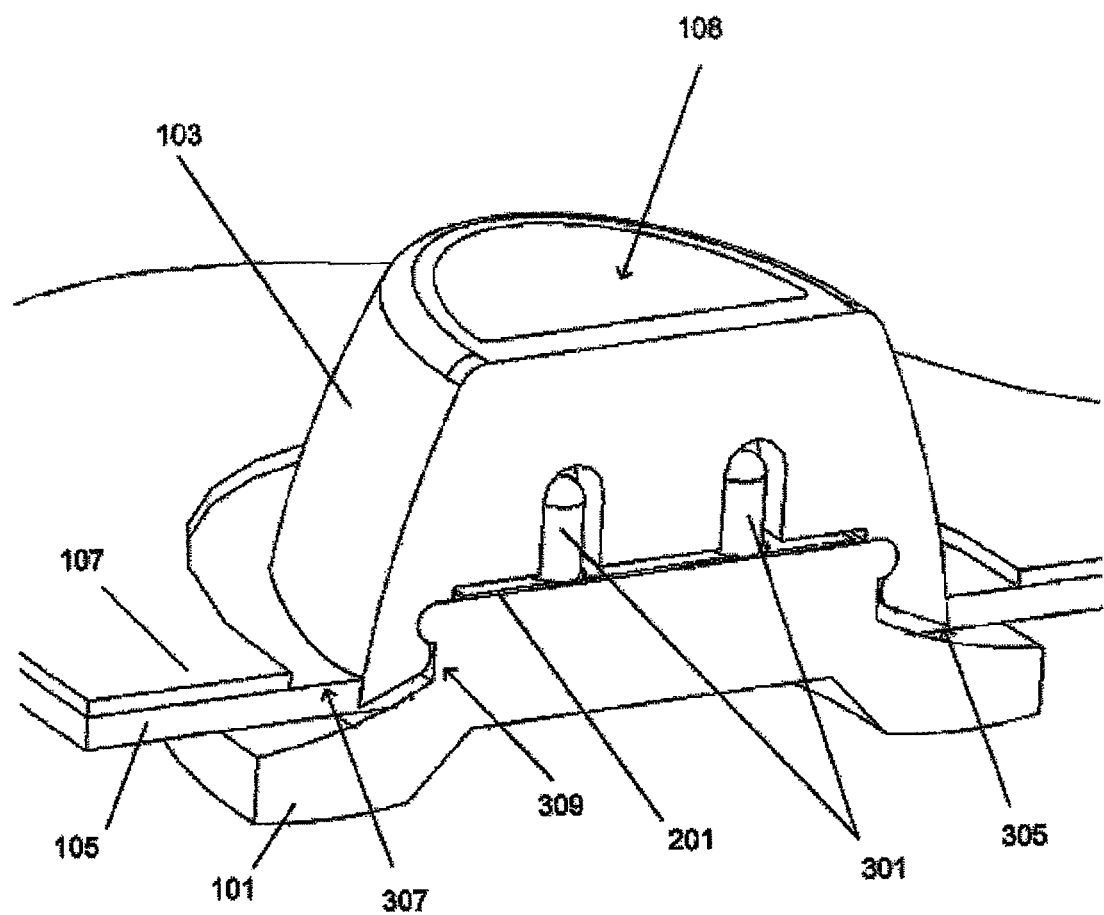
FIG. 3 is a cross-section through another variation of an adhesive nasal device.

FIGS. 1A and 1B show perspective view of one exemplary variation of an adhesive nasal device as described herein, FIG. 2 shows an exploded view of the same variation, and FIG. 3 shows a cross-section through this variation. FIG. 1A shows a perspective view of an adhesive nasal device, looking at the "outer" side of the device, which is configured to be the side facing away from the subject's nose when worn. The device shown in FIG. 1A includes two single-nostril rim bodies 101 and a single adhesive holdfast 104. The holdfast 104 (which, in this variation, secures to the subject) is shown as a layered structure including a backing or adhesive substrate 105. This backing may act as a substrate for an adhesive material, or it may itself be adhesive. The holdfast 104 may have different regions, including two peri-nasal regions surrounding the rim bodies 101. Each rim body has at least one passageway 108 for airflow therethrough. The adhesive holdfast also includes two tabs or grip regions 110 that may make the device easier to grasp, apply, and remove. A bridge region 112 is also shown. In this example, the bridge region is part of the adhesive holdfast (e.g., is formed by the same substrate of the adhesive holdfast) and connects the peri-nasal regions. Although the tab and bridge regions are shown as being formed as part of (integral with) the holdfast material, these regions may also be formed separately, and may be made of different materials.

The rim body regions 101 shown in the exemplary device of FIG. 1A correspond to outer rim body regions which each encompass a passageway 108. As described below, these first (e.g., outer) rim body regions may mate with a second (e.g., inner) rim body regions to form the rim body region(s) of the device that includes the passageway 108. These passageways in this example are interrupted by crossing support members 114 (e.g., cross-beams or cross-struts) that may partly support or restrict movement of the airflow restrictor. In addition, each rim body region 101 includes two leak pathways 116, through which air may pass even when the passageway through the device is otherwise blocked by the airflow resistors. The leak pathways 116 are shown here as small openings at the narrow ends of the oval-shaped outer rim body region. The rim body region may also be referred to as 'rim' or 'scaffold' regions of the device.

FIG. 1B shows a perspective view of the opposite side of the adhesive nasal device shown in FIG. 1A, the "inner side" of the device. The inner side of the device faces the subject, and a portion of this side of the device may contact the subject. This side of the device, and particularly adhesive holdfast of the device, includes an adhesive (which may be covered by a protective cover 107) forming part of the holdfast 104. In some variations, the entire skin-facing side of the holdfast 104 includes an adhesive on the surface, although in some variations, only a portion of this region includes adhesive. The adhesive may be a distinct layer of the holdfast (e.g., it may be layered on top of an adhesive substrate), or it may be an integral part of the holdfast (e.g., the adhesive substrate may be made of an adhesive material). In some variations, adhesive may be separately added to the device (e.g., the holdfast region) before use. The adhesive material may be covered by a removable protective cover or liner 107 to prevent the adhesive from sticking to surfaces until after the liner is removed. In FIG. 1B, the protective cover 107 covers the entire skin-facing surface of the holdfast. The device may be applied by first removing the liner. For example, the liner may be peeled off, to expose the adhesive. In some variations, the liner protecting the adhesive may be partially removed. For example, the tab region 121 of the device may include a separate (or additional) liner that remains over the tab region when other liner regions are removed. This may allow the device to be held by the tab region without having it adhere to the skin. After removing the cover, or a part of the cover, the device may be positioned and adhered to the subject's skin around the nasal cavity, so that the passageways through the rim body are aligned with the openings of the subject's nasal cavities. In some variations, an additional adhesive cover region (e.g., the protective cover region over the tabs 121) can then be removed to secure the device to the rest of the subject's nose. The adhesive cover may include a fold (or crimp, crease, lip, or the like) that helps to remove the protective cover from the adhesive.

The second, or inner, rim body region 103 shown in the exemplary device of FIG. 1B is shaped with an inwardly-tapering edge, so that it may fit at least slightly within the opening of the subject's nostril when a subject wears the device. The inner rim body includes one or more passageways 108 that correspond with the passageways 108 shown in FIG. 1A. Similarly, the leak pathways pass completely through the rim body (both inner and outer bodies). The tapering external walls of the inner rim body region(s) shown in FIG. 1B are shown as smooth, and may also include an additional material (e.g., an auxiliary holdfast material) for securing them in the subject's nostrils, or for cushioning them to prevent injury or discomfort. These surfaces may also be more or less angled, in order to facilitate comfort when the adhesive nasal device is worn in the subject's nose. A cross bar (hinge region 115) may also be provided as part of the inner rim body. The inner rim body 103 may extend some distance above the peri-nasal annular region of the holdfast, as shown in FIG. 1B. This distance may be sufficient to prevent any portion of the airflow resistor (e.g., a flap portion of a flap valve) from extending out of the device and into the nasal cavity where is might contact body tissues.

FIG. 2 shows an exploded view the adhesive nasal device shown in FIGS. 1A and 1B, from the perspective of the inner side of the device (similar to the perspective shown in FIG. 1B). This exploded view shows five components of the device: a first 103 and third 103' (e.g., inner) rim body regions, a second 101 and fourth 101' (e.g., outer) rim body regions, an airflow resistor (in this example, flap valve 201), an adhesive substrate (with adhesive) 105 and a protective cover 107 that fits over the adhesive layer. As shown in the exploded view, the first 103 and second 101 rim body regions can be clamped together to secure the layered holdfast (including the adhesive substrate 105 and adhesive) and the airflow resistor 201 between the two rim body pieces 101, 103. The protective cover 107 in this example is not clamped between the inner and outer rim body regions. This is shown in detail in the cross-sectional view shown in FIG. 3.

FIG. 3 shows a cross-section though one of the two regions shown in FIGS. 1A, 1B and 2. The cross-section is taken through the middle of one of the two rim bodies (through the short axis of the oval-shaped rim body), directly through the hinge region 115 (refer to FIG. 1B). The airflow resistor in this exemplary device is a flap valve type airflow resistor, having a flexible flap valve 201 that is secured between the inner rim body region 103 and the outer rim body region 101, as shown in FIG. 3. The flap valve 201 is secured both by the compression of the first 103 and second 101 rim body regions and by the two posts 301 that pass through openings in the flap valve 201. In FIG. 3, the posts 301 project upwards from the outer rim body region 101. The outer 101 and inner 103 rim body regions may be secured together by a friction fitting (e.g., a press fit such as a snap-fit), indicated by the arrow labeled 309. Thus, the inner and outer rim body regions may mate together to form the rim body.

In FIG. 3 the holdfast region (including the adhesive and adhesive substrate 105) is secured between the first (inner) 103 and second (outer) 101 rim body regions and is held in place between the two, as shown. In this example, the inner rim body region includes an edge or annular region 305 that presses down into the holdfast (e.g., adhesive substrate 105) and secures the holdfast against the upper rim body region 103. In some variations, the rim body regions may include posts, grips, or mating regions that secure the holdfast between the inner and outer rim body regions. The protective cover 107 covers the adhesive side of the substrate 105 to protect the adhesive until the cover is removed and the device is applied to a subject.

In this example, the adhesive holdfast is a layered structure that includes a substrate layer, an adhesive coating, and a protective cover for protecting the adhesive coating. Thus, the adhesive holdfast is a relatively flat structure that surrounds and projects from the rim body approximately perpendicularly from the passageway(s) for airflow through the rim body.

The adhesive nasal device illustrated in FIGS. 1A through 3 may be worn over a subject's nose by securing the adhesive surface of the holdfast against the subject's nose (e.g., to the skin around and/or just within the opening of the nasal orifice) so that the rim body regions cover the nostrils. The device may effectively form a complete or partial seal around the subject's nasal openings so that airflow into and out of the nose passes through the adhesive nasal device. In particular, airflow through the device passes through the passageways of the nasal device, including the airflow passageways that are regulated by airflow resistors, and any leak passageways (e.g., which are not regulated by an airflow resistor).

FIGS. 1A-3 show one embodiment of the invention. Additional embodiments are described below with reference to the different components that may be included as part of an adhesive nasal device. The description below is broken into sections that are intended only to help organize the description, and do not necessarily indicate organization of an adhesive nasal device. It should be understood that an adhesive nasal respiratory device within the scope of the invention described herein may include additional features, or may not include some of the features, or may include alternative embodiments of some or all of the features.

Rim Body

The rim body region of the adhesive nasal respiratory devices typically includes an airflow passageway, and a region of attachment to a holdfast. The rim body may be formed of a relatively rigid or more flexible material that provides support for the passageway or passageways there through. The rim body may be formed of two or more interlocking parts, however in some variations the rim body region may be made of a single component. For example, the rim body may be formed by joining a first rim body and a second rim body, as illustrated above. The shape of the rim body region may be adapted both to support a passageway and to fit a subject's nose comfortably. Furthermore, the rim body region may be configured to hold or secure other components of the device such as the holdfast and/or airflow resistor and/or a bridge or other means that connects one respiratory device to another.

The rim body may also be referred to as a modular rim body, referring to rim bodies that are formed of two or more parts or sections. In some variations, modular rim bodies are formed of rim body regions that engage with each other (either directly or indirectly) to form the assembled modular rim body. For example, a first rim body region may engage with a second rim body region to secure a holdfast and/or an airflow resistor between the first rim body region and the second rim body region. Thus, additional components of the nasal device may be secured to the modular rim body region (including components that do not form part of the rim body or internal passageway(s)).

An adhesive nasal respiratory device may have a single rim body (though it may be formed of different parts) configured as a single-nostril device, or it may have two rim body regions that are each configured to be used over or at least partially within one of a user's nostrils. In some variations, a single rim body region is configured to span both nostrils, or to be connected in communication with both nostrils.

The rim body (or rim body region) of the adhesive nasal device is generally configured to fit over, within or partially within or be positioned in close proximity to a subject's nasal cavity. For example, the rim body may be small enough to comfortably fit within a broad range of nasal cavity sizes. The rim body may have a central axis that aligns with the direction of airflow into or out of the nasal cavity. The outer perimeter of the rim body perpendicular to this central axis may be generally circular, oval, or lobular in partial cross-section, at various points along the central axis.

Figure 4A:
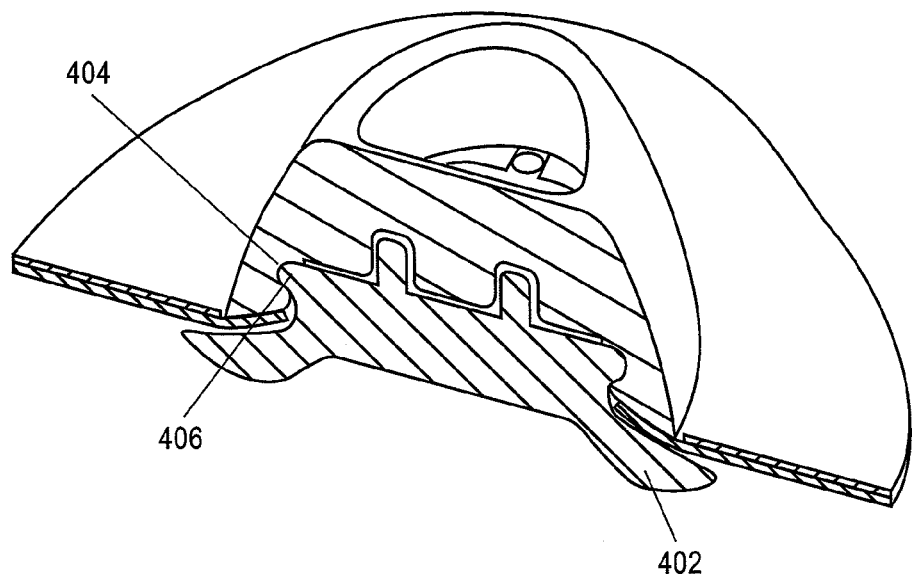
FIGS. 4A and 4B are cross-sectional views of one variation of a rim body as described herein.
Figure 4B:
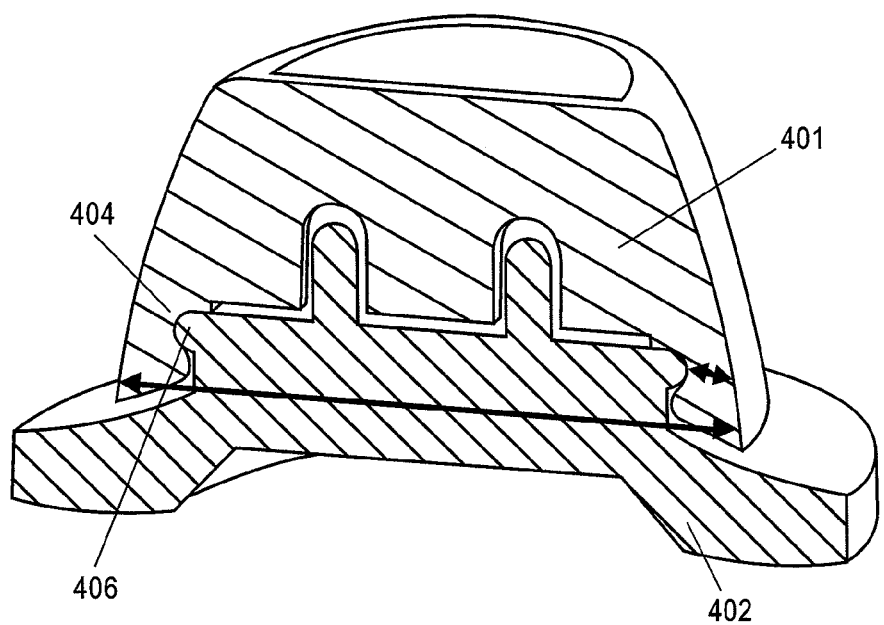

As mentioned above, the rim body may be formed from two or more parts that combine to form the entire rim body. For example, the rim body may comprise an inner and an outer rim body region that interlock or mate with each other to form the rim body. FIG. 4 shows a cross-sectional view of one variation of a rim body that has two interlocking subparts, and an inner 401 (or first) rim body region and an outer (or second) rim body region 402. The inner rim body region 401 (or first rim body region) may be configured to fit at least partially within the subject's nostril. For example, the outer perimeter of the inner rim body region may be smooth, and may be shaped to fit within the nasal passageway with only minimal (if any) contact with the sides of the subject's nostril passageway. In some variations, the curvature of the outer perimeter at least partially conforms to the curvature of a subject's inner nostril passageway. For example, one side of the inner rim body region may be less curved than the other side (e.g., the side facing the subject's septum when the device is worn). In this instance, "side" refers to the external surface of the inner rim body region substantially perpendicular to the central axis. Although this first rim body region is referred to as an 'inner' rim body region, it should be clear that some variations of the rim body are not configured to project into a nasal passage, but may be completely outside of the nose, or may not project substantially into the nasal passage when worn by the user.

FIGS. 5A and 5B show top and bottom perspective views of an inner rim body region similar to the variation shown in FIG. 4. The inner rim body region includes a passage 510 that is divided by a crossbar 520. As described in more detail below, this crossbar may support or secure the airflow resistor (e.g., flap valve) within the passageway. In addition, the crossbar may provide additional structural support for the rim body. For example, the cross bar may act as a flap valve limiter to prevent the flap valve from opening in an undesirable direction (e.g., during expiration). In general, a separate or additional flap valve limiter (e.g., mesh, bar, etc.) may be used as part of the airflow resistor in devices including a flap valve.

Figure 6A:
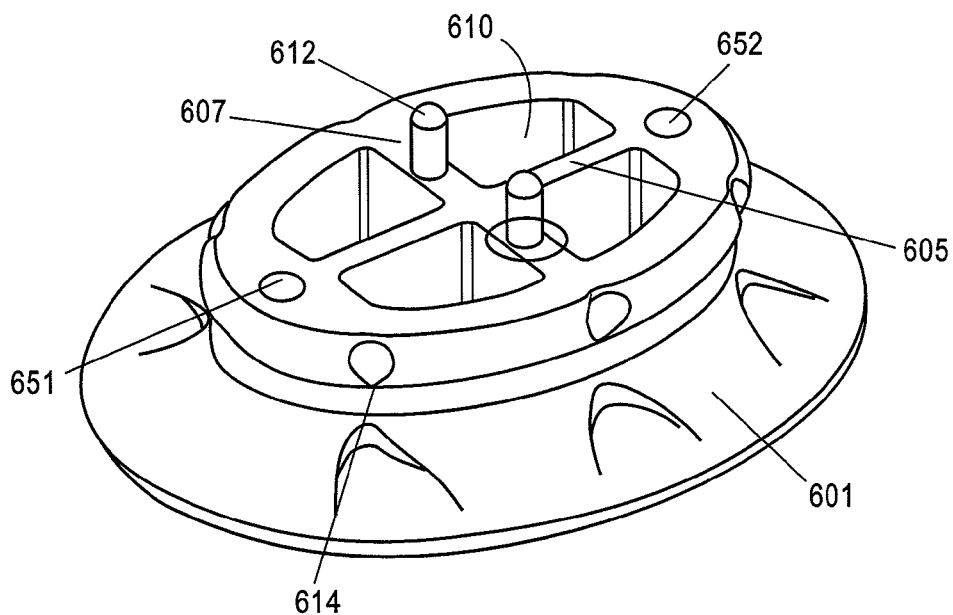
FIGS. 6A and 6B are top and bottom perspective views of one variation of an outer rim body, as described herein.
Figure 6B:
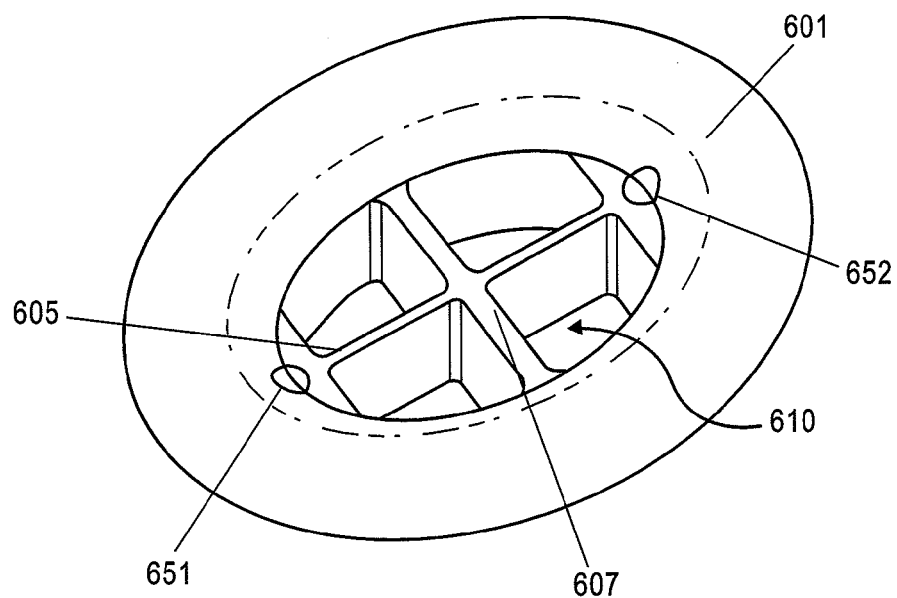

The bottom perspective view of the inner rim body shown in FIG. 5B illustrates the annular edge of the inner rim body 507 that is configured to mate with the annular edge of the outer rim body (shown in FIGS. 6A and 6B). This annular edge region includes six protrusions 505 that may mate with recessed regions in the outer rim body, and may also help secure the holdfast region between the inner body rim and outer body rim. Thus, these protrusions may be sharp or dull, and may pierce or simply compress the holdfast.

An outer 402 rim body region may be configured to fit substantially outside of a subject's nostril. In some variations, the outer rim body region may be configured to fit within the subject's nostril. In FIG. 4, the outer rim body region has a flanged outer edge (having a larger diameter than the inner rim body region). This flanged edge forms a lip or rim which may both help prevent the device from entering the nasal passage, in and/or may provide a surface on which the holdfast may be supported.

FIGS. 6A and 6B show top and bottom perspective views of one variation of an outer rim body 601 that is configured to mate with an inner rim body similar to that shown in FIGS. 5A and 5B. The outer rim body includes a passageway 610 that is divided into four sections by the support beams 605, 607 that may be used to support a portion of the airflow resistor (e.g., a flap valve). In this variation, the outer rim body also includes two posts 612 that may also be used to secure and position the flap region of a flap valve, as described in greater detail below. Recessed regions 614 on the annulus of the outer rim body may mate with protrusions in the inner rim body, as described above. FIG. 6B also illustrates leak pathways 651, 652. An adhesive nasal device may be configured to include leak paths that allow a basal level of airflow through them even when the airflow resistor otherwise inhibits the passage of air. For example, the a flap valve may be shaped so that when it is secured between the inner and outer body rims, and allowed to close, the flap valve does not cover the two leak paths 601, 602. In some variations, the flap may partially or completely cover the leak paths. In some variations, no leak path is included. In some variations, a leak path is included through the airflow resistor (e.g., as one or more holes through a flap valve).

The outer 402 (or second) rim body region may connect with the first rim body region to form the entire rim body region, as shown in FIG. 4. The outer and inner rim body regions may connect by friction fitting, interlocking, bonding (e.g., welding), gluing or the like, including combinations. For example, in FIG. 4, the inner rim body 401 press-fits to the outer rim body 402. In this variation, the inner rim body 401 includes an annular recessed region 404 and an annular protruding region that can mate with an annular protruding region 406 and an annular recessed region on the outer rim body. In some variations, the inner and outer rim body regions may be secured together by an adhesive, or by welding or otherwise bonding to two regions in a junction region of the inner and outer rim body regions. In some variations the outer and inner rim body regions may include engagement regions such as posts or snaps.

The rim body may be made of any appropriate material, including, but not limited to metals, plastics, rubbers, ceramics, wood, chrome, or combinations thereof. Other materials may include acrylics, latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device which may contact a user, including the rim body. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dinethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Teflon, Mylar, PFA, LDPE, Hytrel, HDPE and polyester may also find use in any components of the devices.

Materials that are relatively stiff may be particularly useful. In addition, materials that are biocompatible and/or sterilizable may also be preferred, for example, medical grade plastics such as Acrylonitrile Butadiene Styrene (ABS), latex, polypropylene, polycarbonate, and polyetheretherketone. The forgoing materials are intended as illustrations only.

Figure 7A:
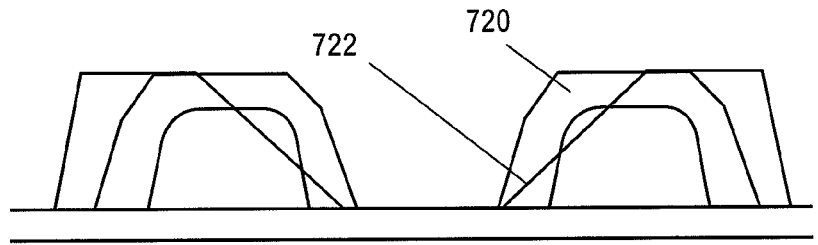
FIGS. 7A-7C are variations of adhesive nasal devices.
Figure 7B:
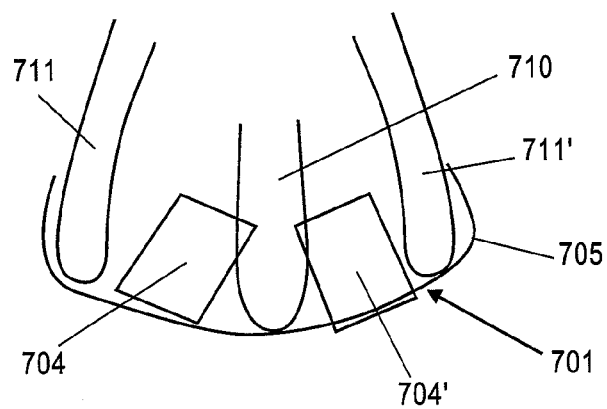
Figure 7C:
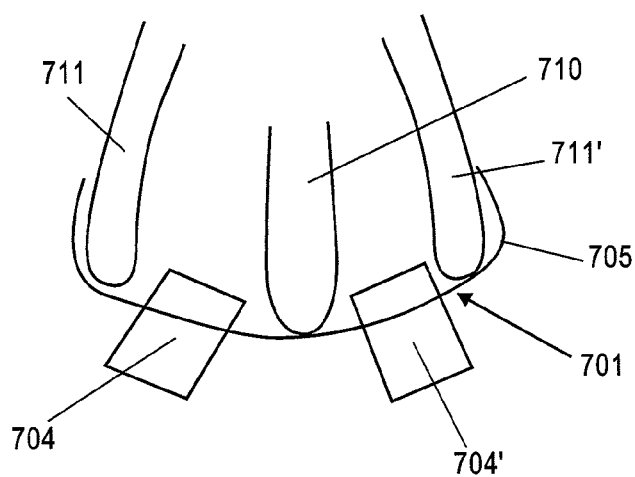

As mentioned above, the adhesive nasal devices (particularly the rim body region) may be configured to be comfortably worn by a user. For example, the devices may be configured so that the rim bodies do not apply significant pressure to the septal region (or other regions) of a subject's nose when worn. FIG. 7B shows one variation of an adhesive nasal device in which the nasal device impinges on the septal region of a subject's nose. FIG. 7A shows a cross-section through the subject's nose and one variation of an adhesive nasal device 701. The nasal device includes two rim bodies 704, 704'. In this variation of the nasal device 701, the rim bodies are attached to an adhesive holdfast 705 so that they bodies extend substantially into the nasal passages. The device is applied to the nose such that the holdfast region secures the device across the nasal passages, and seals around the edges of the nostrils. When this device 701 is worn, the distal portion of the rim bodies may contact the septum 710, as shown. In practice, this contact may be irritating, particularly if the rim body 704, 704' is made of a stiff material or is sharp. FIG. 7C illustrates another variation of an adhesive nasal device in which the rim bodies 704, 704' do not project as far into the nasal passages, and are therefore less likely to contact the septum. For example, the rim body may be made of a first (inner) rim body and a second (outer) rim body, where the inner rim body is relatively short (and therefore does not project far into the nose) or is shaped so as to avoid the septum, as shown in FIG. 7A, 722.

FIG. 7A shows another possible variation, in which the rim body is configured so that it is less likely to contact the septal region of the nose. FIG. 7A shows an overlay of two cross-sectional profiles through adhesive nasal devices. The first device 720 has a profile in which the rim body regions are relatively symmetric about a central axis. The cross-section of the second device 722 has a cross-sectional profile in which the portion of the adhesive nasal device nearest the septal region (i.e. the central region of the device) is angled so that when the device is worn, it is less likely to contact the septal region of the nose.

As described above, the rim body may form one or more passages through which air may flow. These passages may be of any appropriate size. For example, in some variations, a passage through the device has sufficient cross-sectional area (or the sum cross-sectional areas of all of the passages through the device) so that a comparable amount of air may flow through the passageway during at least part of the respiratory cycle (e.g., during inhalation) compared to the rate and/or amount of air that flows through a nostril without the device present. Thus, in some variations, the passageway through the device may have a cross-sectional area that is greater than approximately half of the cross-sectional area of the unobstructed nasal passage.

Figure 37A:
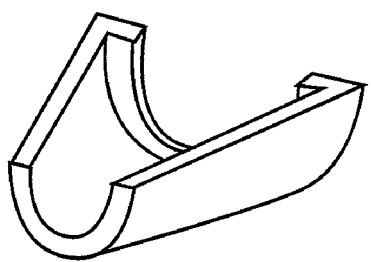
FIGS. 37A and 37B show side perspective views of a first and second rim body region, respectively.
Figure 37B:
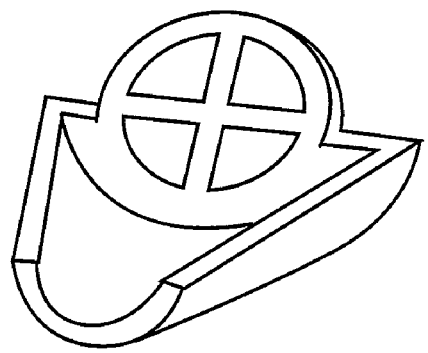

In addition to rim bodies formed from an inner rim body and an outer rim body, the devices described herein may be formed of two or more pieces oriented along the axis of the passageway, as illustrated in FIGS. 37A and 37B. FIG. 37A shows a first (e.g., lateral) and a second (e.g., medial) rim body region that may be combined to form a complete rim body. The airflow resistor and holdfast may also be affixed to the rim body, as described. In this example, the airflow resistor may be secured within the passageway formed by the first and second rim body before the first and second rim body regions are secured together.

The rim bodies described herein may also include an attachment site (or sites) for one or more airflow resistors.

Airflow Resistors

An airflow resistor is typically positioned in communication with at least one airflow passageway of the adhesive respiratory device, so that at least some of the air flowing through the passageway passes the airflow resistor. Thus, an airflow resistor modulates, alters, varies, or keeps constant the amount of resistance, the degree of airflow, or the pressure differential across the device or through a passageway in the device. Any appropriate airflow resistor may be used as part of the adhesive nasal devices described herein. In general, the airflow resistors described herein occlude airflow through a passageway in one direction more than they occlude airflow in the opposite direction. For example, an airflow resistor may occlude airflow during exhalation more than inhalation. Examples of airflow resistors are described below. In addition, examples of airflow resistors may be found in published U.S. patent application Ser. No. 11/298,640, titled "NASAL RESPIRATORY DEVICES" (filed Dec. 8, 2005), previously incorporated by reference in its entirety.

In some embodiments, the pressures created by the airflow resistor during exhalation may be between 0.01 and 100 cm of $H_2O$ measured at a flow rate of 100 ml/sec, and more preferably in between 0.5 and 25 cm of $H_2O$ measured at flow rate of 100 ml/sec.

Valve-type airflow resistors are particularly suitable. Examples of valves which may be used as airflow resistors include: flap valves (having one or more flaps); hingeless valves; stopper-type valves; membrane-type valves; ball valves; balloon-type valves; and the like. This list is not intended to be exhaustive, and other types of selective airflow resistors may be used. Moreover, multiple airflow resistors may also be used, which may include combinations of different types of airflow resistors. Flap valves are of particular interest. An airflow resistor configured as a flap valve typically includes a hinged or flexible flap (or flaps) that is movably secured so that the flap may open when air flows in one direction, and close when air flows in the opposite direction, or when air is not flowing. The opening and closing of the flap may allow air to flow across the valve, and thereby regulate airflow within a passageway in which the flap valve is positioned. In operation, the flap portion of the flap valve can thus selectively occlude airflow in one direction more than in other directions.

Valves configured for PEEP (positive end expiratory pressure) may also be used with any of the devices described herein. For example, a valve may be configured to have a non-zero threshold pressure for opening during expiration so that the valve is closed during expiration when the pressure across the valve is below the threshold pressure for opening during expiration, but the valve opens during expiration when the valve exceeds the threshold pressure for opening during expiration.

In some variations, a flap valve for use in an adhesive respiratory device includes a flap, one or more valve aligners (e.g., posts) that help secure the orientation of the valve and may help secure it in position, one or more valve supports (e.g., cross-bars) or valve limiters that prevent the valve from collapsing or opening when air flows in one direction through the passageway, and a valve seal region (e.g., a rim or ridge) against which the flap may be seated or abut when the valve is closed.

As mentioned above, one or more leak pathways may be included as part of an adhesive respiratory device. A leak pathway typically allows air to flow through the passageway even when the airflow resistor is closed. Thus a minimum basal level of airflow may be permitted through the passageway regardless of the state of the airflow resistor. In some variations, the leak pathway is a hole or unoccluded passage. A leak pathway may be a part of any region of the nasal respiratory device. For example a leak pathway may be part of the airflow resistor, part of the rim, part of the holdfast region, or part of the body of the nasal respiratory device (or some combination thereof). In some embodiments, the leak pathway may be present due to the intentional lack of perfect sealing or abutment of various components of the device (e.g., between the holdfast and the valve bodies or between the flap valve and the valve aligners, etc). A nasal respiratory device may be configured to have multiple leak pathways.

In some variations, the airflow resistor includes a flap valve. The flap of a flap valve may be made of a flexible material, or a hinged stiff material. In some variations, the flap comprises a thin sheet of flexible material that is shaped to fit within the passageway and at least partially occlude airflow through the passageway when the flap is seated against the valve seal region. The flap may also be shaped so that it does not occlude airflow through one or more leak pathways. FIGS. 8A-8F show different variations of flap valves. All of the flap valves shown in FIGS. 8A-8F are similarly shaped, and include two access regions 801, 801' through which two valve aligners (e.g., posts) can project to align the valves.

Figure 8A:
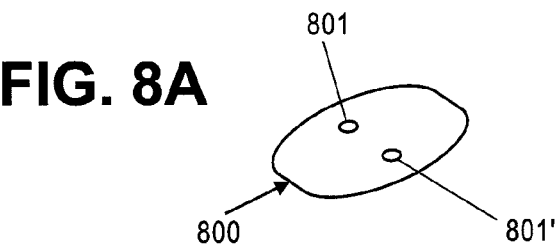
FIGS. 8A-8F are perspective views of a various flaps for flap valve devices as described herein.
Figure 8C:
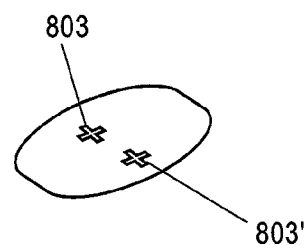
Figure 8B:
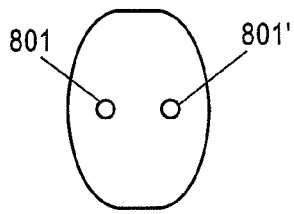

FIG. 8A shows a perspective view of a flap for a flap valve. The flap 800 is roughly oval shaped, as is better seen in the top view shown in FIG. 8B. The top and bottom regions of the flap shown in FIG. 8B are flattened or cut away. As will be apparent from some of the other figures, in which a similar flap valve is used, this cut away region may be positioned so that a leak pathway is not occluded by the flap when the flap is seated against the valve seal region (e.g., during expiration). The oval shape of the flap generally corresponds to an oval-shaped passageway through the nasal respiratory device. In some variations, leak pathways (e.g., holes, slits, etc.) may be present in the flap of the flap valve.

Figure 8D:
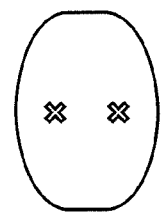
Figure 8E:
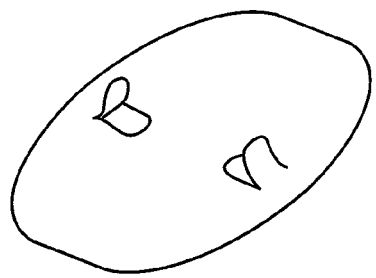
Figure 8F:

The access regions 801, 801' in FIGS. 8A and 8B are circular cut-outs through which the posts may pass to align and help secure the flap in position, as is apparent in other figures (e.g., FIGS. 2 and 3). In some variations it may be advantageous to use shapes other than holes for the access region. For example, cuts (such as L-shaped, I-shaped, C-shaped, and X-shaped) cuts may be used. Access regions formed of cuts may be advantageous over holes formed through the flap, because they do not produce 'chads' of material that must be removed from the airflow resistor. Such chads are potentially problematic because they may not fully separate from the flap during manufacture. FIGS. 8C and 8D show examples of flaps in which the access regions 803, 803' are formed by cutting an X-shape through the valve where the posts may be inserted. Similarly, FIGS. 8E and 8F show flaps in which the access regions are cut in different shapes so that the posts may pass through the access regions by pushing aside a portion of the flap, as shown in FIG. 8E.

Figure 38A:
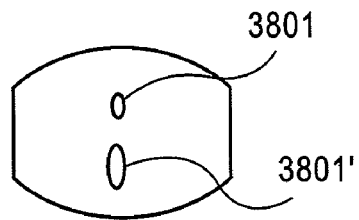
FIGS. 38A and 38B show two variations of flap valves that may be used with any of the devices described herein.
Figure 38B:
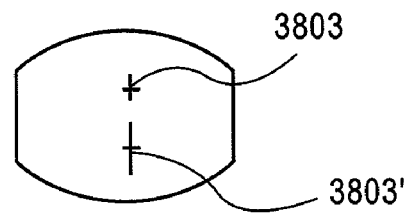

FIGS. 38A and 38B show two variations of flaps each having two access regions 3801, 3801', 3803, 3803' in which one of the access regions is larger than the other (and larger than the diameter of the posts to secure the flap. These variations may allow for enhanced size tolerance in manufacturing or assembling the flaps as part of a nasal respiratory device.

Figure 9:
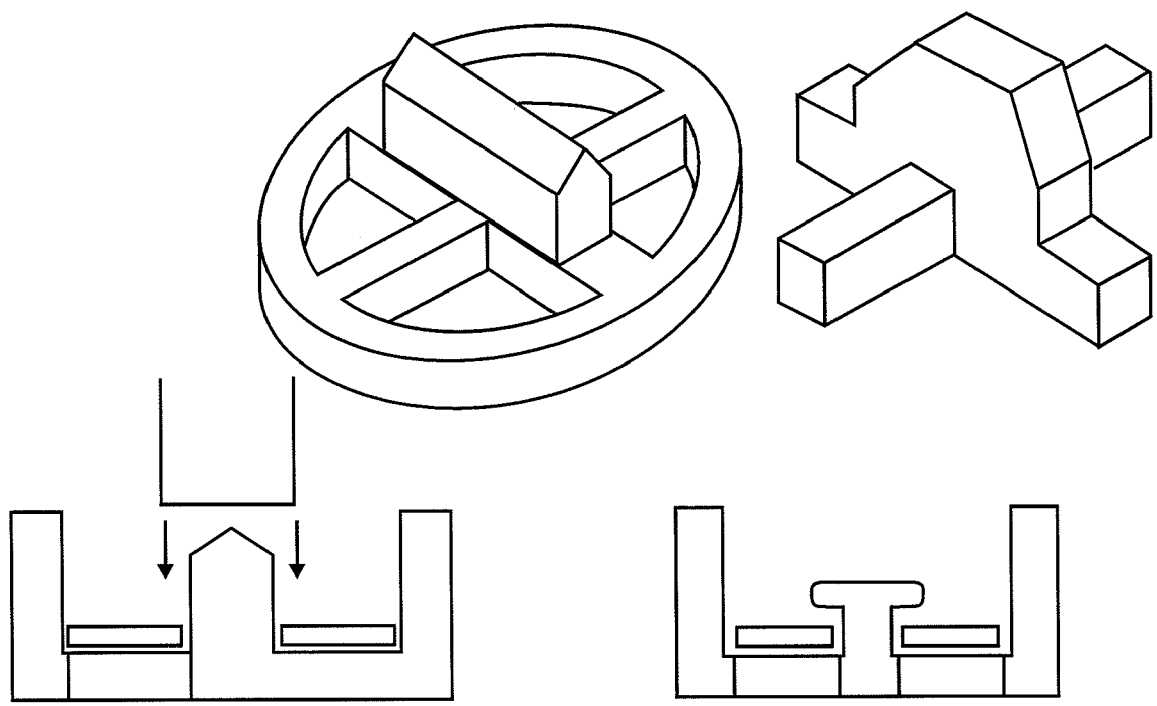
FIG. 9 is a flap valve secured to one portion of an adhesive nasal device, as described herein.

In many of the examples of airflow resistors shown as part of the adhesive nasal devices described herein (e.g., in FIGS. 1-4), the flap is secured between the first and second body regions, and aligned by two posts 301, as shown in FIG. 3. In this variation, the flap may flex inwards during inhalation, permitting airflow through the passageway, and the flap may be seated against the valve seal region (including the valve supports) 605 in the outer region during exhalation. In some variations, the flap may be secured within the passageway by staking, pinning, gluing or the like. For example, in FIG. 9, a heat stake is used to secure the flap to the base within the passageway of the nasal airflow resistor.

The flap may comprise any appropriate material, including those previously mentioned. For example, the flap may comprise polymeric materials, rubber (natural and synthetic), paper, fabric, or the like. For example, materials that may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins), and injection moldable materials such as polyether block amide (e.g., PEBAX®), and the like.

In some variations, the flap is made out of silicone or thermoplastic urethane. For example, the flap may be a thin and flexible piece of silicone. This flap may be any appropriate thickness that allow it to be flexible (e.g., to move from the open and closed positions). For example, the flap may comprise silicone that is between 0.0001 and 0.1 inches thick. In some embodiments, the silicone is approximately 0.002 inches thick.

In some variations, the flap is formed from a layer of material (e.g., a thin film such as a polyurethane film, etc.), and this same layer forms the adhesive substrate of the adhesive holdfast. Thus the same layer may be cut to form the flap valve leaflets. This layer of material may be secured between two or more regions forming a rim body so that the outer region of the layer extends from the valve body, and is coated with an adhesive, forming the adhesive holdfast.

Adhesive Holdfast

The adhesive nasal devices described herein may further comprise an adhesive holdfast for releasably securing the device in communication with a nasal cavity. The adhesive holdfast may include one or more adhesive surfaces that are suitable for use against a subject's body (e.g., skin and/or nasal cavity). Thus, the adhesive holdfast may include a biocompatible adhesive. The adhesive holdfast may facilitate the positioning and securing of the device in a desired location with respect to the subject's nose, such as over, partially over, partially within, or within (e.g., substantially within) a nostril. An adhesive holdfast may be configured to secure the device to any appropriate region of the subject's nose or nasal passage, including the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

In general, the adhesive holdfast is configured to be applied predominantly to the outside of the nose (e.g., the skin surrounding the nasal opening). In some versions, the holdfast may also secure a seal between the respiratory device and the nose, so that at least some of the air exchanged between the outside of the patient and the nostril must pass through the respiratory device. In some versions, the holdfast seals the device in communication with the nose completely, so that all air through the nostril (or nostrils) must be exchanged through the device. In some versions, the holdfast seal is incomplete, so that only some of the air exchanged between the patient and the external environment passes through the device. As used herein, "air" may be air from environment external to the patient, or it may be any respiratory gas (e.g., pure or mixed oxygen, $CO_2$, heliox, or other gas mixtures provided to the user).

The adhesive holdfast may be a flexible so that it conforms to the surface of the subject's skin, which may be relatively irregularly shaped, and may include hair and the like. In some variations, the adhesive holdfast is made of a porous material that permits the passage of water vapor, liquid water, sweat and/or oil, which may enhance comfort. The adhesive holdfast may also include a texture or patterned relief surface to enhance bonding to the subject's nose region.

The adhesive holdfast may be made of layers. For example, the adhesive holdfast may include a substrate layer to which a biocompatible adhesive is applied. The substrate is typically a flat (predominantly 2-sided) material that is flexible. An adhesive may be present on at least one surface of the substrate, allowing it to adhere to the subject's nasal region. In some variations, the substrate layer is itself adhesive without needing an additional adhesive. An additional protective cover may also be removably attached to the adhesive of the adhesive layer. The protective cover may allow the device (and particularly the adhesive holdfast) to be manipulated without inadvertently sticking the device to the fingers or other parts of the body and it may also prevent contamination of the adhesive. The protective cover may be a removable paper or other film that can be peeled off or otherwise removed to expose the adhesive. In some variations, the adhesive of the adhesive holdfast is activatable. For example, the adhesive becomes 'sticky' only after exposure to an activator (e.g., water, air, light, etc.).

Figure 10A:
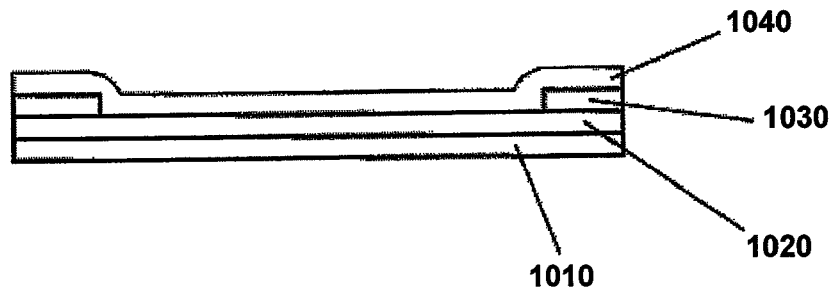
FIGS. 10A-10C show an adhesive holdfast region of an adhesive nasal device.
Figure 10B:
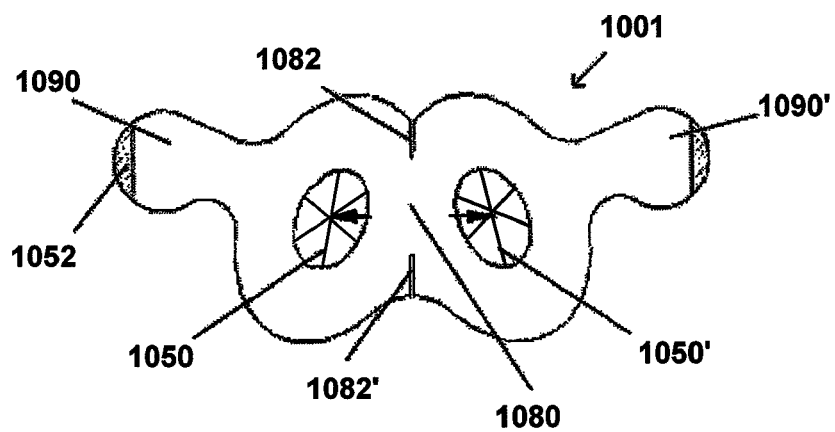

FIG. 10A illustrates a schematic of a cross-section through an adhesive holdfast having layers. In FIG. 10A, the adhesive holdfast includes a flexible substrate layer 1010, to which an adhesive 1020 is applied. A removable protective cover layer 1040 is placed on top of the adhesive 1020 to protect the adhesive. As shown in this cross-section, a separate piece of protective cover layer 1030 is placed at the right and left edges so that the larger section of removable liner overlaps with these edge pieces 1040. As seen in FIG. 10B, these edge pieces may help removal of the protective cover and may also help grasping the device after the larger piece of liner 1030 is removed, so that the adhesive does not stick to the finger. Once the device is positioned, these smaller tabs of protective cover 1040 can be peeled off as well. Thus, they may be folded or otherwise provided with a convenient way of grasping and removing them.

In some variations, a protective cover is not used. As already mentioned, in some variations, the substrate and adhesive are a single layer, so that the substrate comprises an adhesive material, or a material that can be activated to become adhesive.

The adhesive holdfast may comprise any appropriate material. Fore example, the adhesive substrate may be a biocompatible material such as silicone, polyethylene, or polyethylene foam. Other appropriate biocompatible materials may include some of the materials previously described, such as biocompatible polymers and/or elastomers. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Structurally, the substrate may be a film, foil, woven, non-woven, foam, or tissue material (e.g., poluelofin non-woven materials, polyurethane woven materials, polyethylene foams, polyurethane foams, polyurethane film, etc.).

In variations in which an adhesive is applied to the substrate, the adhesive may comprise a medical grade adhesive such as a hydrocolloid or an acrylic. Medical grade adhesives may include foamed adhesives, acrylic co-polymer adhesives, porous acrylics, synthetic rubber-based adhesives, silicone adhesive formulations (e.g., silicone gel adhesive), and absorbent hydrocolloids and hydrogels.

The removable protective cover layer may be made of any appropriate matter that may be released from the adhesive. For example, the protective cover material may comprise craft paper. In some variations, the protective cover includes a material having a wax or hydrophobic coating on one or both sides (particularly the side contacting the adhesive). For example, the protective cover material may comprise a polyethylene film, or polyethylene coated paper (e.g. Kraft paper). The protective cover may be any of the other materials described herein. Any of the materials commonly used in the manufacture of bandages (particularly disposable bandages such as Band-Aids™), ostomy kits, and wound care products may be used in any or all components of devices described herein.

In general, the adhesive holdfast may comprise any appropriate shape that allows the airflow passageway and airflow resistor to be positioned with respect to one or both nasal passages so that some (or most) of the airflow through the nasal passages must pass through the adhesive nasal device. In some variations, the adhesive holdfast attaches to the nose (or nasal passage) and forms a partial or complete seal therewith, thereby channeling airflow into or out of the nasal passageway through the device, and also securing the device in position. Thus, there are many designs that would achieve these criterions, many of which are described below.

For example, FIG. 10B shows one variation of the adhesive holdfast region of an adhesive nasal device. This variation is intended for use with a device having two rim body regions, each configured to operate with one of a subject's nasal passageways. As described above, an inner and outer rim body region (including a passageway and airflow resistor) may be secured to the openings 1050, 1050' shown in the adhesive holdfast region. These openings 1050, 1050' are configured so that they approximately align with a subject's nasal passageways. Thus, the adhesive holdfast region 1001 in this variation comprises two annular regions joined by bridge region 1080 that can adhere around the openings of the subject's nares. In addition, the holdfast 1001 shown in FIGS. 10A and 10B includes two additional tabs 1090, 1090' that may act as handles or grips. These regions may also adhere to the subject's nose and may wrap around the nares region and over to the side of the nose. This may also further secure the device in position.

Figure 10C:
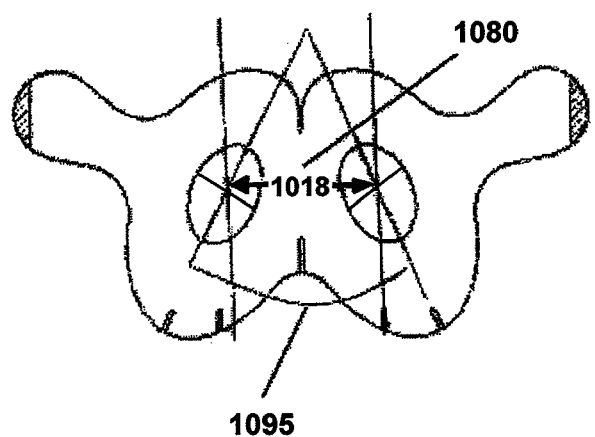

As mentioned above, openings 1050, 1050' are configured so that they approximately align with a subject's nasal passageways. In practice, the arrangement of nostril openings may be highly variable between individuals. FIG. 10C reflects two parameters of variation that may be addressed by the configuration of the adhesive holdfast. In FIG. 10C, arrows illustrate both the separation of the nostril openings 1018 and the tilt or angle of each nostril opening with respect to an imaginary line through the long axes of each nostril opening 1095. The adhesive holdfast may be configured to allow for variation of either or both of these parameters by allowing modification of the bridge region 1080. For example, in FIGS. 10B and 10C, the bridge region 1080 has been reduced in diameters by forming slits 1082, 1082' at either end. The narrowing of the bridge region 1080 may allow it to flex or bend (changing the angle of the nostril opening 1095).

Figure 11A:
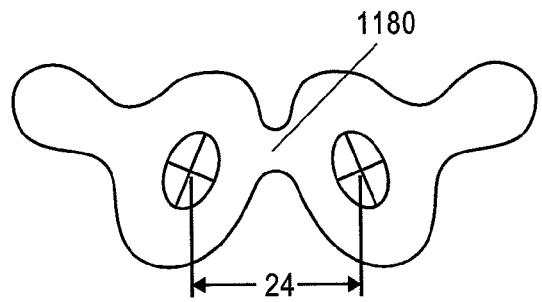
FIGS. 11A-11E are variations of the general shape of an adhesive holdfast region.
Figure 11B:
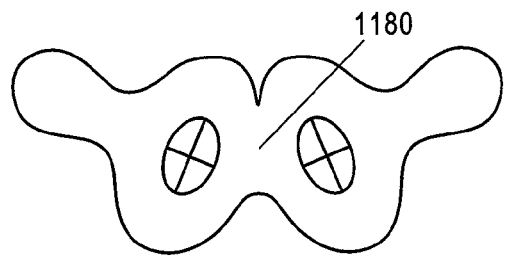
Figure 11C:
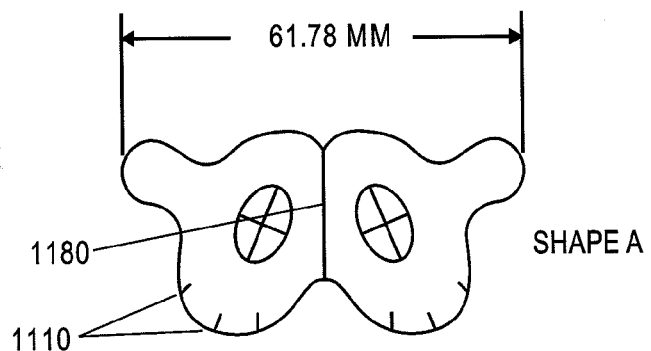
Figure 11D:
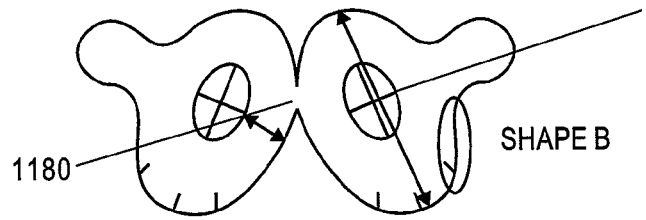
Figure 11E:
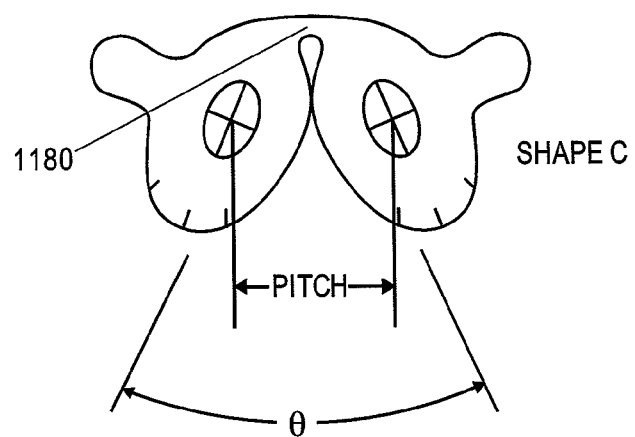

Other variations of the general shape of the adhesive holdfast region are shown in FIGS. 11A-11E. These variations also include tab or grip regions. In FIGS. 11A and 11B, the bridge regions 1180 of the adhesive holdfasts have different widths and lengths in the region between the two holdfast annular regions configured to surround the subject's nostrils. The thinner bridge 1180 region shown in FIG. 11A may be more easily bent than the wider bridge region 1180 of the variation in FIG. 11B. In addition, the location of the bridge region between the two annular regions may also be varied to achieve a sufficiently adjustable device. For example, the bridge region 1180 in FIG. 11C is located somewhat centrally between the annular regions, whereas the bridge region 1180 in FIG. 11E is located closer to the "top" (e.g., towards the front of the nose when a device including this adhesive holdfast is worn by a subject). This positioning may allow the device further separate the annular regions as they bend apart from each other. In all of these variations, the adhesive holdfast is composed of a flexible or pliable material, which may allow it to more readily conform to the outer surface of the nose. FIGS. 11C to 11E also include cuts or notches 1110 at a peripheral region of the holdfast. These notches may enhance the ability of the adhesive holdfast to conform to the shape of a subject's face (e.g., nose and/or lip region), particularly when the holdfast must adhere to regions of the subject's nose and face that are at different angles with respect to each other. For examples, the notches shown in FIGS. 11C to 11E may help the holdfast region attach both to the outer rim of the nose as well as the adjacent upper lip region, and outer curvature of the nostril.

Figure 12A:
FIGS. 12A-12C illustrate additional variations of adhesive holdfasts.
Figure 12B:
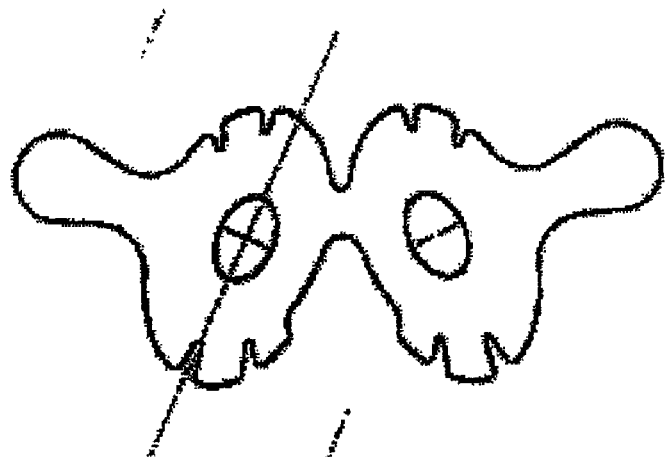
Figure 12C:
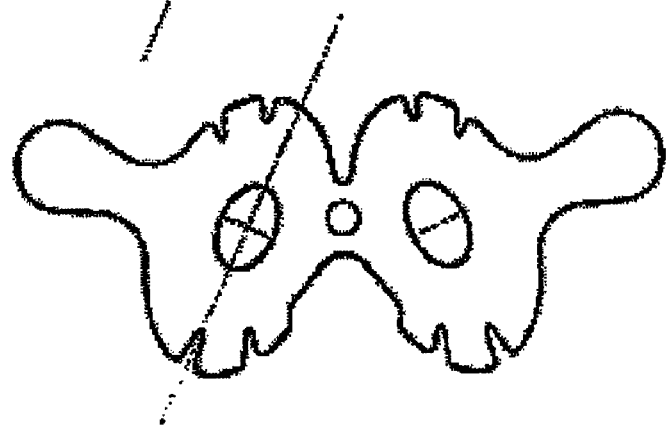

FIGS. 12A-12C illustrate other variations of adhesive holdfasts for devices having two rim bodies, in which the lower (e.g., inward facing when worn) and/or upper (e.g., outward facing when worn) areas of the holdfast annular region are notched. In addition, FIG. 12C illustrates a variation in which the bridge region 1280 includes a hole 1285, thereby reducing the material forming the bridge while retaining a substantial amount of structural strength (effectively creating two parallel bridges). This may allow the two halves of the adhesive holdfast region to more readily bend than a larger, unbroken bridge region would.

Figure 13A:
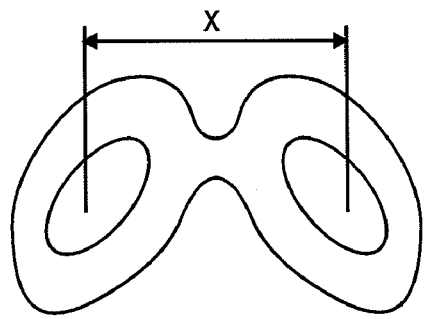
FIGS. 13A-13C illustrate additional adhesive holdfast regions.
Figure 13B:
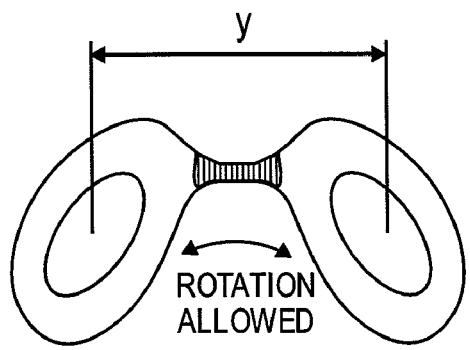
Figure 13C:
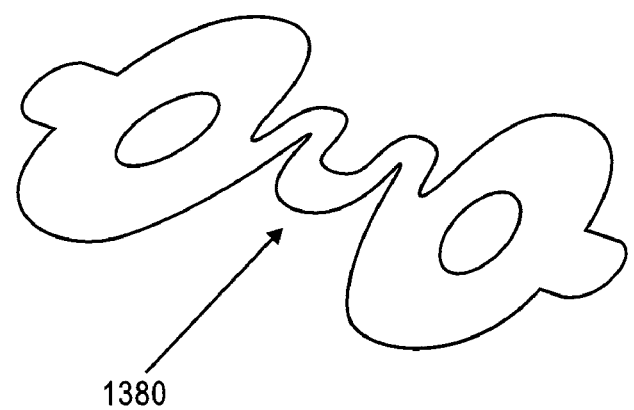

FIGS. 13A-13C illustrate an adhesive holdfast region in which have a bridge region that can expand as well as bend. For example, the adhesive substrate can comprise a flexible or stretchable material. In some variations, this material is elastic; however it may be preferable for the bridge material to comprise a relatively inelastic material, so that it does not apply force to return to the unstreched shape after begin applied to the subject's nose. FIG. 13A shows one variation of an adhesive holdfast in a first (unstreched) position. The openings through which the rim body regions are secured is separated by a distance x. In FIG. 13B, the same adhesive holdfast has been stretched so that the bridge region is extended, and the openings for the rim body regions of the device are now separated by a distance y, where y>x. Similarly, the adhesive holdfast shown in FIG. 13C comprises a bridge region 1380 that is serpentine, or shaped so that it can accordion open, allowing it to more readily adjust to different nose sizes.

Figure 14A:
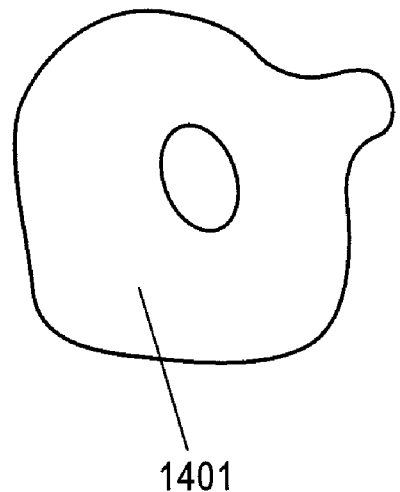
FIGS. 14A and 14B show variations of adhesive holdfasts.
Figure 14B:
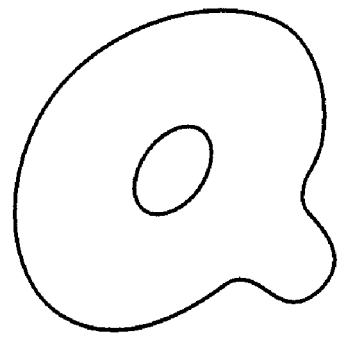

The adhesive holdfast regions illustrated above show adhesive nasal devices configured to have two rim bodies and to communicate with both of a subject's nostrils. Thus, the adhesive holdfast includes two annular holdfast regions (one surrounding each rim body) are connected by a bridge region. However, adhesive nasal respiratory devices may be configured to communicate with a single nostril. Thus two unconnected nasal respiratory device (each device including a single annular adhesive holdfast region) may be connect to each nostril. FIGS. 14A and 14B show variations of an adhesive holdfast for such a device. Compared to the previously described adhesive holdfasts, the holdfast in FIG. 14A has a slightly expanded annular region, particularly in the region of the device worn near the subject's inner nostril area 1401. In operation, this portion of the holdfast may overlap (and be adhered to an overlapping portion) with another adhesive holdfast from an adhesive nasal device worn in/around the other nostril. In some embodiments, the shape of the holdfast is completely symmetrical as shown in FIG. 14B. Thus, the same device may be used in either the right or left nostril. In some variations the devices may be configured as "left nostril" and a "right nostril" devices that may be worn together.

It is not necessary that the entire adhesive holdfast region include adhesive, although many of the substantially flat holdfast regions described in the preceding figures may have a biocompatible adhesive over much of the skin-contacting surface which may be covered by a protective layer that can be at least partially removed later. In some variations, only a subset of the holdfast region (including the outer layer) includes an adhesive. For example the region adjacent to the rim body may not include an adhesive, or the region beneath the tabs or grips may not include an adhesive.

Figure 15:
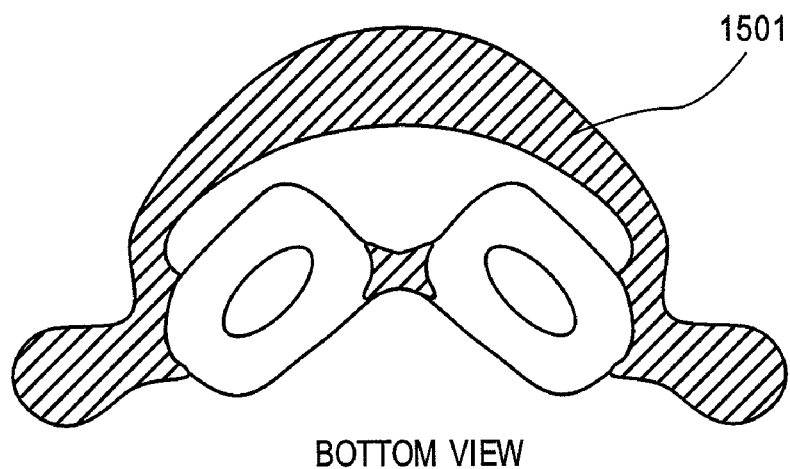
FIG. 15 is another variation of an adhesive holdfast.
Figure 15:
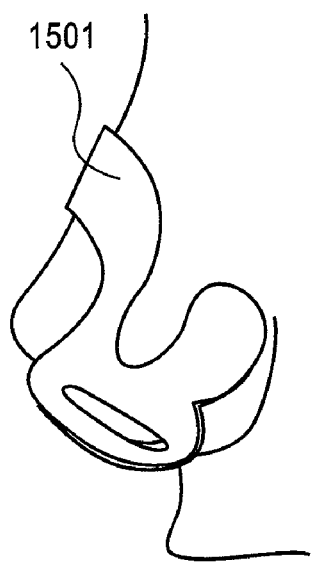
Figure 15:
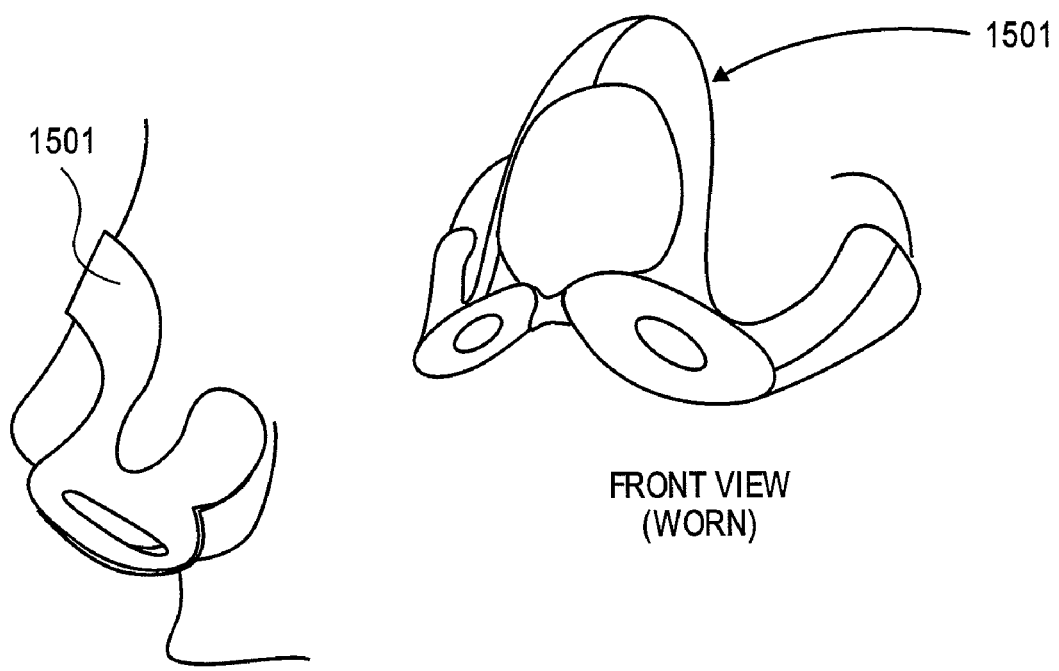
Figure 16A:
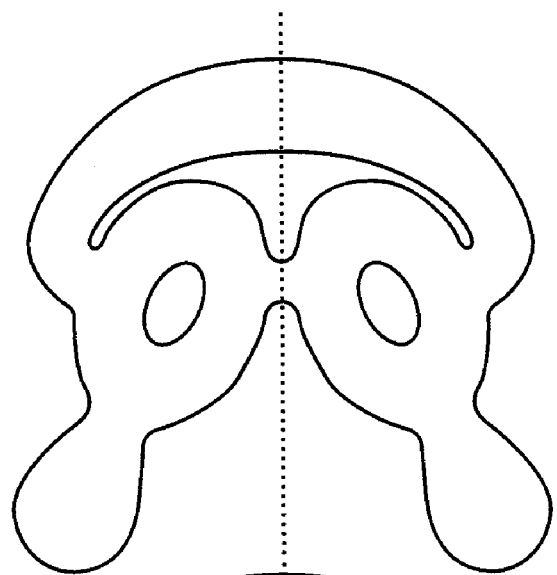
FIGS. 16A-16C are different alternative variations of the adhesive holdfast region.
Figure 16B:
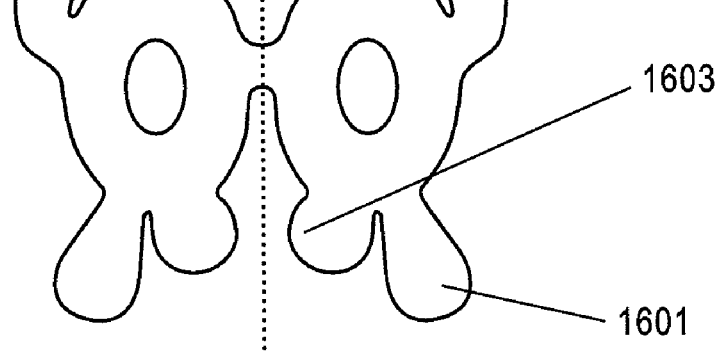
Figure 16C:
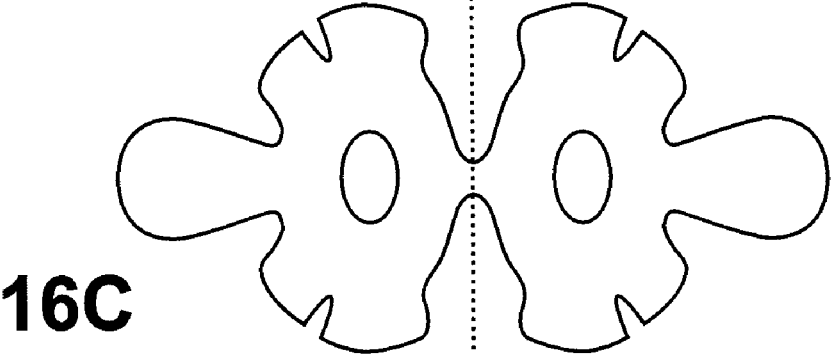
Figure 17A:
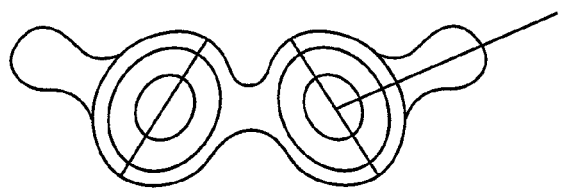
FIGS. 17A-17E are different alternative variations of the adhesive holdfast region.
Figure 17B:
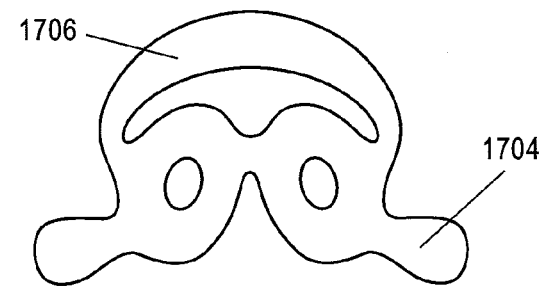
Figure 17C:
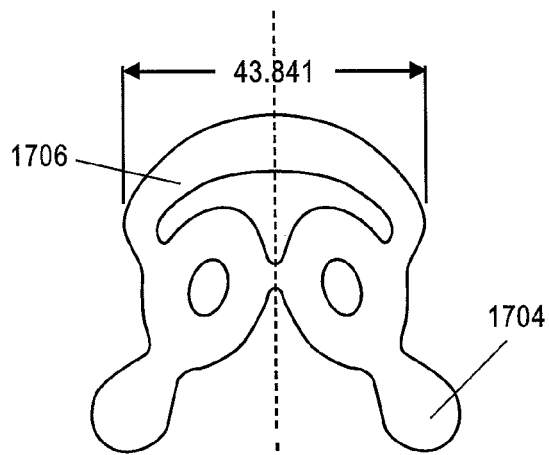
Figure 17D:
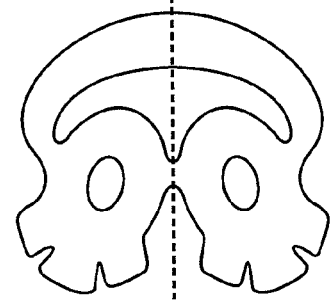
Figure 17E:
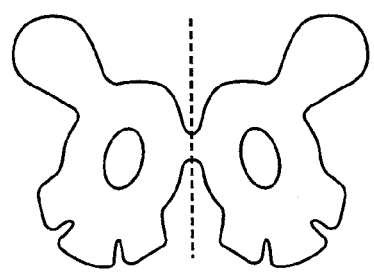

Some variations of the adhesive holdfast include one or more additional components for helping to secure the device to the subject's nose. For example, the tab or grip region described above may also help secure the device to the subject's nose (or help its removal from the nose). In some variations, the adhesive nasal device also includes an over-the-nose bridge, as illustrated in FIG. 15. The over-the-nose portion 1501 may include a region of the adhesive holdfast that fits over the bridge region of the subject's nose, and helps to secure the device in place on the subject's nose. In particular, over-nose-portion 1501 may help create a seal between the device and the nose/nostrils by exerting a force in an upward direction. In addition to the bridge region, one or more tabs (or pairs of tabs) may also be used. Other examples of an adhesive holdfast region showing over-the-nose bridge portion 1501 can be seen in FIGS. 16A, 16B and 17B-17D. FIGS. 17A-17E illustrate different alternative variations of an adhesive holdfast region. For example, FIG. 17A shows a device having only a very narrow adhesive holdfast region (e.g., annular region), but including tabs. FIGS. 17B and 17C show devices with over-the-nose bridge regions 1706 and tabs or grips 1704, where the grips are oriented in different directions. In the variation shown in FIG. 16B, two pairs of tabs or grips 1601, 1603 are included.

Figure 27A:
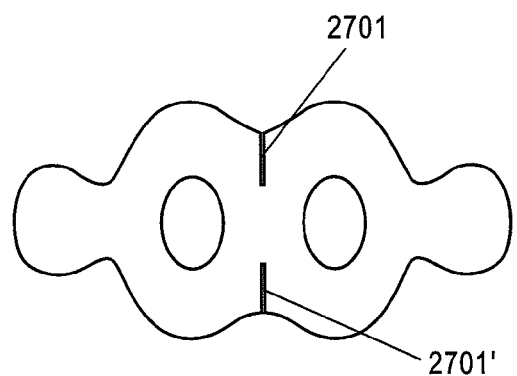
FIGS. 27A and 27C show different configurations of adhesive holdfast regions.
Figure 27B:
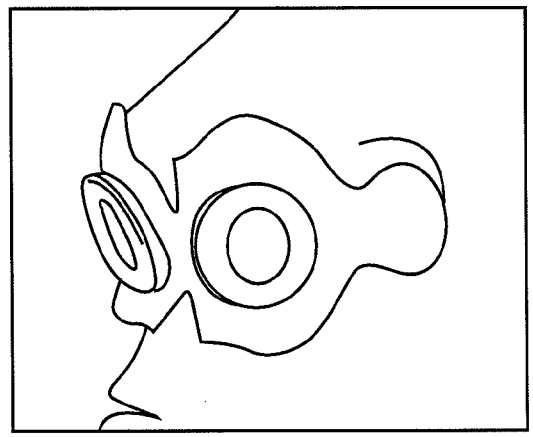
FIGS. 27B and 27D show the variations of FIGS. 27A and 27C (respectively) when worn by a subject.
Figure 27C:
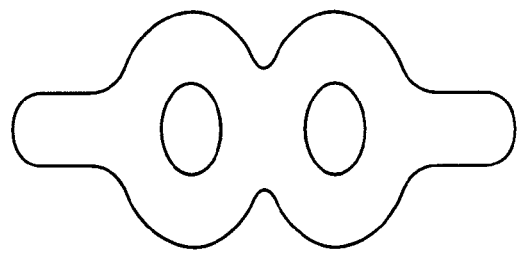
Figure 27D:
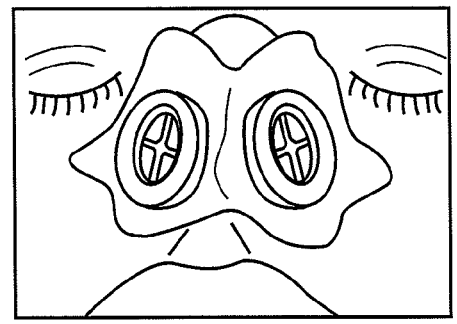

In some variations, the adhesive nasal devices described herein are adapted to fit different users having a diversity of sizes and shapes, particularly the shapes and sizes of their noses. As already described, the devices, including particularly the adhesive holdfast region, may be configured to that it is adaptable to different nose shapes. FIGS. 27A and 27C exemplify different configurations of adhesive holdfast regions. FIG. 27B illustrates how a device having a holdfast design as shown in FIG. 27A could be worn by a user. In this example, the slit or cut region 2701, 2701' separates to better conform to the subject's nose, as seen in FIG. 27B. FIG 27C shows another variation, in which silts are not included. FIG. 27D shows a subject wearing this device.

Figure 18A:
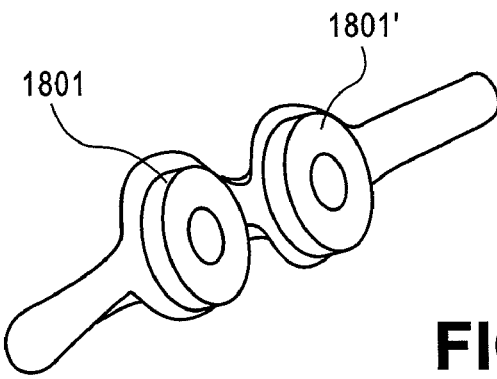
FIGS. 18A-18C are variations of the adhesive holdfast region of an adhesive nasal device.
Figure 18B:
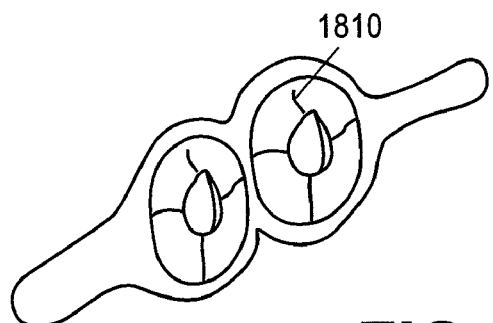
Figure 18C:
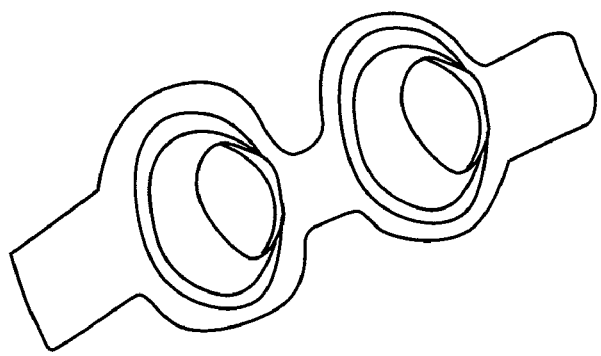

In some variations, the holdfast region may extend into the nostril, rather than just adhering around the outer surface of the nasal passages. For example, the adhesive holdfast may include a region adjacent to the rim body (or bodies) that projects into the nostril, and can be secured against the walls of the nostril, as illustrated in FIGS. 18A-18C. In FIG. 18A, the adhesive holdfast includes both a layered (e.g., substantially flat) region that can adhere to the outer rim of the subject's nostrils, and twin internally-projecting regions 1801, 1801' that fit into the subject's nose. In some variations these internally-projecting regions do not have an adhesive outer surface or include adhesive on only a restricted portion of their outer surface (e.g., near the flat portion of the holdfast). In some variations, the internally-projecting regions may comprise a compressible material (e.g., a foam or the like) so that they may be secured within the nasal passages, and/or may cushion the inner rim base region (or any other portion of the adhesive nasal device) that projects into the subject's nostrils. Thus, in some variations, the inwardly-projecting portion of the holdfast is smaller than the nasal opening, and does not necessarily contact the sides of the subject's nasal passage. Conical or tubular projections into the nostril or in close proximity to the nostril openings may find use.

FIG. 18B illustrates another variation of the inwardly-projecting holdfast region, similar to that described above, except the inwardly projecting holdfast region has a tapered or curved outer edge 1810. In FIG. 18B the outer edge is nearly concave, a shape that may be useful to prevent irritation to the subject by cushioning the inner rim body, but minimizes the chance that the inwardly-projecting region contacts the nasal passageway. FIG. 18C shows another variation having a slightly less curved outer wall (e.g., the wall cross-section is not convex, but may have a constant slope, or be slightly concave). Convex interfaces with the inside or outside of the nostril may also find use.

Figure 19A:
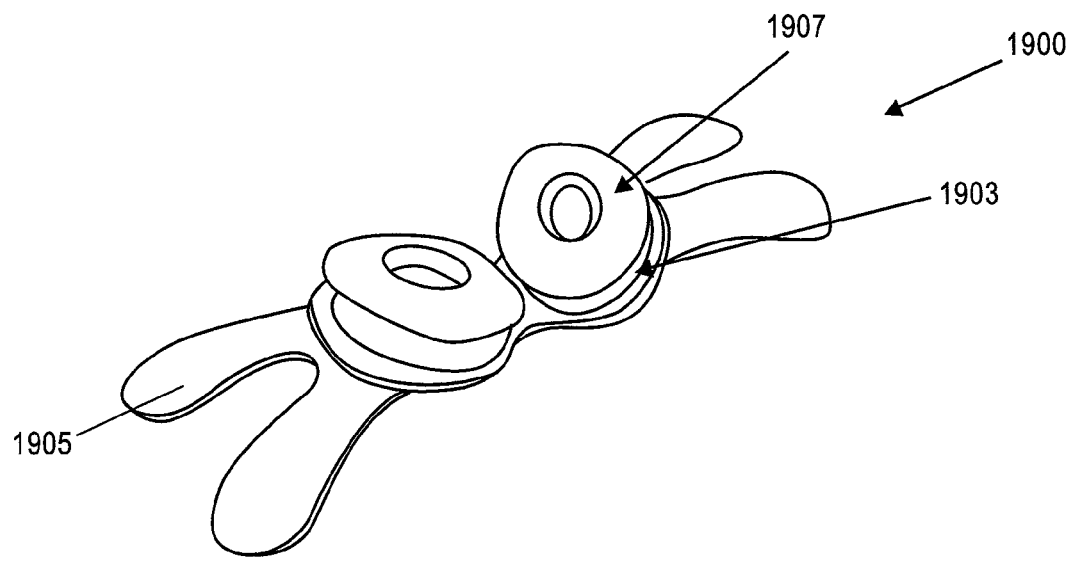
FIG. 19A is one variation of an adhesive nasal device.
Figure 19B:
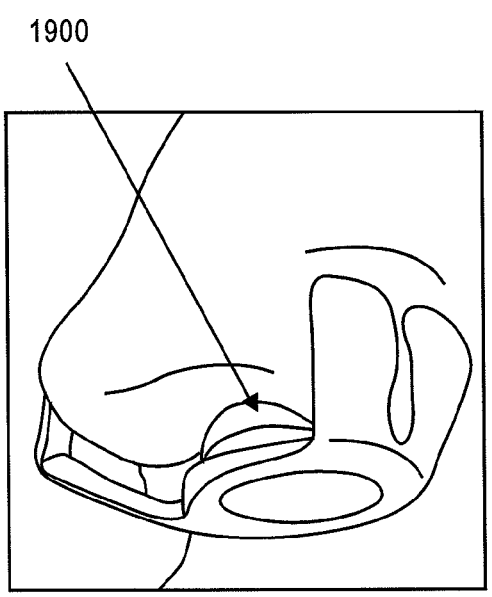
FIG. 19B shows the device of FIG. 19A applied to a subject's nasal cavity.

In some variations the inwardly-projecting region is configured as a plug which inserts into the nasal opening and is held against the nasal opening by the flexible adhesive holdfast. Thus, the plug may form a seal with the nasal opening. In some variations, the holdfast (though generally made of a flexible material) includes one or more rigid or semi-rigid regions that may be used to add support. For example, FIG. 19A shows one variation of an adhesive nasal device 1900 having a holdfast region including plugs 1903 that insert at least partly into the subject's nasal openings, a rigid support backing 1905 to support the plugs, and a flexible adhesive region (including two sets of tabs) for securing the device to the outer region of the subject's nose, as shown in FIG. 19B. In this example, the outer surface of the plug region of the holdfast 1903 include a hydrogel material 1907 that may enhance the ability to form a seal, and may also increase comfort when the device is worn.

Figure 20:
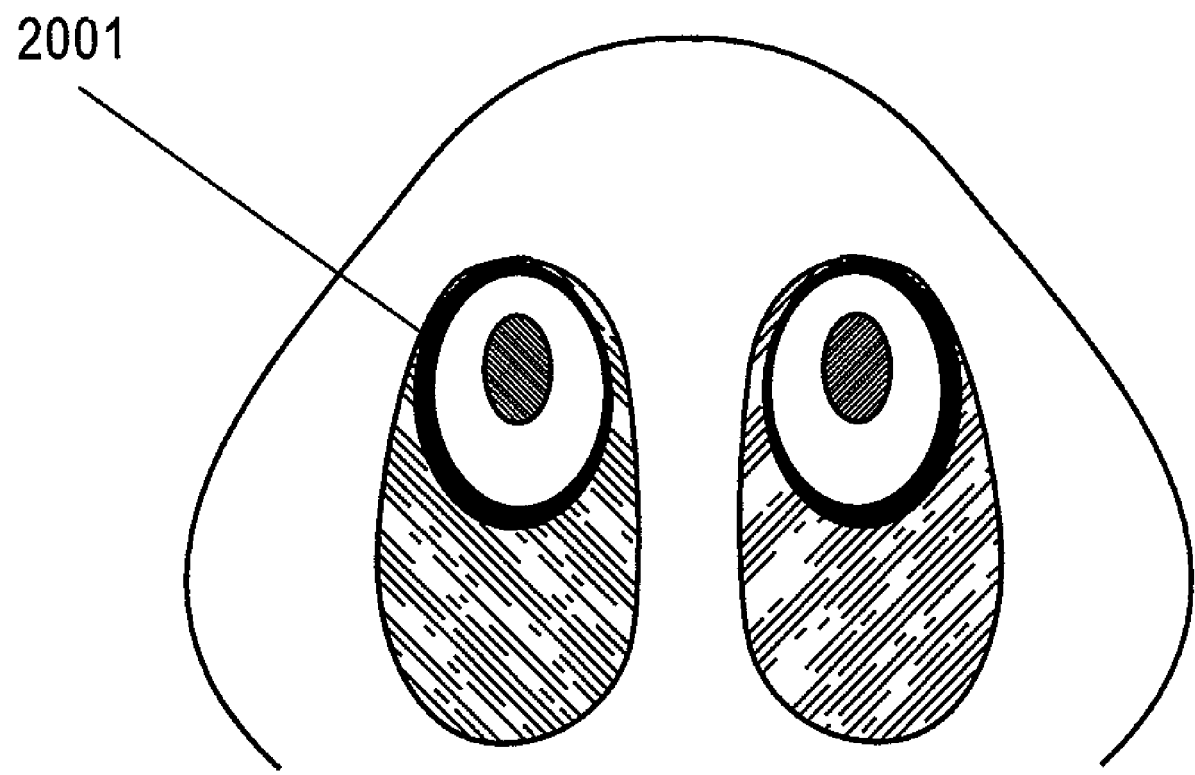
FIG. 20 illustrates a bottom view of an adhesive nasal device applied to a subject's nasal cavity.

As will be clear from the exemplary holdfast regions previously discussed, the holdfast region may help position the rim body (and thus the passageway and airflow resistor) with respect to the subject's nasal passageway. In variations in which the rim body is secured through openings in the holdfast, the openings may determine where the rim body resides with respect to the nasal passageway when worn on a subject's nose. In some variations, the rim body 2001 is biased to one particular side of the nasal passageway, as shown in FIG. 20. In other variations, the rim body may be positioned in approximately the center of the nasal passageway.

Manufacture of Adhesive Nasal Devices

The adhesive nasal devices described herein are typically assembled to provide a device of sufficient durability that it can be worn without risk of malfunction or breaking when worn over a subject's respiratory orifice. The modular (e.g., formed of two or more parts) rim body described above, including an first and second rim body portions, may be used to secure the other component parts of the device including the holdfast region and the airflow resistor by securing these regions between the inner and outer rim bodies and securing the rim body portions together.

Figure 21:
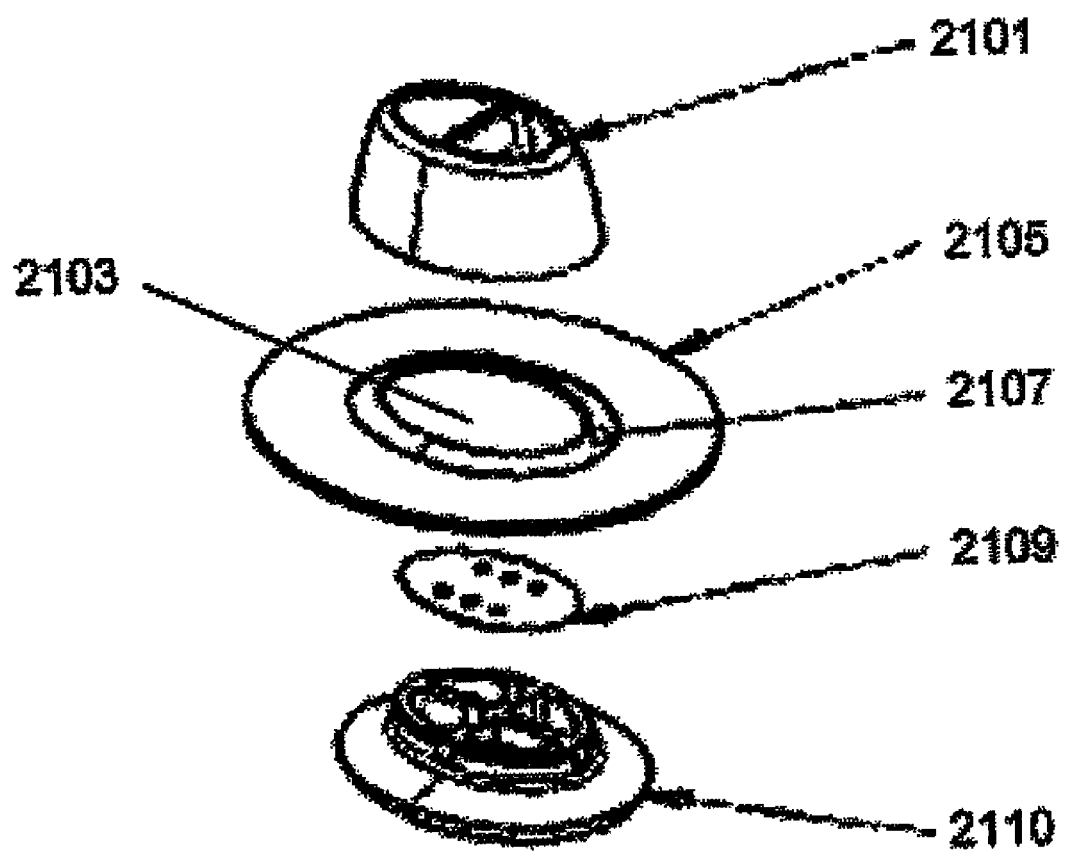
FIG. 21 illustrates assembly of one variation of an adhesive nasal device.

FIG. 21 illustrates the assembly of one variation of an adhesive nasal device. In FIG. 21, the adhesive holdfast 2105 includes a central cut-out region 2103 into which a portion of the outer rim body 2110 fits. The rim body surrounds airflow passageways, including leak pathways and the passageway regulated by the airflow resistor, as described above. The airflow resistor in FIG. 21 is configured as a flap valve, and the flap 2109 fits onto posts projecting from the outer rim body 2110 (although they may also project from the inner rim body). The inner rim body 2101 can then mate with the outer rim body 2110, and secure the flap 2109 and the adhesive holdfast 2105 therebetween, and the outer 2110 and inner 2101 rim body regions can then be secured together. For example, the outer 2110 and inner 2101 rim body regions can be secured together by welding (e.g., ultrasonic welding) or by press fit.

Figure 22A:
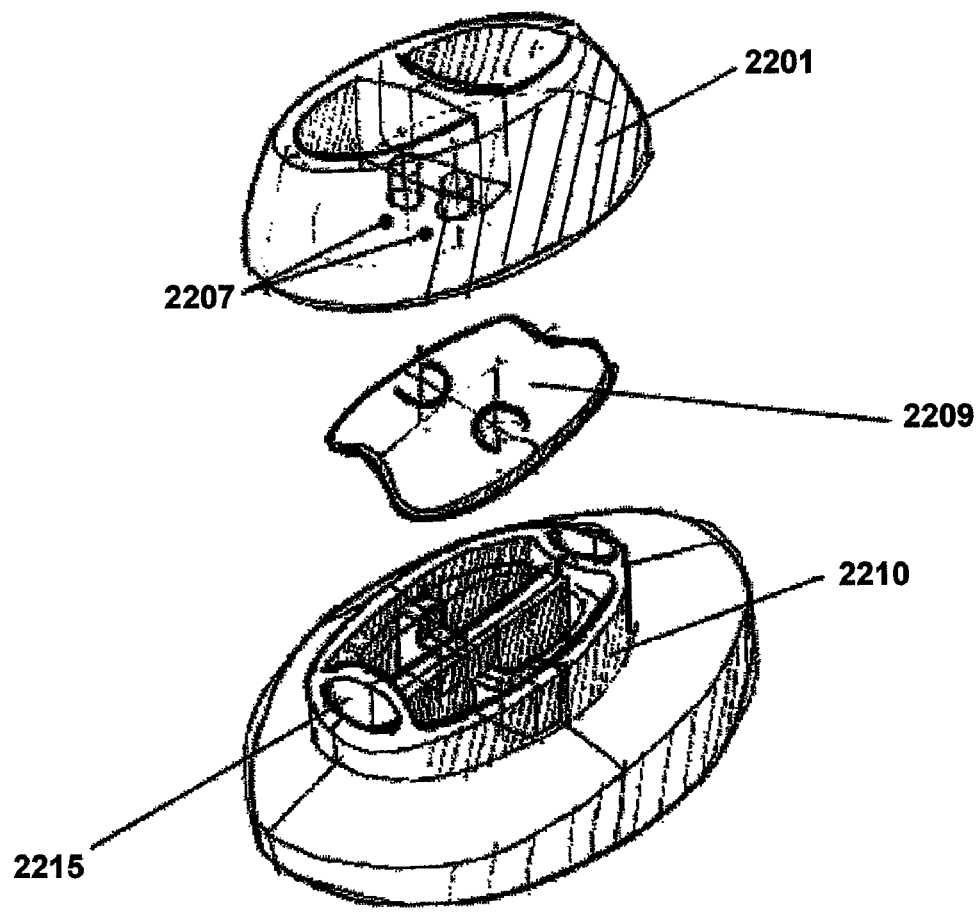
FIG. 22A is another example of the assembly of an adhesive nasal device.

In FIG. 21, the holdfast region is held between the inner and outer rim body regions by the shape of the rim body regions as well as the compression between them. In addition, the adhesive layer of the adhesive holdfast may also be used to help secure the holdfast region to the rim body. This adhesive may also help form a seal between the adhesive holdfast and the rim body, further helping direct airflow through the airflow passageway of the device when worn by a subject. Thus, in FIG. 21, the adhesive holdfast 2105 has a central annular region 2107 in which the adhesive has been exposed (e.g., by removal of the protective cover in this region). FIG. 22A shows another example of the assembly of an adhesive nasal device, similar to that shown in FIG. 21.

Figure 22B:
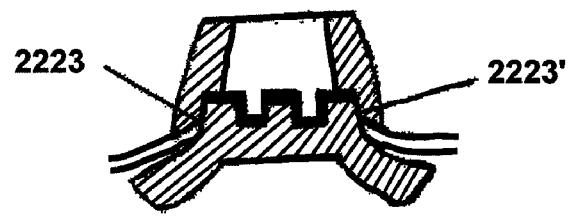
FIG. 22B illustrates the connection between two regions of an adhesive nasal device.

In FIG. 22A, the inner rim body 2201 includes posts that align and secure the flap 2209 within the passageway formed through the rim body. This example also includes two leak pathways 2215 which are not covered by the flap valve 2209 of the airflow resistor. FIG. 22B illustrates a cross-section through the assembled device shown in FIG. 22A. In FIG. 22B, the inner 2201 and outer 2210 rim body regions may be welded together where they mate with each other 2223 and 2223' securing the flap valve and the adhesive holdfast layer between the first and second rim body regions.

Figure 23A:
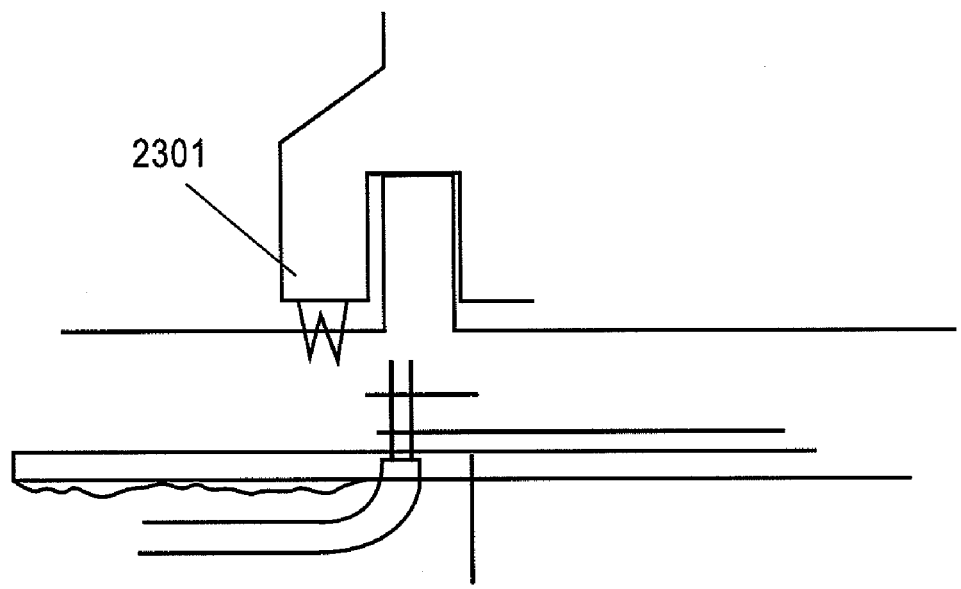
FIG. 23A illustrates one method of securing a holdfast to a nasal device.
Figure 23B:
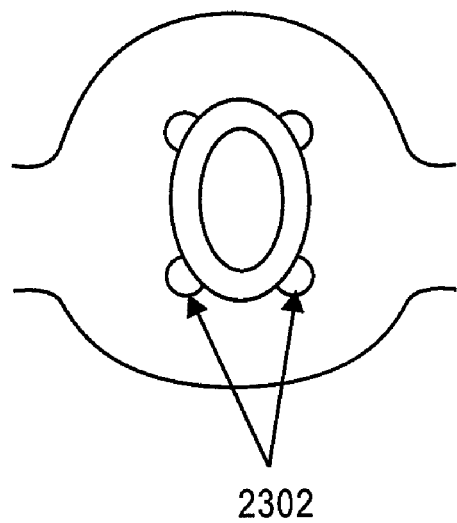
FIG. 23B shows a top view of a device as shown in FIG. 23A.

As mentioned above, the adhesive holdfast may be secured between the first and second rim bodies by pressure (and/or by adhesive). For example, a portion of the first rim body may press the adhesive holdfast against the second rim body (or vice versa). In some variations, an annular edge of the first rim body compresses the holdfast against the second rim body. In some variations, either the first or second rim body regions may include one or more mating regions that help hold the adhesive holdfast between the first and second body regions. FIG. 23A shows one variation in which an edge of the first body rim includes a pointed or sharp portion 2301 that pins the adhesive holdfast against the opposite second body rim. In some variations, such posts or projections may help secure the adhesive holdfast between the first and second body rims. FIG. 23B shows a top view of a device having four such projections arranged around the periphery of the inner rim body 2302.

Figure 24A:
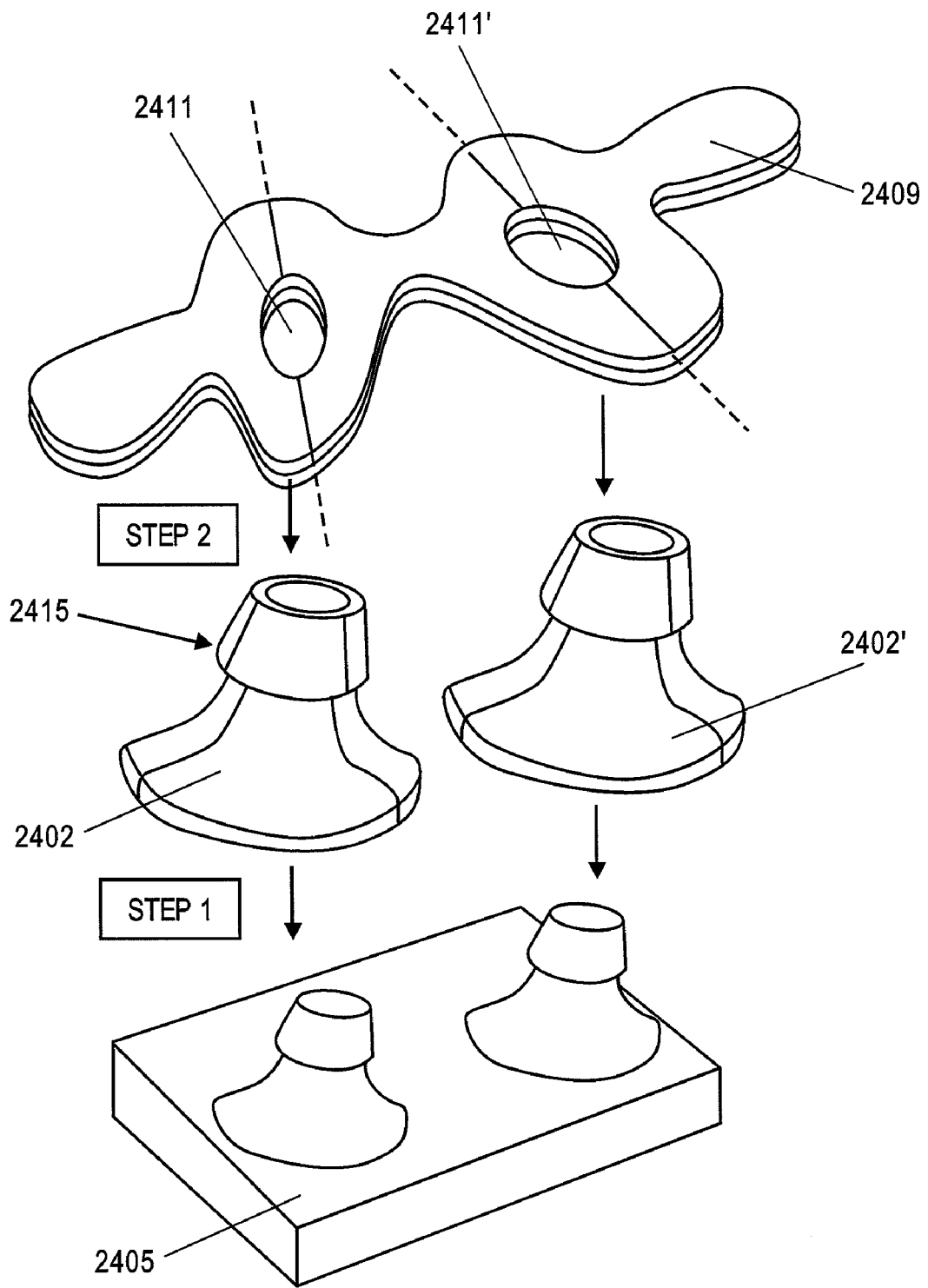
FIG. 24A illustrates another example of the assembly of an adhesive nasal device.
Figure 24B:
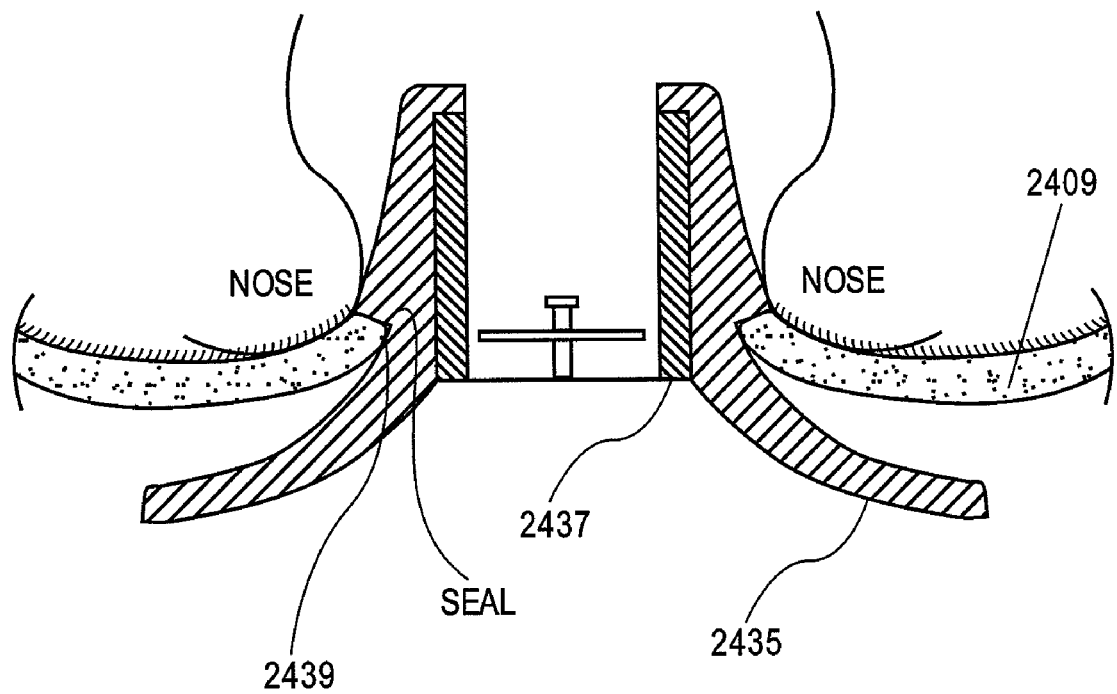
FIG. 24B illustrates how one variation of an adhesive nasal device may be inserted into a subject's nostril and secured in place.

As mentioned previously, in some variations, the rim body is not assembled by closing the holdfast region in order to secure the two components together. For example, in some variations the holdfast region is formed around the rim body. FIG. 24A illustrates another example in which the holdfast region is pulled over the pre-formed rim body region. In FIG. 24A, two rim bodies 2402, 2402' are aligned (e.g., using a guide 2405, as shown to hold them in position) and an adhesive holdfast 2409 is pulled over the rim bodies. In this example, the adhesive holdfast 2409 is flexible (and may even be somewhat elastic) so that the openings 2411, 2411' may expand as the holdfast is drawn over the larger diameter portion of the rim body (corresponding to the inner rim body region). The rim body includes a lip or channel 2415 into which the edge of the openings 2411, 2411' may sit after being pulled over the rim bodies. The lip or channel may also be configured as a barb, to prevent the adhesive holdfast from sliding off of the rim body. Variations in which the adhesive holdfast is pulled over the assembled rim body may be particularly useful for reusable (or partially reusable) devices. For example, the rim bodies may be reused with a new adhesive holdfast region by pulling the rim bodies off of the old adhesive holdfast. In general, the adhesive nasal device described herein may be disposable, or configured for single use. FIG. 24B is a cross-section illustrating how an embodiment similar to that shown FIG. 24A may be inserted into a subject's nostril and secured in place. In this variation, the rim body includes a soft outer portion 2435, and a stiffer inner portion 2437, including the airflow resistor and passageway (and any leak paths). The adhesive holdfast includes an adhesive layer 2439 that is attached to the rim body.

Figure 25A:
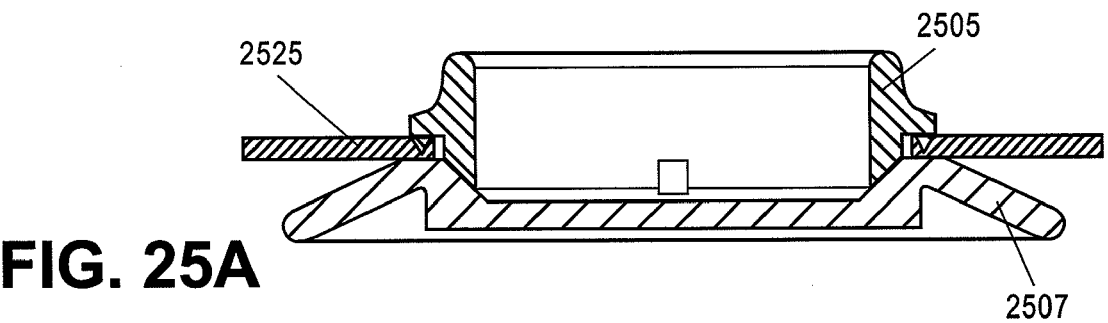
FIGS. 25A-25E show different design variations of rim body regions and adhesive holdfast regions forming adhesive nasal devices.
Figure 25B:
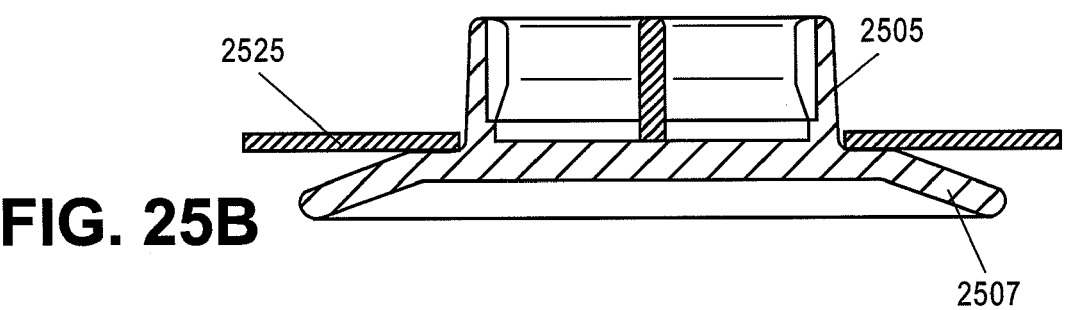

FIGS. 25A-25E illustrate a number of different design variations showing the relationships between the rim body and the adhesive holdfast region 2525. For example, in FIG. 25A, the inner rim body 2505 includes a pointed (or sharp) edge region that pinches (or even punctures) the holdfast region and secures it against the outer rim body 2507, similar to the design described above for FIGS. 23A and 23B. FIG. 25B shows another variation in which the adhesive holdfast 2525 is not secured to the rim body by closing it between an inner and an outer rim body portions. Instead, the adhesive holdfast 2525 is slid over the rim body 2501, and it may be held against the rim body by other means (e.g., adhesive, welding, tacking, etc.). In this example an inner rim body 2515 may still fit into the outer rim body 2517 (e.g., to secure the airflow resistor therein).

Figure 25C:
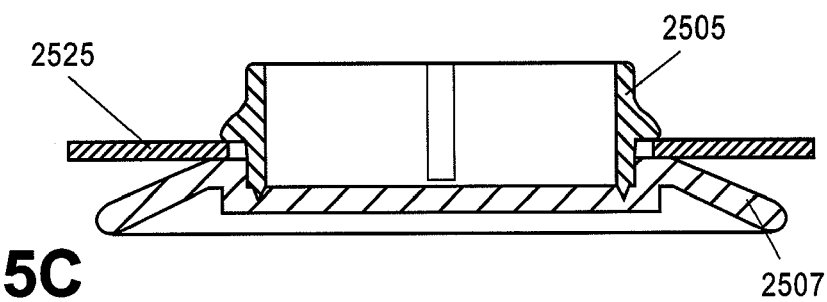
Figure 25D:
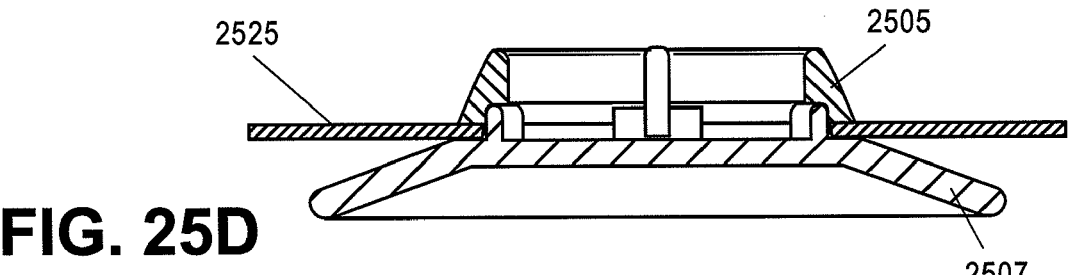
Figure 25E:
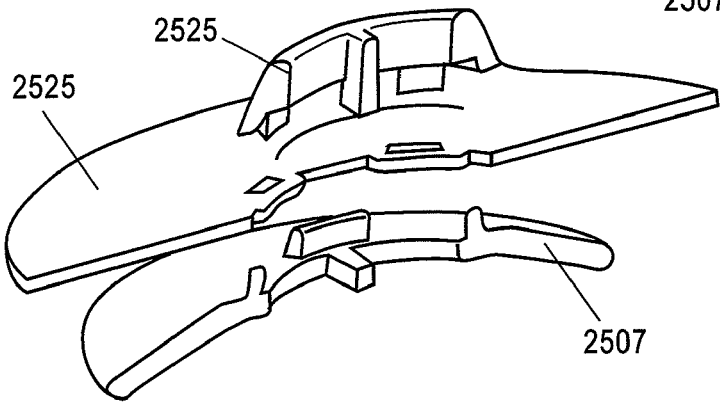

FIGS. 25C and 25D reflect different variations of the rim body having an inner 2505 and outer 2507 rim body regions that close to secure the adhesive holdfast in position. FIG. 25E shows a partial exploded perspective view of the device shown in FIG. 25D, in which the inner rim body 2505 includes interlocking sections that fit into holes or receptacles in the outer rim body 2507. In this variation, the adhesive holdfast 2525 includes holes through which these interlocking tabs fit. In other variations, the adhesive holdfast is simply compressed between the inner and outer rim bodies.

In variations in which two or more rim body portions are joined to form the rim body, the individual rim body portions may be joined in any appropriate way. For example, a snap-fitting may be used to engage the inner and outer rim body portions, as shown in FIG. 26B.

Figure 26A:
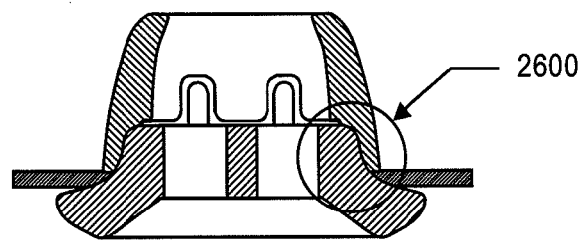
FIGS. 26A-26C show cross-sections though assembled adhesive nasal devices.
Figure 26B:
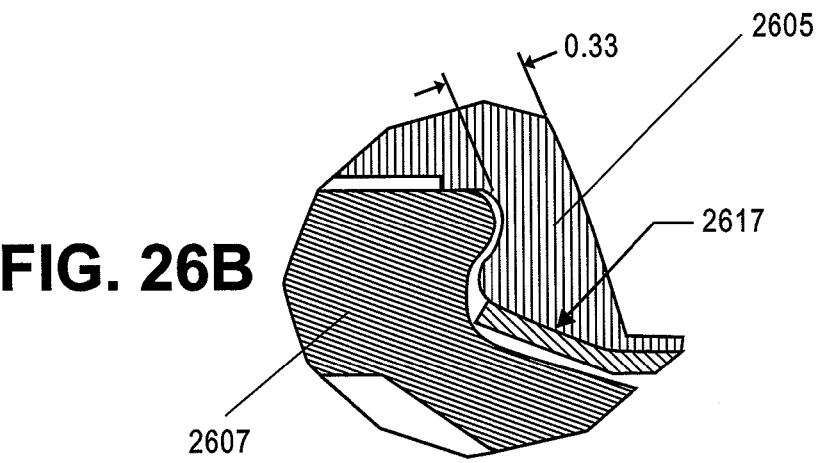
Figure 26C:
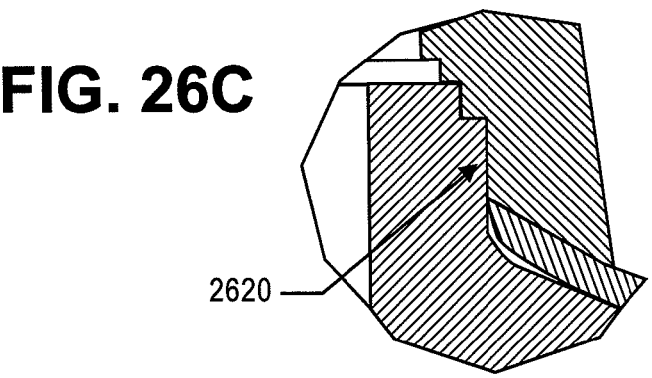

FIG. 26A shows a cross-section though an assembled device including a rim body and an adhesive holdfast. The circled region 2600 indicates the region of the partial cross-section of the assembled rim body shown as different alternatives in FIGS. 26B and 26C. In FIG. 26B, the inner rim body 2605 has interlocked with the outer rim body 2607, so that the two are 'snap-fit' together. A portion of the adhesive holdfast 2617 is also shown attached to the inner body rim 2605 (in part due to the adhesive on the adhesive holdfast). In FIG. 26C, the inner 2605 and outer 2607 rim bodies are welded (e.g., ultrasonically welded) together in the region indicated 2620.

In operation, the user secures the devices to his or her nose by applying the adhesive holdfast region against the nose to form a seal, so that the majority of airflow through the nose passes through an airflow resistor, thereby regulating respiration through the nose. For example, the airflow resistor may be configured so that resistance to exhalation is greater than resistance to inhalation.

In addition to the components described above, the adhesive nasal devices may be used with additional components, including fitting adapters and cannula adapters (or nasal cannula connectors). A fitting adapter may be an additional (e.g., separate) piece that attaches in, around, or to the subject's nose to act as an additional substrate for attachment of the adhesive nasal device. For example in subject's whose noses are too small for a standard-sized adhesive nasal device to comfortably fit (and seal), a fitting adapter may be used to better secure the adhesive nasal device.

Figure 28A:
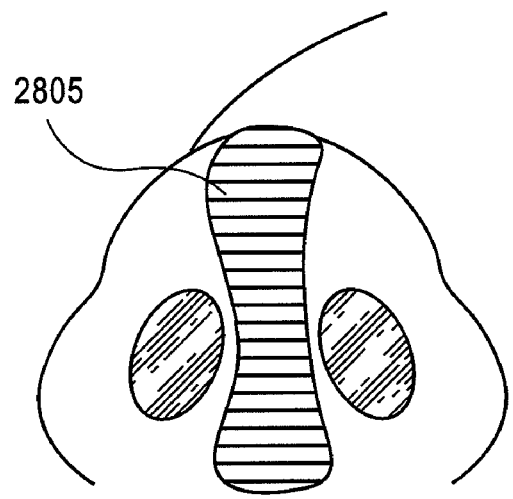
FIGS. 28A and 28B illustrate a fitting adapter.
Figure 28B:
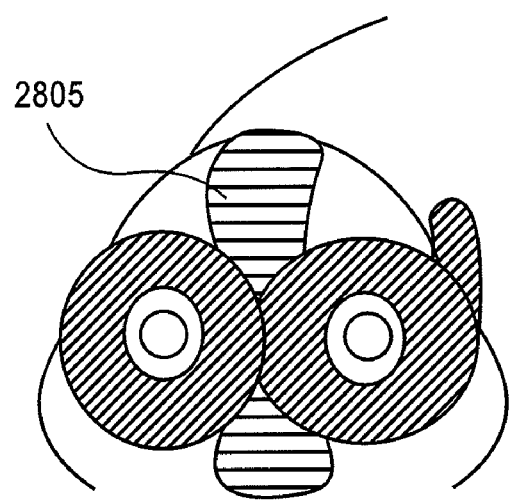

A fitting adapter (which may be made from the same basic material as the adhesive holdfast of the device) is first applied to the subject's nose, and the adhesive nasal device may then be applied over the fitting adapter and onto the nose. For example, a fitting adapter may be applied to the external septal region of the nose (e.g., the tissue between the two nostril openings), and provide a regular and possibly larger surface against which the adhesive nasal device may fit. FIGS. 28A and 28B illustrate a fitting adapter 2805 applied to the outer septal region of a subject. In FIG. 28B, an adhesive nasal adapter has been applied overtop of the fitting adapter. Although the fitting adapter shown is an external septal fitting adapter, a fitting adapter may be provided to any region of the nose, including the entire nose, or a sub-portion thereof.

Figure 29A:
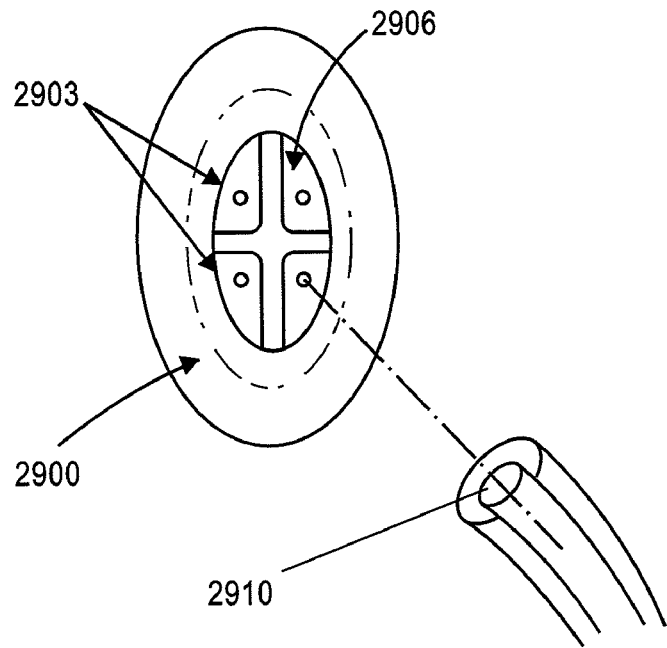
FIGS. 29A and 29B show bottom views of two variations of an adhesive nasal device compatible with a nasal cannula adapter.
Figure 29B:
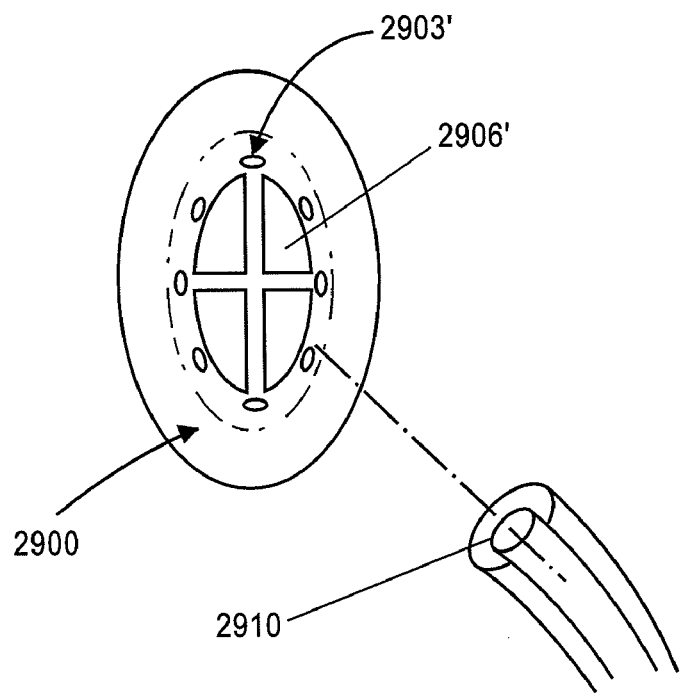

Any of the devices described herein may also be used with a cannula adapter so that they may be used with a cannula. Thus, a cannula may be secured in proximity to the subject's nasal orifice by the adhesive nasal device. For example, a cannula may be used to take measurements of airflow (or pressure) through the nasal passageway. In some variations, a cannula is attached directly to an adhesive nasal device without requiring a separate (or removable) adapter. In general, the cannula opening is aligned with an opening through the adhesive nasal device, such as a leak pathway. In some variations, the cannula (or an additional cannula) opening may be aligned with the passageway opening that is regulated by the airflow resistor. FIG. 29A shows a bottom view of a portion of an adhesive nasal device 2900 having four leak pathways 2903 through the airflow resistor (flap valve 2906). In order to measure flow within the nasal passage when an adhesive nasal device is worn, the cannula opening 2910 should be aligned with the leak pathway 2903, as indicated. FIG. 29B shows a similar illustration of an adhesive nasal device 2900' having leak pathway openings 2903' encircling the valved airflow pathway 2906'.

Figure 30A:
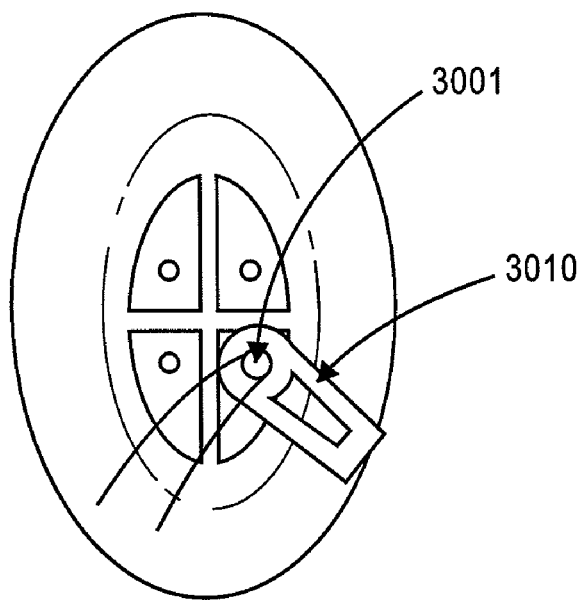
FIGS. 30A, 30B and 30C show a cannula adapter.
Figure 30B:
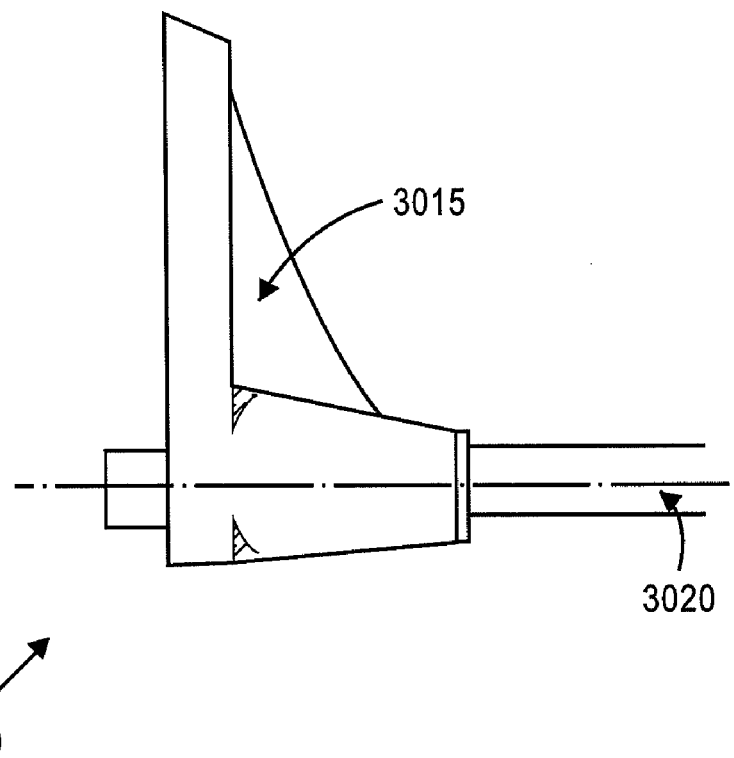
Figure 30C:
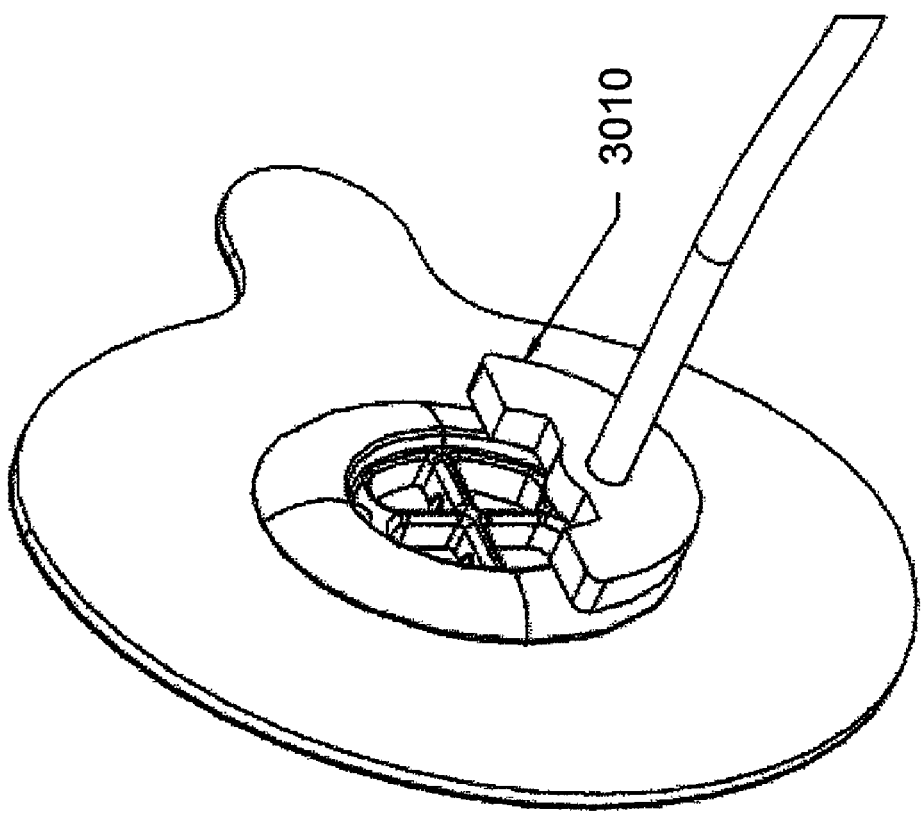
Figure 31:
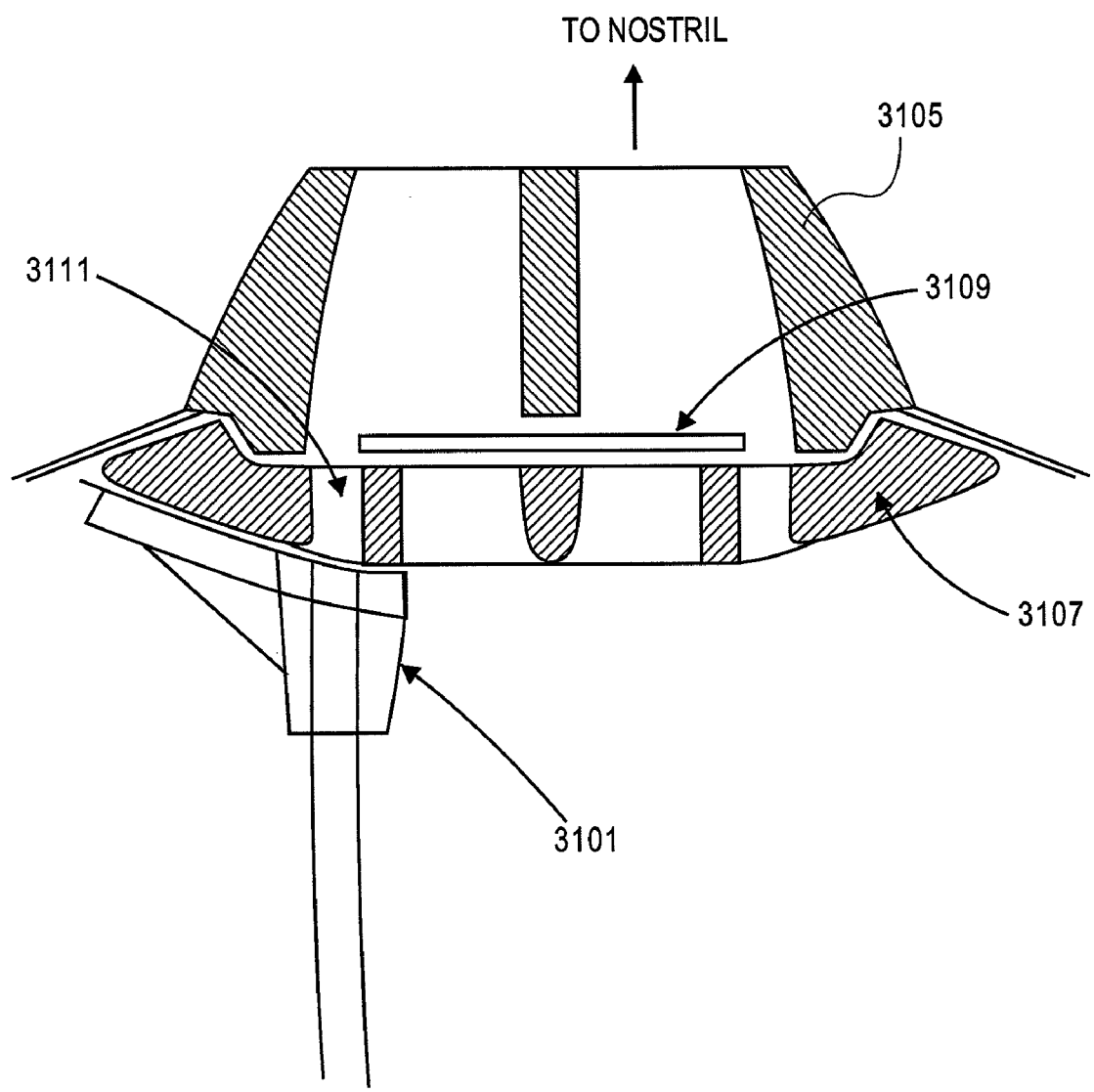
FIG. 31 illustrates a cross-section of a cannula adapter engaged to an adhesive nasal device.

A cannula adapter may be configured to securably attach to the bottom (e.g., the outer rim body) of the adhesive nasal device so that the cannula opening is aligned with a leak pathway. FIG. 30A shows a cannula adapter 3010 attached to an adhesive nasal device. In this example the cannula adapter 3010 is attached to the rim body so that the cannula 3020 opening is positioned opposite a leak pathway through the flap (similar to the arrangement discussed above for FIG. 29A). The cannula adapter includes a cannula-securing lumen (into which a cannula 3020 is mounted) and a support frame 3015 that attaches to the rim body of the adhesive nasal device. The cannula adapter may be attached by any appropriate method, including an adhesive (e.g., by using a glue) or by a mechanical engagement, or some combination. In some variations, the cannula adapter is removably attached to the adhesive nasal device. In other variations, the cannula adapter is permanently attached to the adhesive nasal device. FIG. 31 illustrates a cross-section of a cannula adapter engaged to an adhesive nasal device.

Figure 32A:
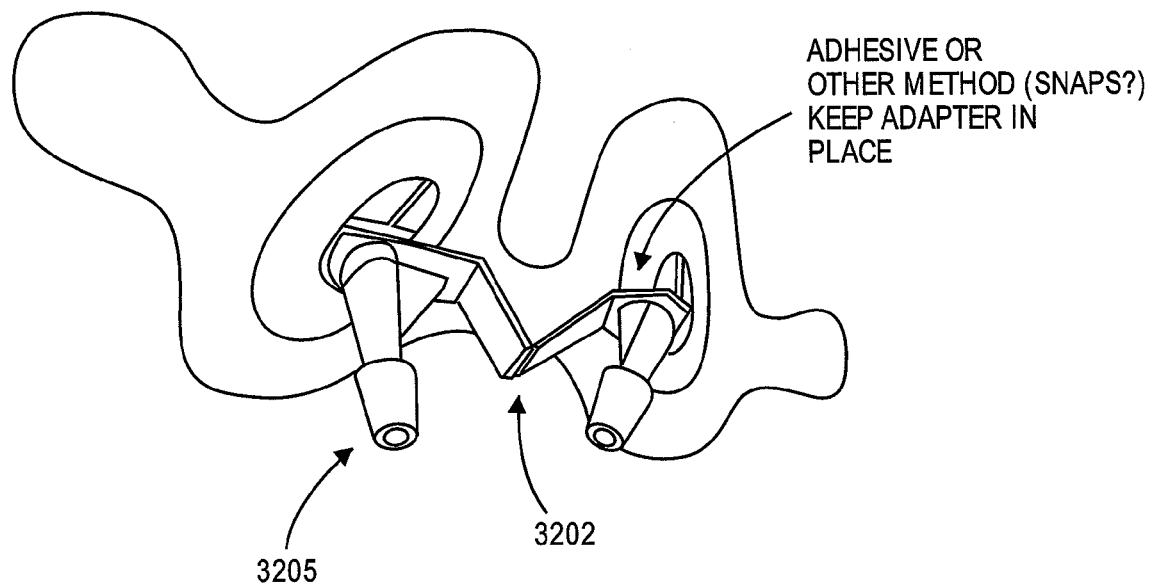
FIGS. 32A and 32B show another variation of cannula adapter.
Figure 32B:
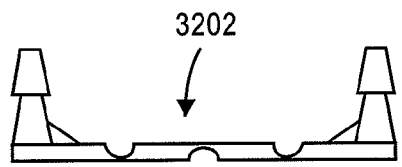

The cannula adapter shown in FIG. 31 is connected to the outer rim base 3107 so that the cannula opening is substantially continuous with the opening of a leak pathway 3111 on the adhesive nasal device. This arrangement may allow a determination of the back pressure in the nasal passage when wearing the device, even when the airflow resistor (flap 3109) changes from opened to closed. In some variations, a cannula or tube may extend beyond the level of the airflow resistor (further inside the nasal cavity) in order to capture intra-nasal pressures during portions or the entirety of the respiratory cycle. In some variations, a cannula adapter may be configured to read from both nasal passages. For example, FIGS. 32A and 32B show a variation of cannula adapter that is configured to attach to both rim bodies in an adhesive nasal device configured to fit over both nostrils. This adapter includes a hinged bridge region 3202 that is shown here as a living hinge allowing the adapter to fit subject's having different nostril spacings. The cannula adapter includes an opening that aligns with the leak pathway of the adhesive nasal device, and also includes a male lure fitting 3205 to which the cannula tubing may be attached. FIG. 32B illustrates a side view of this variation of the cannula adapter.

Figure 33:
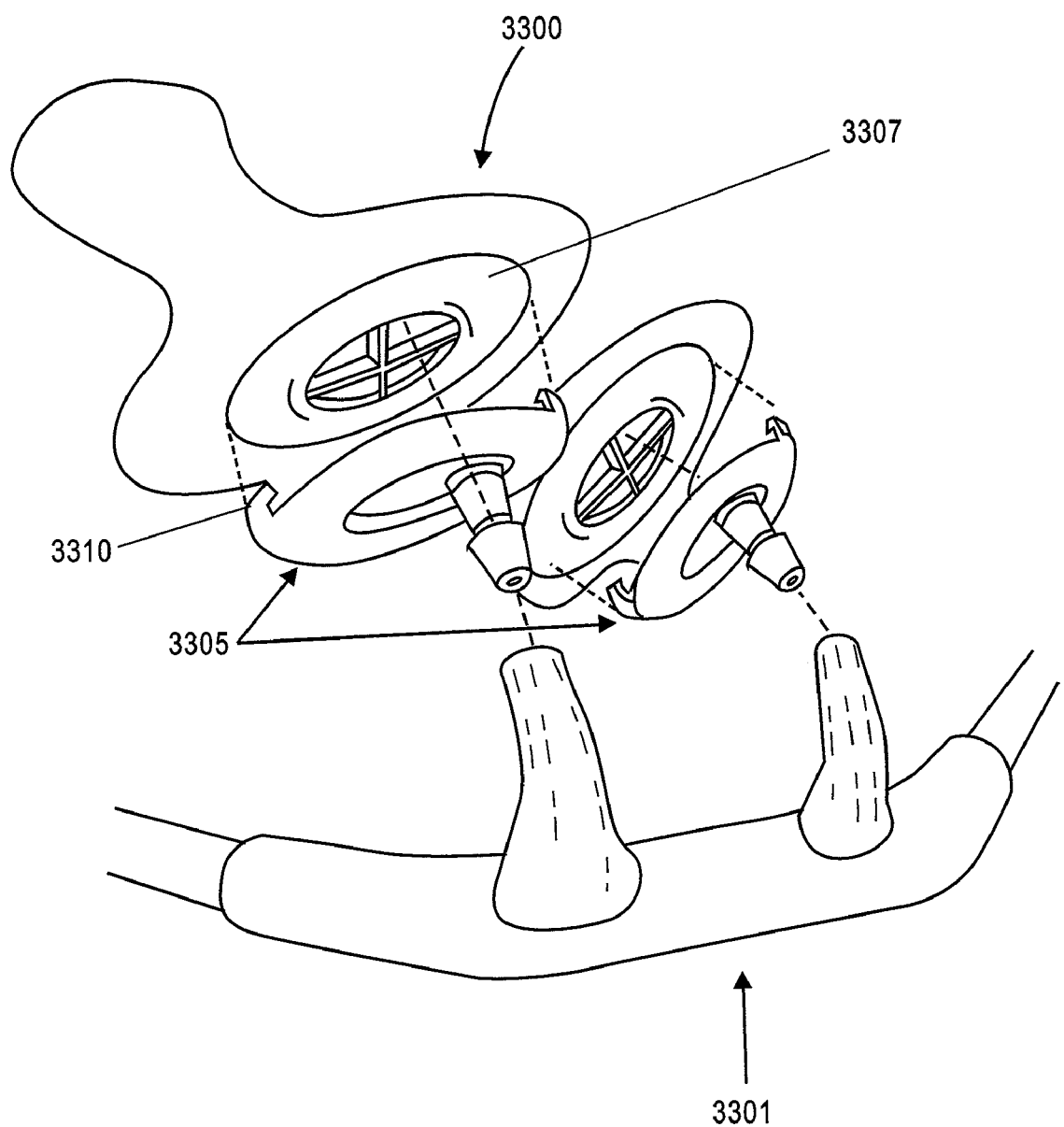
FIG. 33 illustrates the connection of a nasal cannula to a pair of cannula adapters.

A cannula adapter for an adhesive nasal respiratory device may be used with a commonly (or commercially available) nasal cannula, including two-prong cannulas. FIG. 33 illustrates the connection of a typical nasal cannula 3301 to a pair of cannula adapters 3305. The cannula adapters 3305 shown in FIG. 33 are configured to attach to the rim base regions 3307 of an adhesive nasal device 3300 by snap-fits 3310 that snap onto the rim base.

Figure 34:
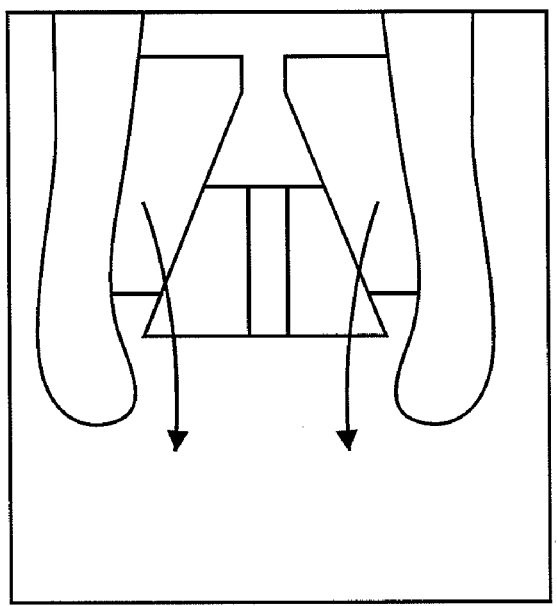
FIG. 34 shows another variation of an adhesive nasal device.
Figure 34:
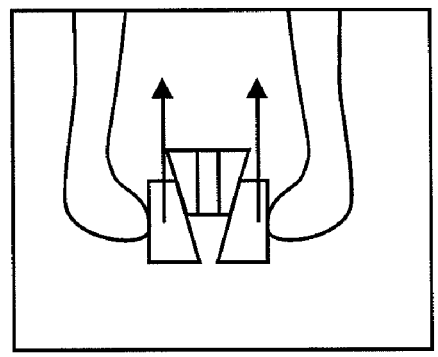
Figure 35:
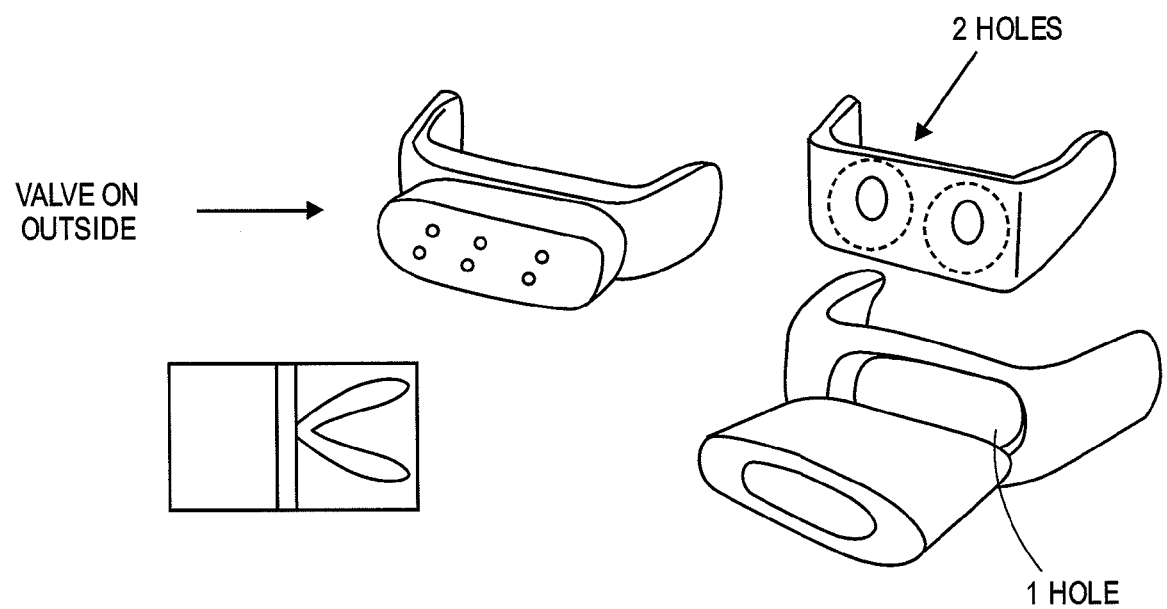
FIG. 35 shows another variation of an adhesive nasal device.

FIGS. 34 and 35 show two additional variations of adhesive nasal devices. In FIG. 34, the adhesive nasal device includes a self-expanding rim body. Thus, the rim body has a first (inner) portion that is slideable within the second (outer) portion. Moving one portion with respect to the other portion causes the outer portion to expand or contract. In FIG. 34 this is caused by the action of the wedge-shaped (or angled) inner portion pushing apart the walls of the outer portion as the inner portion is moved in one direction. Such self-expanding nasal devices may be used to secure the device within a subject's nostril without the need for additional adhesive, although it could be used with adhesive. In some variations, the device includes locking regions (e.g., 'ribs') that prevent the inner portion from easily backing out once it has been expanded by moving the inner portion inwards.

FIG. 35 illustrates an adhesive nasal device in which a single airflow resistor is used to cover both nostrils. In this variation, the adhesive holdfast secures a horizontally elongated portion opposite from both nostrils so that both nostrils empty into a common chamber or lumen. This common space is continuous with a passageway having an airflow resistor (and possible also leak pathways) therein.

Figure 36A:
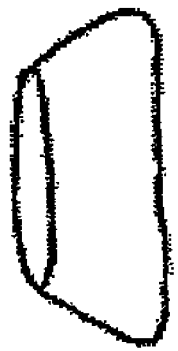
FIG. 36A shows one variation of a rim body region.
Figure 36B:
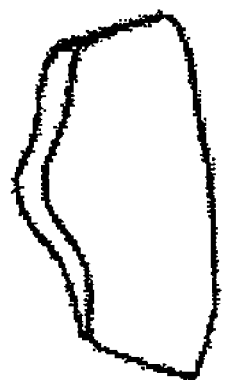
FIGS. 36B and 36C show side perspective and end views of another variation of a rim body region.
Figure 36C:
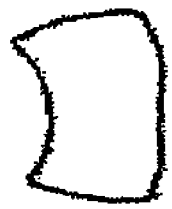

FIG. 36A to 36C shows different variations of rim body regions of an adhesive nasal device as described. In FIG. 36A, the rim body region having an upper edge (e.g., along the top of the first rim body region) that is substantially flat. In contrast, FIG. 36B shows a perspective view of a rim body region that has an arced or curved profile. This curved profile may help protect a moving flap region, and may also make fabrication easier. FIG. 36C shows an end view of the rim body shown in FIG. 36B.

In some variations of the adhesive nasal devices described herein, one or more components of the device are impregnated with, contain or are coated with one or more compounds that may be inhaled during use. The presence of airflow, heat or other conditions may facilitate the release of the compound into the inhaled air or surrounding tissues. The compound may be herbal (such as menthol or lavender), chemical or pharmaceutical (such as an antihistamine or anti asthma drug) in nature. Depending on the compound, the user might experience a pleasant aroma (which may soothe or promote sleep or activity) or medical benefits, such as nasal decongestion or asthma relief. The compound may be inhaled during all or at least a portion of the time the user is wearing the device. The compounds may be used as part of a sleep apnea, snoring or a respiratory device, or may find use in other embodiments for other medical conditions.

Any of the nasal respiratory devices described herein may be embodied used to treat sleep apnea (including obstructive sleep apnea, or OSA), snoring, or any other disorder, including those listed herein.

The adhesive nasal devices may include a filter that removes particulate matter from external air upon inhalation. Particulate matter that would be removed may include dust and allergens. The filter may be made of a material that can act as a filter for allergens, pollen, dander, smog, etc. By providing a filter within the device, sinusitis, sleep apnea, snoring, hay fever, allergic rhinitis, and other allergic respiratory conditions may be reduced or prevented. This filter may in fact be part of the airflow resistor or may be a separate component of the device. Any suitable filtering material known to those skilled in the art may be used with the respiratory devices described herein. Such materials include, but are not limited to, activated carbon charcoal filters, hollow-fiber filters, and the like. A filter may not appreciably alter resistance to airflow in either direction, or it may alter airflow to substantially the same degree in both directions (inhalation and exhalation). In some versions, the filter comprises a material having a large pore size so that airflow is not significantly inhibited.

In some versions, the device is used with an active agent. In some versions, the active agent comprises a drug. An active agent (e.g., a medicament) or other compound can be placed in or on the device to deliver the active agent into the mouth, tongue, hard and soft palates, sinuses, nose, nasal cavity, pharynx, vocal cords, larynx, airways, lungs, trachea, bronchi, bronchioles, alveoli, air sacs, or any tissues that are exposed to inspiratory or expiratory airflow. In some cases, the active agent may be embedded or impregnated in the device or components of the device. In some cases the active agent is a coating. An active agent may comprise any compound that is in some way useful or desirable for the patient. For example, the active agent may be any odorant, including: menthol, phenol, eucalyptus, or any agent that provides a fragrance in the inspired air. Alternatively, an active agent may comprise a drug with beneficial effects, such as beneficial vasculature effects. For example, an active agent may comprise a drug that effects the blood vessels (oxymetazoline or any other vasoactive compound), nasopharynx, airways or lungs (albuterol, steroids, or other bronchoconstriction or bronchodilation compounds). An active agent may comprise, for example, an antibiotic or a steroid. The above list of active agents is not meant to be limiting.

An active agent may be placed in or on any portion of the device. Furthermore, the location of the active agent within the respiratory device may specifically guide the delivery of the active agent. For example, in versions of the respiratory device configured to be placed at least partially inside a respiratory cavity, when the holdfast includes an active agent (e.g., coated, embedded or otherwise part of the holdfast), the drug may be delivered through the mucus membranes of the respiratory cavity. In another example, an active agent may be included as a powder or releasable coating that may be aerosolized and delivered within the respiratory system. Thus, an active agent may be on a surface of the device (e.g., the passageway, holdfast airflow resistor) or embedded within any surface of the device. A separate drug-containing region may also be included in the device. The addition of an active agent may be of particular interest in treating allergies and sinusitis. Respiratory devices (with or without airflow resistors) may therefore comprise active agents such as menthol or other fragrant compounds.

EXAMPLES

Figure 42B:
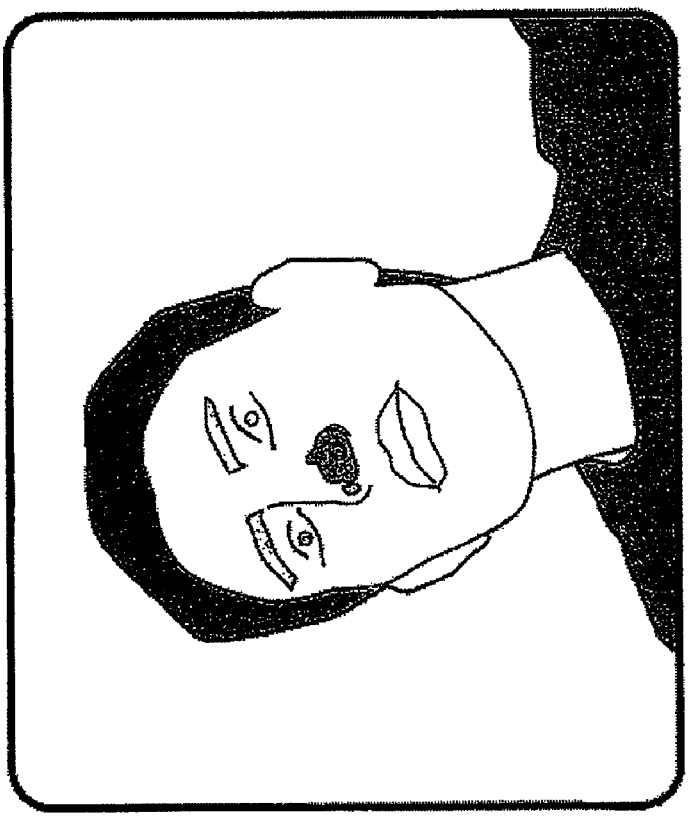
FIGS. 42A and 42B illustrate one method of using an adhesive nasal device as described herein.
Figure 42A:
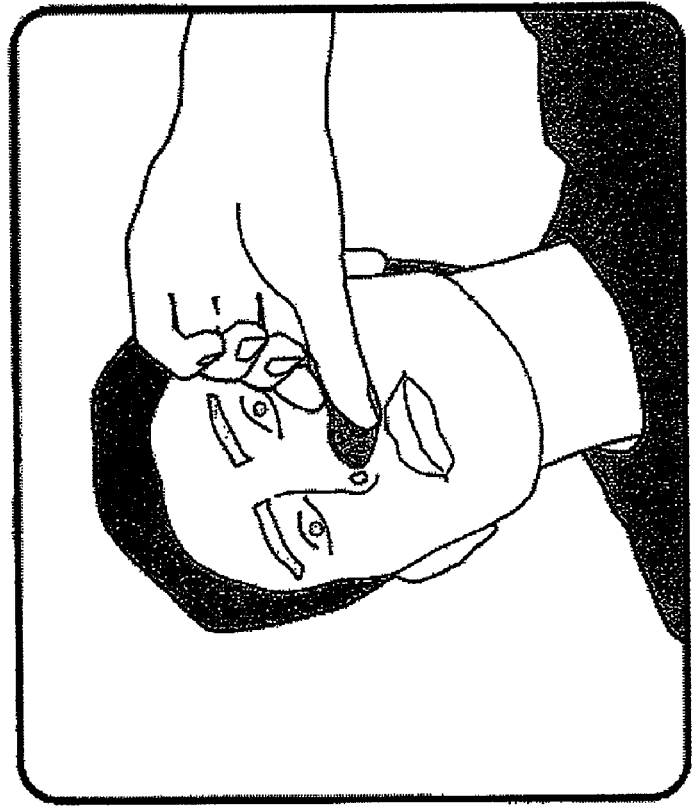

FIGS. 42A and 42B illustrates how an adhesive single-nostril nasal device may be applied to and worn by a user. In FIG. 42A, a user first peels off all (or a part of) the protective cover, exposing the adhesive holdfast region. The user may then place the device over one of the nostrils, so that the passageway through the device is aligned with the nasal openings. The rim body (e.g., inner rim body) may help the user to align the nasal opening and the central passageway of the device. The adhesive device may be applied against the nostril to secure it into position. The user may first wash the area to which the adhesive device will be applied to remove material (e.g., dirt, oils, etc.) that could prevent adhesion (and/or a seal) between the adhesive device and the nostril and/or nose.

Once a single-nostril device has been applied over one nostril (as shown in FIG. 42B), a second device may be applied to the other nostril. The adhesive holdfast regions of the two devices may overlap. To remove the devices, the user may simply peel off the adhesive devices. In some cases, as one device is removed, it will facilitate removal of the second device since the two once-independent devices may be adhered together.

Figure 39A:
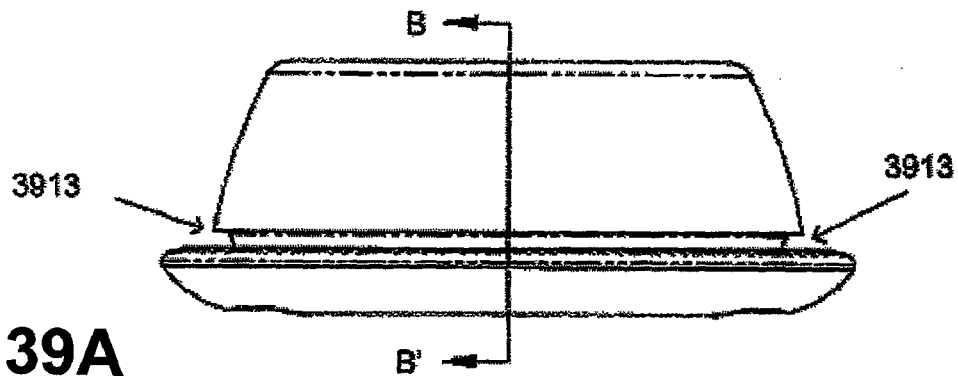
FIGS. 39A and 39C show side perspective views of one variation of a portion of an adhesive nasal device.

FIGS. 39A to 41D illustrate another variation of an adhesive nasal device. FIG. 39A shows a side perspective view of a rim body portion of an adhesive nasal device. FIG. 39B is a cross-section through this rim body, taken through line B-B' (shown in FIG. 39A). In this variation, the rim body includes an inner (or upper) rim body 3907 and an outer (or lower) rim body 3905 that fits together to form the firm body region. In this variation, the inner rim body mates with the outer rim body at a sealing surface 3909 between the inner and outer rim body regions. This sealing surface may be sufficiently snug so that an additional leak pathway is not formed between the inner and outer rim bodies.

Figure 39B:
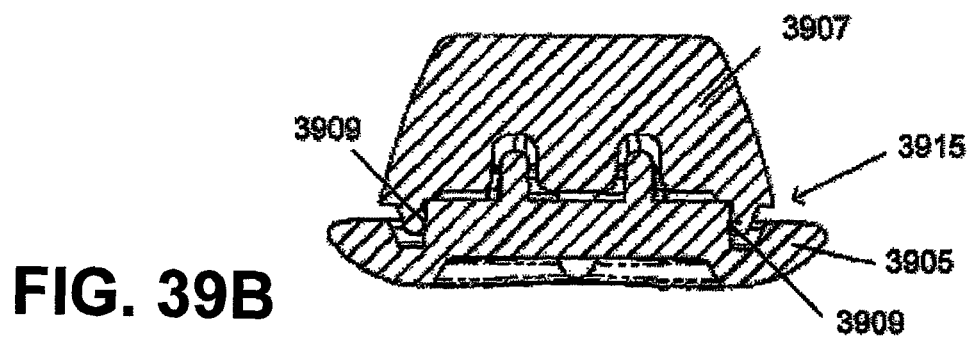
FIGS. 39B and 39D show sections through the devices of FIGS. 39A and 39C respectively.
Figure 39C:
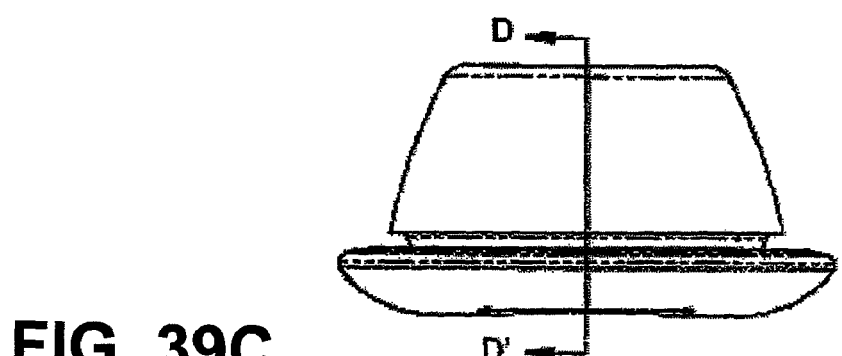
Figure 39D:
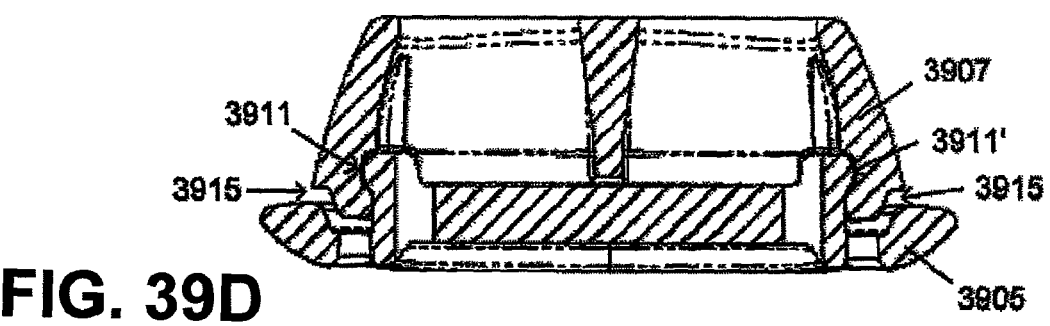

In the example shown in FIGS. 39A-39D, the inner and outer rim bodies are jointed together by two snaps (or snap-fits) 3911, 3911' which are visible in FIG. 39D. FIG. 39D shows a cross-section through FIG. 39C taken through line D-D'. The snaps 3911, 3911' are located at the inner portion of the ends of the long axis of the rim body, as indicated by 3913, 3913' on FIG. 39A. These snaps 3911, 3911' may allow the inner and outer rim bodies to be secured to one another. Although the adhesive holdfast is not shown in FIGS. 39A-39D, a channel region 3915 is included within the rim body (formed between the interface of the inner and outer rim bodies making up the rim body). The adhesive holdfast may be secured in this channel 3915. The channel 3915 in this exemplary device is configured differently than the channel described previously for securing the holdfast to the rim body (e.g., FIG. 3). For example, the channel 3915 extends downward into a concavity formed in the outer rim body, as seen in FIGS. 39B and 39D. This configuration may allow the device to have a more compact profile than configurations in which this channel projects horizontally between the inner and outer rim bodies, or upwards towards the inner rim body.

Figure 40A:
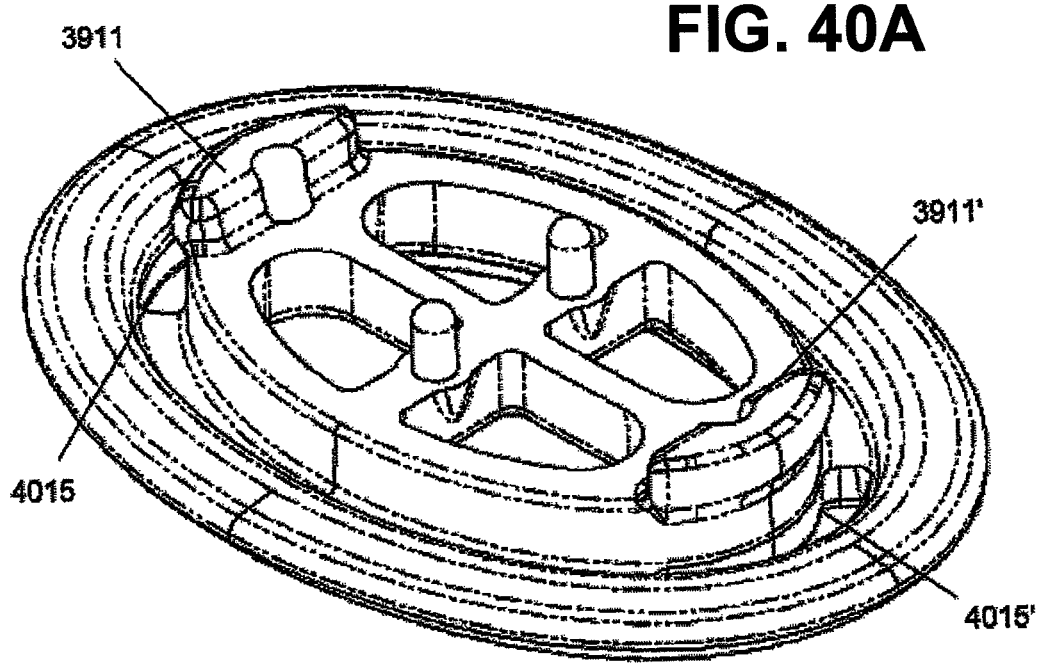
FIGS. 40A and 40B are perspective views of one variation of an outer rim body and an inner rim body, respectively.
Figure 40B:
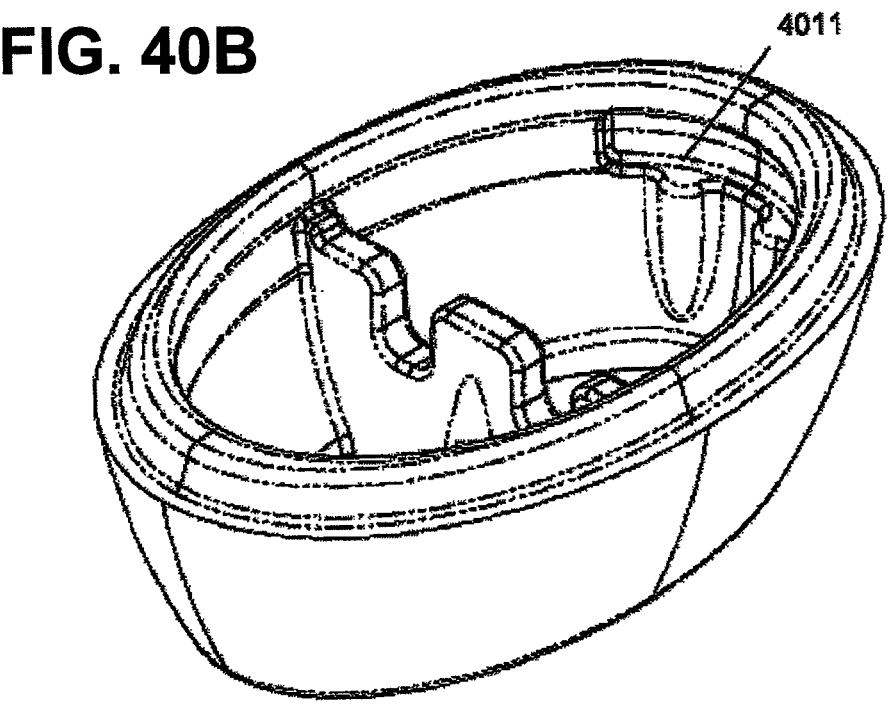

The two snap fit regions 3911, 3911' are shown more clearly in FIGS. 40A and 40B. FIGS. 40A and 40B are perspective views of the outer and inner rim body components, respectively. In this example, the outer rim body includes two projecting snaps 3911, 3911' that may mate with openings in the inner rim body 4011 (one of which is shown in FIG. 40B) to secure the two components together. As described previously, in some variations, the entire circumference around the main airflow passageway of the inner and outer rim bodies may interlock, or snap together, rather than just the two snap fittings shown in this embodiment. However, it may be advantageous to include snap fittings in only one or more regions (e.g., preferably two or more opposing regions) of the rim body. For example, the rim body (both inner and outer rim bodies) may be fabricated by injection molding. Fabrication of an undercut snap fitting portion may be simplified by including a pass core in the design. A pass core is a region near an undercut portion of the mold form that includes a passageway for a core element to fit, and thereby help form the undercut region. Two pass core regions 4015, 4015' can be seen in FIG. 40A.

Figure 41A:
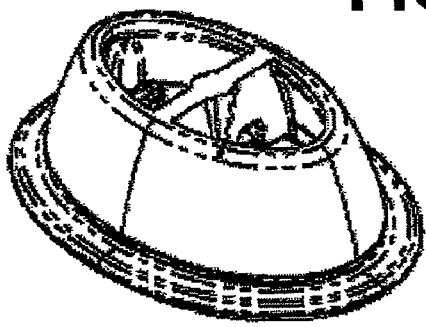
FIG. 41A is a perspective view of one variation of a rim body for an adhesive nasal device.
Figure 41B:
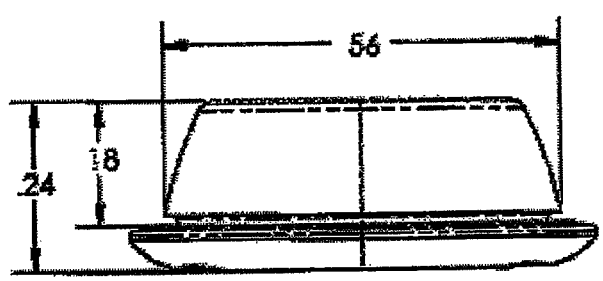
FIG. 41B-41D are perspective views of the rim body shown in FIG. 41A, including exemplary dimensions (in inches).
Figure 41C:
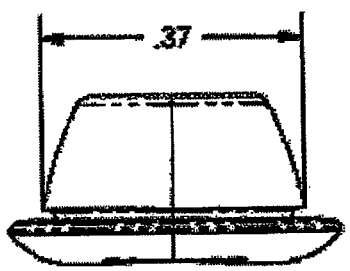
Figure 41D:
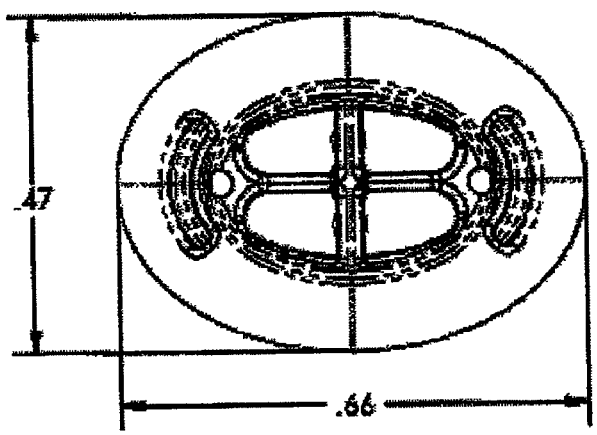

As mentioned previously, the adhesive nasal devices described herein may have any appropriate dimensions or shapes. FIGS. 41A to 41D illustrate one variation of a rim body in which exemplary dimensions (in inches) are indicated. For the sake of simplicity, the adhesive holdfast region of the device is not included in these figures, but would be included as part of the actual device. FIG. 41A shows a perspective view of a rim body region. FIG. 41B shows a side view (along the long axis of the device) of the rim body example shown in FIG. 41A. The maximum diameter of this inner rim body is 0.56 inches (shown as the length of the major axis of the inner rim body), while the maximum diameter of the outer rim body is approximately 0.66 inches (shown in FIG. 41D as the length of the major axis of the outer rim body). The height of this rim body is 0.24 inches, and the maximum diameter of the inner rim body is 0.37 inches, as shown in FIG. 41C. The maximum diameter of the outer rim body of this example is 0.47 inches.

The dimensions given above are approximate, and may be varied. In general, the rim body may be of any appropriate size so that the adhesive nasal device may be comfortably worn by a subject. For example, the rim body may be larger or smaller, and the generally elliptical opening of the rim body may be narrower or wider. In some variations, the size and dimensions may be adjusted so that the devices may be worn by subject having any size nasal opening.

Placement of the adhesive nasal devices may be done in front of a mirror or can occur without looking at a mirror. After placement of the adhesive nasal devices, the user may test whether an adequate seal has been created or has been maintained between the adhesive holdfast and the region in, on, over or around the nostrils through a variety of methods. In some cases, the user may place his finger or thumb on the outer rim body in an attempt to create a seal between the outer rim body and his finger/thumb. On exhalation for example, it will be clear to the user whether a good seal has been created between the device and his nasal cavity because exhalation will be more difficult. In some embodiments of the device, a sticker or similar adhesive means may be stuck to the outer rim body, which will serve to obstruct flow of air through the passageway defined by the outer rim body. During exhalation, the user will therefore be able to determine whether an adequate seal exists between the adhesive holdfast and the region in, on, over or around the nostrils. If a seal does not exist, then the user can make adjustments to ensure adequate sealing. Once the seal has been verified, then the user can remove the sticker or other adhesive means from the outer rim body and commence the use of the device.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A nasal device adapted to be secured in communication with a subject's nasal cavity, the device comprising:
    a rim having an opening therethrough;
    an airflow resistor in communication with the opening of the rim, wherein the airflow resistor is configured to inhibit airflow during expiration more than airflow during inspiration; and
    a flexible, adhesive holdfast extending outward from the rim.

2. The nasal device of claim 1, wherein the rim comprises an outer rim body secured to an inner rim body.

3. The nasal device of claim 1, wherein the rim is flexible.

4. The nasal device of claim 1, wherein the adhesive holdfast is configured to seal the nasal device around the subject's nostril.

5. The nasal device of claim 1, wherein the adhesive holdfast is configured to secure the airflow resistor in communication with both nostrils.

6. The nasal device of claim 1, wherein the airflow resistor comprises a flap valve.

7. The nasal device of claim 1, wherein the opening through the rim comprises an opening into a passageway through the rim.

8. The nasal device of claim 1, further comprising a protective cover configured to be removed from the adhesive holdfast to expose at least a portion of the biocompatible adhesive.

9. The nasal device of claim 1, wherein the rim comprises a rim body configured to project at least partially into a nostril when the adhesive holdfast is secured to a subject's nose.

10. The device of claim 1, wherein the adhesive holdfast extends from the periphery of the rim in a direction that is normal to the opening through the rim.

11. The device of claim 1, wherein the airflow resistor is configured to have a resistance to expiration between about 5 cm $H_2O$/(L/sec) and about 250 cm $H_2O$/(L/sec) when resistance is measured at a flow rate of 100 ml/sec.

12. The device of claim 1, further comprising a leak pathway through the nasal device configured to be open during both expiration and inspiration.

13. The device of claim 1, further comprising an adapter configured for use with an airflow or pressure measuring element.

14. The device of claim 13, wherein the adapter is a cannula adapter configured to connect to a cannula to measure airflow or pressure.

15. A nasal device adapted to be secured in communication with a subject's nasal cavity, the device comprising:
    a flexible adhesive holdfast extending outward from an opening, the adhesive holdfast configured to secure the nasal device at least partially over or at least partly within a subject's nostril; and
    an airflow resistor in communication with the opening, wherein the airflow resistor is configured to inhibit airflow during expiration more than airflow during inspiration.

16. The nasal device of claim 15, further comprising a rim body around the opening, wherein the flexible adhesive holdfast extends outward from the periphery of the rim body.

17. The nasal device of claim 16, wherein the rim body is flexible.

18. The nasal device of claim 15, wherein the airflow resistor comprises a flap valve.

19. The device of claim 15, wherein the airflow resistor is configured to have a resistance to expiration between about 5 cm $H_2O$/(L/sec) and about 250 cm $H_2O$/(L/sec) when resistance is measured at a flow rate of 100 ml/sec.

20. The nasal device of claim 15, further comprising a protective cover configured to be removed from the adhesive holdfast to expose at least a portion of the biocompatible adhesive.

21. The nasal device of claim 15, further comprising a rim configured to project at least partially into a nostril when the adhesive holdfast is secured to a subject's nose.

22. The device of claim 15, further comprising an adapter configured for use with an airflow or pressure measuring element.

23. The device of claim 22, wherein the adapter is a cannula adapter configured to connect to a cannula to measure airflow or pressure.

24. A method of treating a subject, the method comprising:
adhesively securing a nasal device at least partly over or at least partly within at least one of a subject's nostrils, the nasal device comprising
a flexible adhesive holdfast extending outward from an opening, and
an airflow resistor in communication with the opening, wherein the airflow resistor is configured to inhibit airflow during expiration more than airflow during inspiration; and
inhibiting expiration more than inspiration through the at least one nostril.

25. The method of claim 24, further comprising measuring airflow through the nasal device.

26. A method of treating a subject with a nasal device, the method comprising:
aligning an opening of the nasal device with an opening of a nostril of the subject;
securing the nasal device to skin surrounding the nostril opening; and
breathing through the opening of the nasal device to inhibit expiration more than inspiration through the nostril.

27. The method of claim 26 wherein the nasal device comprises an adhesive holdfast, the securing step comprising adhering the holdfast to the skin.

28. The method of claim 27 wherein the adhesive holdfast surrounds the opening of the nasal device.

29. The method of claim 26 further comprising sealing the nasal device to or around the nostril opening, the breathing step comprising passing all air entering the nostril through the nasal device.

30. The method of claim 26 wherein the nasal device comprises an airflow resistor, the breathing step comprising breathing through the airflow resistor.

31. The method of claim 26 wherein the nasal device comprises a rim, the aligning step comprising aligning the rim with the nostril opening.

* * * * *